(12) United States Patent
Bubeck Wardenburg

(10) Patent No.: US 9,150,865 B2
(45) Date of Patent: Oct. 6, 2015

(54) ROLE OF ADAM10 AND ITS RELEVANCE TO DISEASE AND THERAPEUTICS

(75) Inventor: Juliane Bubeck Wardenburg, Frankfort, IL (US)

(73) Assignee: The University of Chicago, Chicago, IL (US)

(*) Notice: Subject to any disclaimer, the term of this patent is extended or adjusted under 35 U.S.C. 154(b) by 0 days.

(21) Appl. No.: 13/884,502

(22) PCT Filed: Nov. 9, 2011

(86) PCT No.: PCT/US2011/060010
§ 371 (c)(1),
(2), (4) Date: Jul. 24, 2013

(87) PCT Pub. No.: WO2012/064865
PCT Pub. Date: May 18, 2012

(65) Prior Publication Data
US 2014/0178399 A1    Jun. 26, 2014

Related U.S. Application Data

(60) Provisional application No. 61/411,765, filed on Nov. 9, 2010, provisional application No. 61/453,648, filed on Mar. 17, 2011, provisional application No. 61/511,032, filed on Jul. 23, 2011, provisional application No. 61/511,030, filed on Jul. 23, 2011, provisional application No. 61/525,088, filed on Aug. 18, 2011.

(51) Int. Cl.
| | | |
|---|---|---|
| A61K 39/085 | (2006.01) |
| A61K 49/00 | (2006.01) |
| A61K 39/395 | (2006.01) |
| C12N 15/113 | (2010.01) |
| A61K 31/00 | (2006.01) |
| A61K 38/07 | (2006.01) |
| A61K 38/08 | (2006.01) |
| A61K 38/17 | (2006.01) |
| A61K 31/165 | (2006.01) |
| C07K 16/40 | (2006.01) |

(52) U.S. Cl.
CPC ............ *C12N 15/1137* (2013.01); *A61K 31/00* (2013.01); *A61K 31/165* (2013.01); *A61K 38/07* (2013.01); *A61K 38/08* (2013.01); *A61K 38/17* (2013.01); *A61K 39/085* (2013.01); *C07K 16/40* (2013.01)

(58) Field of Classification Search
CPC ..... A61K 39/00; A61K 39/02; A61K 39/085; A61K 39/395; A61K 39/40; A61K 49/00
USPC .................. 424/9.1, 9.2, 130.1, 133.1, 141.1, 424/150.1, 184.1, 234.1, 243.1
See application file for complete search history.

(56) References Cited

U.S. PATENT DOCUMENTS

| | | | |
|---|---|---|---|
| 6,172,064 B1 | 1/2001 | Andrews et al. | 514/237.8 |
| 6,191,150 B1 | 2/2001 | Andrews et al. | 514/352 |
| 6,329,400 B1 | 12/2001 | Andrews et al. | 514/336 |
| 7,629,341 B2 | 12/2009 | Bannen et al. | 514/235.8 |
| 7,638,302 B2 | 12/2009 | Maihle et al. | 435/69.1 |
| 7,989,661 B2 | 8/2011 | Bannen et al. | 562/828 |
| 8,034,783 B2 | 10/2011 | Moss et al. | 514/21.2 |
| 2005/0250789 A1 | 11/2005 | Burns | 546/245 |
| 2007/0049518 A1 | 3/2007 | Chandler et al. | 514/7 |
| 2009/0124649 A1 | 5/2009 | Yao | 514/278 |
| 2010/0173972 A1 | 7/2010 | Lemberg | 514/44 |

FOREIGN PATENT DOCUMENTS

| | | |
|---|---|---|
| CN | 102206206 | 10/2011 |
| WO | WO 03/051825 | 6/2003 |
| WO | WO 03/106381 | 12/2003 |
| WO | WO 2004100986 | 11/2004 |
| WO | WO 2009033742 | 3/2009 |
| WO | WO 2009140215 | 11/2009 |

OTHER PUBLICATIONS

Cenizal, M.J., et al. Antimicrobial Agents and Chemotherapy, vol. 51, No. 7, pp. 2628-2630, Jul. 2007.*
Bhakdi and Tranum-Jensen, *Microbiol. Rev.*, 55:733-751, 1991.
Brosnahan et al., *Immunol.*, 182:2364-2373, 2009.
Bubeck Wardenburg and Schneewind, *J. Exp. Med.*, 205:287-294, 2008.
Bubeck Wardenburg et al., *Infect. Immun.*, 75:1040-1044, 2007.
Bubeck Wardenburg et al., *Nature Med.*, 13:1405-1407, 2007.
Callegan et al., *Infect. Immun.*, 62:2478-2482, 1994.
Dinges, et al., *Clin Microbiol Rev.* 13(1):16, 2000.
Dudek et al., *Mol. Biol. Cell*, 21(22):4042-4056, 2010.
Gomez et al., *EMBO J.*, 26:701-709, 2007.
Gonzalez et al., *Cell Mol. Life Sci.*, 65:493-507, 2008.
Gumbiner, *Cell*, 84:345, 1996.
Hartmann et al., *Hum. Mol. Genet.*, 11:2615-2624, 2002.
Hoettecke et al., *Neurodegener. Dis.*, 7(4):232-238, 2010.
Hoy et al., *EMBO*, 11:798, 2010.
Iacovache et al., *Biochim Biophys Acta.*, 1778 (7-8): 1611-23, 2008.
Illek et al., *Cell Physiol. Biochem.*, 22:57-68, 2008.
International Preliminary Report on Patentability in International Application No. PCT/US2011/060010 mailed May 14, 2013.
Jursch et al., *Infect. Immun.*, 62:2249, 1994.
Karginov et al., *Bioorg. Med. Chem.*, 15:5424, 2007.
Kennedy et al., *J. Infect. Dis.*, 202(7):1050-1058, 2010.
Kim et al., *Cell Host Microbe.*, 8(1):20-35, 2010.
Kim et al., *Vaccine*, 28(38):6382-6392, 2010.

(Continued)

*Primary Examiner* — Rodney P Swartz
(74) *Attorney, Agent, or Firm* — Norton Rose Fulbright US LLP

(57) ABSTRACT

Certain embodiments are directed to compositions and methods of inhibiting pathogenic bacterial infection involving ADAM10 comprising administering an effective amount of a metalloprotease inhibitor to a patient. Certain embodiments are directed to method of inhibiting Staphylococcal infection comprising administering an effective amount of a metalloprotease inhibitor to a patient. Other embodiments concern methods of inhibiting infection by a bacteria from the genus *Clostridium, Streptococcus, Listeria, Bacillus*, or *Arcanobacterium*.

16 Claims, 18 Drawing Sheets

(56) References Cited

OTHER PUBLICATIONS

Lemichez et al., *Nat. Rev. Microbiol.*, 8(2):93-104, 2010.
Lowy, *N. Engl. J. Med.*, 339:520, 1998.
Ludwig et al., *Comb. Chem. High Throughput Screen*, 8:161-171, 2005.
Maretzky et al., *J. Invest. Dermatol.*, 128:1737-1746, 2008.
Maretzky et al., *Proc. Natl. Acad. Sci. USA*, 102:9182-9187, 2005.
Marriott and Dockrell, *Int. J. Biochem. Cell Biol.*, 38:1848-1854, 2006.
Martin et al., *Infect. Immun.*, 79:1898-1904, 2011.
Matthay and Zemans, *Annu. Rev. Pathol.*, 28:147-163, 2011.
Matthay and Zemans, *Annu. Rev. Pathol.*, 6:147, 2010.
Menzies and Kernodle, *Infect. Immun*, 64:1839-1841, 1996.
Menzies and Kernodle, *Infect. Immun.*, 62:1843-1847, 1994.
Murphy, *Semin. Cell Dev. Biol.*, 20:138-145, 2009.
O'Callaghan et al., *Infect. Immun.*, 65:1571-1578, 1997.
Ong and Leung, *Immun. Allergy Clincis of NA*, 30:309-321, 2010.
Patel et al., *Infect. Immun.*, 55:3103-3110, 1987.
Perl et al., *Proc. Natl. Acad. Sci. USA*, 99:10482-10487, 2002.
Perl et al., *Transgenic Res.*, 11:21-29, 2002.
Pochetuhen et al., *Am. J. Pathol.*, 171(2):428-437, 2007.
Ragle et al., *Antimicrob. Agents Chemother.*, 54:298, 2010.
Reiss and Saftig, *Semin. Cell Dev. Biol.*, 20:126-137, 2009.
Rubins et al., *J. Clin. Invest.*, 95:142-150, 1995.
Schulz et al., *Circ. Res.*, 102(10):1192-1201, 2008.
Seals and Courtneidge, *Genes Dev.*, 17:7-30, 2003.
Search Report and Written Opinion in International Application No. PCT/US2011/060010 mailed Feb. 29, 2012.
Shapiro and Weis, *Cold Spring Herb. Perspect. Biol.*, 1:a003053, 2009.
Song et al., *Science*, 274:1859-1866, 1996.
Tian et al., *Int. Immunol.*, 20:1181-1187, 2008.
Tomita and Kannio, *Biosci. Biotechnol. Biochem.*, 61:565-572, 1997.
Tweten, *Infection and Immunity*, 73 (10): 6199-6209, 2005.
Vasioukhin et al., *Proc. Natl. Acad. Sci. USA*, 96:8551-8556, 1999.
Walker and Bayley, *J. Biol. Chem.*, 270:23065, 1995.
Wilke and Bubeck Wardenburg, *Proc. Natl. Acad. Sci. USA*, 107(30):13473-13478, 2010.
Wu et al., *Proc. Natl. Acad. Sci. USA*, 95:14979, 1998.
Duffy et al., "The ADAMs family of proteases: new biomarkers and therapeutic targets for cancer?" *Clin. Proteo.* 8(1):9, 2011.
Galardy, "Galardin™ Antiinflammatory Protease Inhibitor", *Drugs of the Future* 18(12):1109-1111, 1993.
Lemjabbar et al., "Platelet-activating factor receptor and ADAM10 mediate responses to *Staphylococcus aureus* in epithelial cells", *Nature Medicine* 8(1):41-46, 2002.
Lin et al., "New insights into the prevention of staphlococcal infections and toxic shock syndrome", *Expert Review of Clinical Pharmacology* 3(6):753-767, 2010.
Min et al., "Roles of Matrix Metalloproteinases on Intracellular *Staphylococcus aureus* Growth in Bronchial Epithelial Cell", *Tub. Resp. Diseases* 64(1):22-27, 2008.

\* cited by examiner

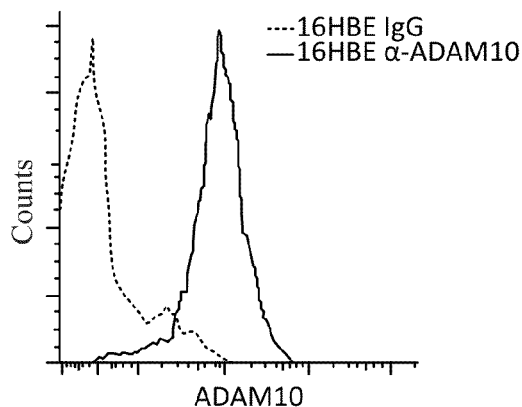
Figure 18A
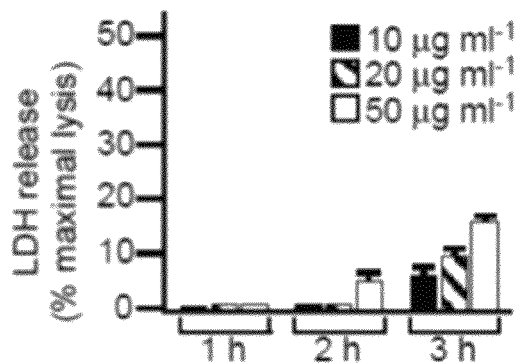
Figure 18B
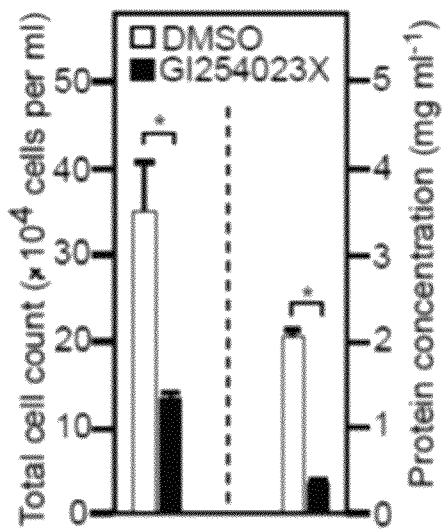
Figure 19A
| | Hemolysis (OD$_{450}$) |
|---|---|
| Hla+DMSO | 3.02±0.01 |
| Hla+GI254023X | 3.13±0.01 |
| rRBC+DMSO | 2.97±0.04 |
| rRBC+GI254023X | 0.35±0.006 |
Figure 19B

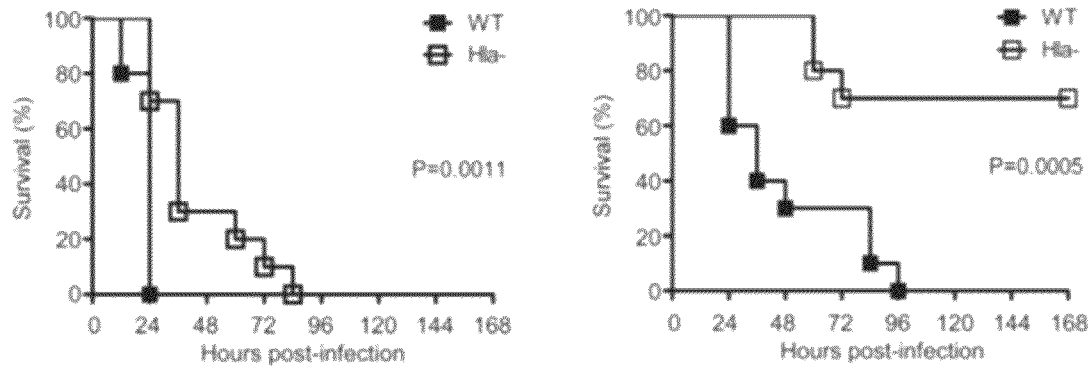
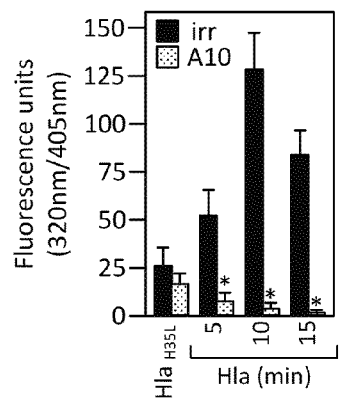
Figure 20A
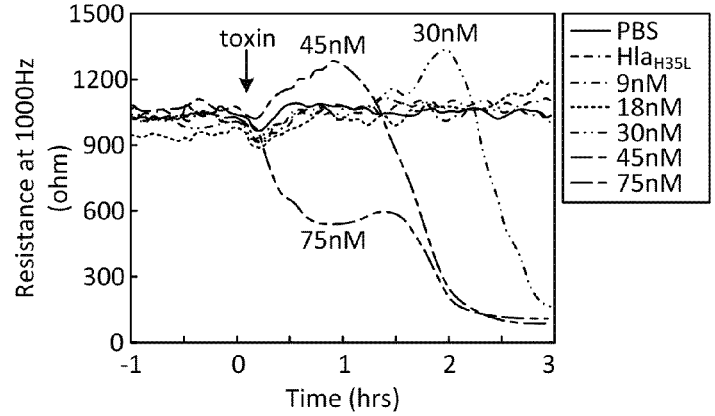
Figure 20B  Figure 20C
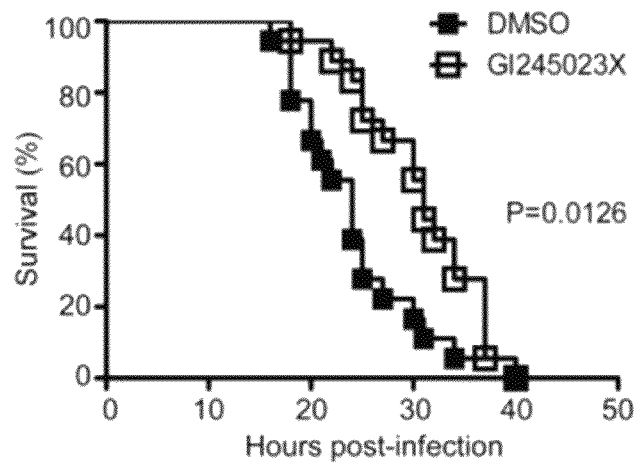
Figure 21

SEQUENCE LISTING

```
<160> NUMBER OF SEQ ID NOS: 5

<210> SEQ ID NO 1
<211> LENGTH: 190
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: Xaa can be Cys, Ala or Ser

<400> SEQUENCE: 1

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Arg Leu Asp Phe His Ala His Gly Arg His
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Leu Asp Tyr Asp Thr Ser His Ile
65                  70                  75                  80

Tyr Thr Gly His Ile Tyr Gly Glu Glu Gly Ser Phe Ser His Gly Ser
                85                  90                  95

Val Ile Asp Gly Arg Phe Glu Gly Phe Ile Gln Thr Arg Gly Gly Thr
            100                 105                 110

Phe Tyr Val Glu Pro Ala Glu Arg Tyr Ile Lys Asp Arg Thr Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg Met
145                 150                 155                 160

Arg Lys Tyr Gln Met Thr Gly Val Glu Glu Val Thr Gln Ile Pro Gln
                165                 170                 175

Glu Glu His Ala Ala Asn Gly Pro Glu Leu Leu Arg Lys Lys
            180                 185                 190

<210> SEQ ID NO 2
<211> LENGTH: 159
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: Xaa can be Cys, Ala or Ser

<400> SEQUENCE: 2
```

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Arg Leu Asp Phe His Ala His Gly Arg His
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Leu Asp Tyr Asp Thr Ser His Ile
65                  70                  75                  80

Tyr Thr Gly His Ile Tyr Gly Glu Gly Ser Phe Ser His Gly Ser
                85                  90                  95

Val Ile Asp Gly Arg Phe Glu Gly Phe Ile Gln Thr Arg Gly Gly Thr
            100                 105                 110

Phe Tyr Val Glu Pro Ala Glu Arg Tyr Ile Lys Asp Arg Thr Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg
145                 150                 155

<210> SEQ ID NO 3
<211> LENGTH: 154
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: Xaa can be Cys, Ala or Ser

<400> SEQUENCE: 3

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Arg Leu Asp Phe His Ala His Gly Arg His
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Leu Asp Tyr Asp Thr Ser His Ile
65                  70                  75                  80

Tyr Thr Gly His Ile Tyr Gly Glu Gly Ser Phe Ser His Gly Ser
                85                  90                  95

Val Ile Asp Gly Arg Phe Glu Gly Phe Ile Gln Thr Arg Gly Gly Thr
            100                 105                 110

Phe Tyr Val Glu Pro Ala Glu Arg Tyr Ile Lys Asp Arg Thr Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His
145                 150

<210> SEQ ID NO 4
<211> LENGTH: 159
<212> TYPE: PRT
<213> ORGANISM: Homo sapiens
<220> FEATURE:

```
<221> NAME/KEY: MISC_FEATURE
<222> LOCATION: (156)..(156)
<223> OTHER INFORMATION: Xaa can be Cys, Ala or Ser

<400> SEQUENCE: 4

Gly Gly Gln Tyr Gly Asn Pro Leu Asn Lys Tyr Ile Arg His Tyr Glu
1               5                   10                  15

Gly Leu Ser Tyr Asn Val Asp Ser Leu His Gln Lys His Gln Arg Ala
            20                  25                  30

Lys Arg Ala Val Ser His Glu Asp Gln Phe Leu Arg Leu Asp Phe His
        35                  40                  45

Ala His Gly Arg His Phe Asn Leu Arg Met Lys Arg Asp Thr Ser Leu
    50                  55                  60

Phe Ser Asp Glu Phe Lys Val Glu Thr Ser Asn Lys Val Leu Asp Tyr
65                  70                  75                  80

Asp Thr Ser His Ile Tyr Thr Gly His Ile Tyr Gly Glu Glu Gly Ser
                85                  90                  95

Phe Ser His Gly Ser Val Ile Asp Gly Arg Phe Glu Gly Phe Ile Gln
                100                 105                 110

Thr Arg Gly Gly Thr Phe Tyr Val Glu Pro Ala Glu Arg Tyr Ile Lys
            115                 120                 125

Asp Arg Thr Leu Pro Phe His Ser Val Ile Tyr His Glu Asp Asp Ile
        130                 135                 140

Asn Tyr Pro His Lys Tyr Gly Pro Gln Gly Gly Xaa Ala Asp His
145                 150                 155

<210> SEQ ID NO 5
<211> LENGTH: 12
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 5

His Glu Xaa Gly His Asn Leu Gly Xaa Xaa His Asp
1               5                   10
```

ROLE OF ADAM10 AND ITS RELEVANCE TO DISEASE AND THERAPEUTICS

This application is a national phase application under 35 U.S.C. §371 of International Application No. PCT/US2011/060010 filed Nov. 9, 2011, which claims priority to U.S. Provisional Patent Application Ser. No. 61/411,765 filed Nov. 9, 2010, U.S. Provisional Patent Application Ser. No. 61/453,648 filed Mar. 17, 2011, U.S. Provisional Patent Application Ser. No. 61/511,032 filed Jul. 23, 2011, U.S. Provisional Patent Application Ser. No. 61/511,030 filed Jul. 23, 2011, and U.S. Provisional Patent Application Ser. No. 61/525,088, filed Aug. 18, 2011, each of which is incorporated herein by reference in its entirety.

This invention was made with government support under grant U54AI57153 awarded by the National Institutes of Health through the Great Lakes Regional Center of Excellence for Bio-defense and Emerging Infectious Diseases Research Program and by the University of Chicago Institute for Translational Medicine (ITM), grant number UL1RR024999 from the National Center for Research Resources (NCRR), a component of the National Institutes of Health (NIH), and NIH Roadmap for Medical Research. The government has certain rights in the invention.

BACKGROUND OF THE INVENTION

A. Field of the Invention

Embodiments of this invention are directed generally to microbiology and medicine. In certain aspects the invention is directed to treatment of *Staphylococcus* and *Streptococcus* infection.

B. Background

The number of both community acquired and hospital acquired infections have increased over recent years with the increased use of intravascular devices. Hospital acquired (nosocomial) infections are a major cause of morbidity and mortality, particularly in the United States, where it affects more than 2 million patients annually. The most frequent infections are urinary tract infections (33% of the infections), followed by pneumonia (15.5%), surgical site infections (14.8%) and primary bloodstream infections (13%) (Emorl and Gaynes, 1993).

The major nosocomial pathogens include *Staphylococcus aureus*, coagulase-negative Staphylococci (mostly *Staphylococcus epidermidis*), enterococcus spp., *Escherichia coli*, *Clostridium difficile* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens. Staphylococci can cause a wide variety of diseases in humans and other animals through either toxin production or invasion.

Epithelial barriers are a potent host defense against invasive bacterial infection. Pathogens circumvent this barrier through virulence factors that target specific structural elements of the epithelium, impairing its integrity (Kim et al., 2010). Critical bacterial targets within the epithelium include focal adhesion complexes, apical tight junction proteins, and the cadherin:catenin protein complex that comprises the adherens junction. *Staphylococcus aureus* is a leading cause of bacteremia, pneumonia, skin and soft tissue infection and lethal toxin-mediated syndromes (Lowy, 1998). This organism exhibits a dual interaction with its human host, existing as a harmless skin commensal and deadly invasive pathogen armed with multiple virulence factors. *S. aureus* alpha-hemolysin (Hla) is a pore-forming cytotoxin that contributes to the pathogenesis of pneumonia, dermonecrotic skin infection, and corneal infection (O'Callaghan et al., 1997; Kennedy et al., 2010; Bubeck Wardenburg et al., 2007a, 2007b). Further, Hla potentiates the penetration of *S. aureus* toxic shock syndrome toxin across the vaginal epithelium (Brosnahan et al., 2009).

A significant clinical burden of *S. aureus* skin infection is also apparent in individuals with several immunodeficiency states and atopic dermatitis, a chronic disease in which up to 90% of afflicted patients harbor *S. aureus* in lesional and non-lesional skin (Ong and Leung, 2010). Host defense against *S. aureus* skin infection is multifaceted, relying most importantly on local innate immunologic control through $T_H17$ and IL-10 driven recruitment of neutrophils in addition to the protective actions of β-defensins and the cutaneous barrier. Pathogen virulence in acute staphylococcal infection is likewise multifactorial, relying in part on α-hemolysin (Hla), a pore-forming cytotoxin secreted by almost all strains of *S. aureus* (Bhakdi and Tranum-Jensen, 1991). Hla is required for dermonecrotic changes in skin infection, also contributing positively to abscess size (Kennedy et al., 2010; Patel et al., 1987. Immunization strategies targeting Hla afford protection against dermonecrosis (Kennedy et al., 2010). Indeed, *S. aureus* is the most common bacterial pathogen that complicates atopic dermatitis lesions (Ong and Leung, 2010), demonstrated to express the V8 protease and immunomodulatory virulence factors that have also been described to adversely impact on epithelial barrier function.

There remains a need to develop effective compositions and treatments for staphylococcal and other pathogenic bacterial infections.

SUMMARY OF THE INVENTION

*Staphylococcus aureus* remains a leading cause of infectious disease morbidity and mortality. This human commensal must breach the innate epithelial barrier defense to cause invasive disease. The highly conserved pore-forming cytotoxin α-hemolysin (Hla) injures diverse epithelial cells by interacting with the zinc-dependent metalloprotease A Disintegrin and Metalloprotease 10 (ADAM10) as its receptor. Alveolar epithelial exposure to α-hemolysin upregulates cellular ADAM10 enzymatic activity, resulting in E-cadherin cleavage. This cleavage event causes a physiologic disruption of epithelial barrier function, associated with both acute lung injury and penetration of toxic-shock syndrome toxin 1 (TSST-1) into the vaginal mucosal. Thus, a bacterial cytotoxin can usurp the activity of its receptor, leading to a direct and rapid modification of epithelial cell-cell contacts.

Certain embodiments are directed to methods of inhibiting Staphylococcal infection comprising administering an effective amount of a metalloprotease inhibitor to a patient. Other embodiments concern methods of inhibiting infection by a bacteria from the genus *Clostridium, Streptococcus, Listeria, Bacillus*, or *Arcanobacterium*.

The methods can include treating a subject having or at risk of developing a Staphylococcal infection comprising administering an effective amount of a metalloprotease inhibitor to a subject having or at risk of developing a Staphylococcal infection.

The methods can also include treating pore-forming toxin-inducted pathology in a subject comprising administering an ADAM10 inhibitor to a subject exposed to a pore-forming toxin. In certain embodiments, the pathology is related to infection by a species of the genus *Clostridium, Streptococcus, Listeria, Bacillus*, or *Arcanobacterium*. In certain embodiments, the pathology is related to infection by a species of the genus *Staphylococcus*.

In some embodiments, the pore-forming toxin is alpha-hemolysin (Hla). In certain methods, the Hla induced pathology is pulmonary edema, obliteration of alveolar space, skin lesions, sepsis, and toxic shock.

In additional embodiments, the pore-forming toxin is pneumolysin (PLY) or Streptolysin O (SLO). In certain methods, the PLY-induced pathology is pulmonary edema, obliteration of alveolar space, skin lesions, sepsis, and toxic shock.

The methods can also include inhibiting pore-forming toxin-induced cleavage of cadherins in a subject comprising administering a metalloprotease inhibitor to a subject exposed to a pore-forming toxin. In some embodiments, the pore-forming toxin is Hla. In additional embodiments, the pore-forming toxin is PLY or SLO.

The methods can also include ameliorating disruption of an epithelial membrane comprising contacting an epithelial membrane that has been exposed to a pore-forming toxin with a metalloprotease inhibitor. In some embodiments, the pore-forming toxin is Hla. In additional embodiments, the pore-forming toxin is PLY or SLO. In further embodiments, the pore-forming toxin is from a bacteria species of the genus *Clostridium, Streptococcus, Listeria, Bacillus*, or *Arcanobacterium*.

The methods can also include ameliorating disruption of an endothelial membrane comprising contacting an endothelial membrane that has been exposed to a pore-forming toxin with a metalloprotease inhibitor. In some embodiments, the pore-forming toxin is Hla. In additional embodiments, the pore-forming toxin is PLY or SLO.

The methods can also include inhibiting, attenuating, treating, or ameliorating toxic-shock syndrome and its related pathology.

The methods can also include ameliorating disruption of an epithelial membrane comprising contacting an epithelial membrane that has been exposed to alpha-hemolysin with a metalloprotease inhibitor. In certain embodiments, the alpha-hemolysin, PLY or SLO is from a pathogenic bacteria.

Other embodiments include methods of treating pneumonia in a patient who has signs of pneumonia or has been diagnosed with or tested positive for pneumonia comprising administering a composition comprising a metalliprotease inhibitor to the patient. Embodiments include methods of treating pneumonia comprising administering an effective amount of a metalloprotease inhibitor to a patient, wherein the patient has been determined to have or be at risk of developing pneumonia caused by Staphylococcal infection or by *Streptococcus* infection.

Additional embodiments include methods for treating or preventing atopic dermatitis lesions comprising administering an effective amount of a metalloprotease inhibitor to a patient. In some embodiments, the patient has been determined to have or be at risk for a Staphylococcal infection. In further embodiments, the patient exhibits an abscess, boil, or furuncle.

Several embodiments concern methods for preventing or treating dermonecrosis in a patient comprising administering an effective amount of a metalloprotease inhibitor to the patient. In some embodiments, the patient has been determined to have or be at risk for a Staphylococcal infection. In further embodiments, the patient has been determined to have or be at risk for dermonecrosis. In further embodiments, the patient exhibits an abscess, boil, or furuncle.

In further embodiments methods can include treating a subject having or at risk of developing a pharyngitis (e.g., a pharyngitis associated with *Arcanobacterium* infection) comprising administering an effective amount of a metalloprotease inhibitor to the subject.

In certain embodiments, a method is provided for treating an domestic animal having or at risk of developing an infection with a bacterial pathogen described herein. For example, the method can comprising administering an metalloprotease inhibitor (e.g., an inhibitor of A Disintegrin and Metalloprotease 10 (ADAM10)) to the animal having or at risk of developing an infection. In some aspects, methods are provided for treating or preventing animal infections by bacteria expressing pore-forming toxins, in particular toxins subject to inhibition by an ADAM10 inhibitors. For example, methods according to the embodiments can comprise treating or preventing an *Arcanobacterium pyogenes* or *Staphylococcus aureus* infection in an animal by administering a metalloprotease inhibitor described herein.

In certain embodiments a method is provided for treating a cow having or at risk of developing bovine mastitis (e.g., mastitis associated with *S. aureus* infection) comprising administering an effective amount of a metalloprotease inhibitor to the cow.

The metalloprotease inhibitor may be in a pharmaceutical composition that is administered to the patient. In certain aspects the patient has been determined to have or be at risk of developing a Staphylococcal infection. In further aspects, the metalloprotease inhibitor is an inhibitor of ADAM10. In a further aspect, the ADAM10 inhibitor inhibits ADAM10 activity or inhibits ADAM10 expression. ADAM10 activity refers to its protease activity. The ADAM10 inhibitor can be an inhibitory nucleic acid, polypeptide, peptide, or small molecule. In certain aspects, the ADAM10 inhibitor inhibits ADAM10 activity. The ADAM10 inhibitor can inhibit ADAM10 activity by inhibiting an ADAM10 polypeptide. In certain aspects, the ADAM10 inhibitor is an ADAM10 specific antibody or immunoglobulin. The ADAM10 specific antibody or immunoglobulin can be a polyclonal antibody, a monoclonal antibody, or an antibody fragment.

In certain aspects, the metalloprotease inhibitor includes, but is not limited to INCB7839; INCB3619; XL784; XL081; XL781; GI254023X; GW280264X; ABT518; Neovastat; Psovascar; BAY129566; Batimastat; DA125; AG3340; nephrostat; incyclinide; ISV120; ISV615; marimastat; prinomastat; doxycycline; PCK3145; telmesteine; RAV18; ALCH1005; ALSL1023; inulin fiber; TIMP2; AZD1236; rebimastat; D1927; CTS1027; DAC:MMPI; CPA926; DX2400; Vasosten; PerioNx; BB3644; BB2827; MMI270; 0N04817; AG3433; apratastat; PG116800; PG530742; CR3294; 53304; 53536; INN01137; INN01147; CDP845; CT1166; CT1746; D9120; PG116800; PG530742; cipemastat; WY48989; PUP1; MMP Protease Inhibitor; V85546; MMP-13; CR074; CP471358; galarubicin; (R)—N4-Hydroxy-N1-[(S)-2-(1H-indol-3-yl)-1-methylcarbamoyl-ethyl]-2-isobutyl-succinamide (Ilomastat); 1,10-Phenanthroline monohydrate, 4-Aminobenzoyl-Gly-Pro-D-Leu-D-Ala hydroxamic acid (FN-439); α2-Macroglobulin from human plasma (α2-M); 3-[[1-[(2-(Hydroxymethyl)-1-pyrrolidinyl) carbonyl]-2-methylpropyl]carbamoyl]octanohydroxamic acid; Bestatin hydrochloride (N—R2S,3R)-3-Amino-2-hydroxy-4-phenylbutyrylR-leucine hydrochloride); Dichloromethylenediphosphonic acid disodium salt (DMDP); Doxycycline hydrate; Ethylenediaminetetraacetic acid disodium salt dihydrate; Isoamylphosphonyl-Gly-Pro-Ala dipotassium salt; N-(Methoxysuccinyl)-Ala-Ala-Pro-Val-chloromethyl ketone (N-(Methoxysuccinyl)-L-alanyl-L-alanyl-L-prolyl-L-valine chloromethylketone); Phosphoramidon disodium salt (N-(α-Rhamno-pyranosyl-phos-phono)-L-leucyl-L-tryptophan disodium salt, N-(α-Rhamno-pyranosyl-oxy-hydroxy-phosphinyl)-Leu-Trp disodium salt); Pro-Leu-Gly hydroxamate hydrochloride; Z-Pro-Leu-Gly hydroxamate; 7-Methoxycoumarin-4-acetyl-Arg-Pro-Lys-Pro-Tyr-Ala-Nva-Trp-Met-(2,4-dinitrophenyl)Lys amide; 7-Methoxycoumarin-4-acetyl-Pro-Leu-Gly-Leu-β-(2,4-dinitrophenylamino)Ala-Arg amide (7-Methoxycoumarin-4-acetyl-P-L-G-L-β-(2,4-dinitrophenylamino)A-R amide); N-(2,4-Dinitrophenyl)-Pro-Leu-Gly-Cys(Me)-His-Ala-D-Arg amide; Nobiletin (3',4',5,6,7,8-Hexamethoxyflavone); TAPI-1; BMS-275291; CGS27023A; (6S,7S)—N-hydroxy-5-methyl-6-[(4-phenylpiperidin-1-yl)carbonyl]-5-azaspiro[2.5]octane-7-carboxamide; (6S,7S)—N-hydroxy-5-methyl-6-[(4-phenyl-3,6-dihydropyridin-1(2H)-yl)carbonyl]-5-azaspiro[2,5]octane-7-carboxamide; (6S,7S)—N-Hydroxy-6-{[(3-phenylpyrrolidin-1-yl]carbonyl}-5-azaspiro[2.5]octane-7-carboxamide; (6S,7S)—N-hydroxy-6-((4-(methylsulfonyl)phenyl)-3,6-d-ihydropyridin-1 (2H)-yl) carbonyl)-5-azaspiro (2,5)octane-carboxamide; (2S,3S)—N-hydroxyl-1-methyl-2-((10aS)-3,4,10,10a-tetrahydropyrazino(1,-2-a)indol-2(1H)-yl-carbonyl) piperidine-3-carboxamide; (6S,7S)—N-hydroxy-6-((10aS)-3,4,10,10a-tetrahydropyrazino(1,2-a)-indol-2(1H)-yl-carbonyl)-5-azaspiro(2,5)octane-7-carboxamide; (6S,7S)—N-hydroxy-6-((4-(3-(methylsulfonyl)phenyl)-3,6-dihydropyridin-1-(2H)-yl)carbonyl)-5-azaspiro(2,5)octane-7-carboxamide, methyl (6S,7S)-7-[(hydroxyamino) carbonyl]-6-[(4-phenyl-3,6-dihydropyridin-1(2H)-yl) carbonyl]-5-azaspiro[2,5]octane-5-carboxylate; benzyl (6S, 7S)-7-[(hydroxyamino)carbonyl]-6-[(4-phenyl-3,6-dihydropyridin-1(2H)-yl)carbonyl]-5-azaspiro[2.5]octane-5-carboxylate; or (6S,7S)—N-Hydroxy-5-(methylsulfonyl)-6-[(4-phenyl-3,6-dihydropyridin-1(2H)-yl)carbonyl]-5-azaspiro[2,5]octane-7-carboxamide; (6S,7S)—N-Hydroxy-6-{[4-(3-methoxyphenyl)piperidin-1-yl]carbonyl}-5-methy-1-5-azaspiro[2.5]octane-7-carboxamide.

In certain aspects the metalloprotease inhibitor is GI254023X, GM6001, TIMP3, or TAPI-1 (N—(R)-[2-hydroxyaminocarbonyl)methyl]-4-methylpentanoyl-L-napthylalanyl-L-alanine, 2-aminoethyl amide). In certain aspects the metalloprotease inhibitor is INCB7839, INCB3619, XL784, XL081, XL781; GI254023X or GW280264X. In certain aspects the metalloprotease inhibitor is XL784.

In certain aspects the metalloprotease inhibitor is an anti-infective. In certain aspects the metalloprotease inhibitor is an antibiotic. In certain aspects the metalloprotease inhibitor is an anti-infective that decreases the risk of infection or complications from infection without killing the pathogen.

In certain aspects an inhibitory nucleic acid is a deoxyribonucleic acid (DNA), an siRNA, an miRNA, or a ribozyme.

In a further aspect, a metalloprotease inhibitor is administered orally, topically, intravascularly, intrathecally, intratracheally, by inhalation, or by instillation. The metalloprotease inhibitor can be administered to various organs or tissues including, but not limited to the subject's skin, respiratory tract (including the lungs) kidneys, central nervous system, reproductive organs, vagina, or eyes.

Certain embodiments further comprise administering a second anti-microbial treatment. In certain aspects the second anti-microbial treatment is an antibiotic agent, an anti-infective agent, a passive vaccine, or an active vaccine.

In certain embodiments, an animal feed comprising an metalloprotease inhibitor (e.g., an ADAM10 inhibitor) is provided. For example, the animal feed can be a feed for dogs, cats, cattle, pigs, chickens, goats, sheep or horses.

In a further embodiment a composition is provided comprising a metalloprotease inhibitor (e.g., an ADAM10 inhibitor) and a second anti-microbial agent, wherein the second anti-microbial agent is not a metalloprotease inhibitor. For example, the second antimicrobial agent can be an antibiotic, an antiseptic (e.g., an alcohol, iodine or silver composition) or a bacteriostatic agent. In certain aspects, a composition of the embodiments can be formulated for topical administration such as a spray, a gel, or a cream. For example, a composition can be absorbed into a fabric pad, such as wipe, for topical application. In some aspects, a composition of the embodiments can be formulated for oral or nasal administration such as a spray, an ointment, a cream, a syrup or a mouthwash. In some aspects, a composition of the embodiments is essentially free of anti-viral agents or chemotherapeutic agents.

In still further aspects, a composition of the embodiments comprises an ADAM10 inhibitor such as I254023X, GM6001, TIMP3, or TAPI-1 (N—(R)-[2-hydroxyaminocarbonyl)methyl]-4-methylpentanoyl-L-napthylalanyl-L-alanine, 2-aminoethyl amide), INCB7839, INCB3619, XL784, XL081, XL781, GI254023X or GW280264X and a second anti-microbial agent, wherein the second anti-microbial agent is not a metalloprotease inhibitor.

In yet a further embodiment a method of preventing infection in a patient is provided comprising administering to the patient a composition comprising a metalloprotease inhibitor (e.g., an ADAM10 inhibitor) and a second anti-microbial agent, wherein the second anti-microbial agent is not a metalloprotease inhibitor. In certain aspects, the patient is at risk for Streptococcal infection or Staphylococcal infection, such as a patient undergoing surgery or an immune compromised patient. In some aspects the patient is not a patient having cancer, HIV or HCV infection.

In certain aspects, the Staphylococcal infection is a *Staphylococcus aureus* infection. In a further aspect the *Staphylococcus aureus* infection is a drug resistant *Staphylococcus aureus* infection. In still another aspect the drug resistant *Staphylococcus aureus* infection is a methicillin-resistant *Staphylococcus aureus* (MRSA) infection.

In additional embodiments, the pathogenic bacterial infection is a *Streptococcus pneumoniae* infection.

In a further aspect the method can further comprise selecting the patient after the patient is diagnosed with a pathogenic bacterial infection, such as one involving an HLA, SLO or PLY toxin. The method can also further comprise the step of testing the patient for a pathogenic bacterial infection. The method can include obtaining from the patient a biological sample for testing whether the patient has a pathogenic bacterial infection. In additional embodiments, the patient is tested for the type of pathogenic bacterial infection. In certain embodiments, the patient is tested for MRSA or pneumonia.

In certain aspects of the methods the patient is determined to have a Staphylococcal infection. The methods can further comprise identifying the patient as having a Staphylococcal infection. In a further aspect the method can further comprise selecting the patient after the patient is diagnosed with a Staphylococcal infection. The method can also further comprise the step of testing the patient for a Staphylococcal infection. The method can include obtaining from the patient a biological sample for testing whether the patient has a Staphylococcal infection. In additional embodiments, the patient is tested for the type of Staphylococcal infection. In certain embodiments, the patient is tested for MRSA or pneumonia.

In certain aspects of the methods the patient is determined to have a *Streptococcus* infection. The methods can further comprise identifying the patient as having a *Streptococcus* infection. In a further aspect the method can further comprise selecting the patient after the patient is diagnosed with a *Streptococcus* infection. The method can also further comprise the step of testing the patient for a *Streptococcus* infection. The method can include obtaining from the patient a biological sample for testing whether the patient has a *Streptococcus* infection. In additional embodiments, the patient is tested for the type of *Streptococcus* infection. In certain embodiments, the patient is tested for pneumonia.

A patient is a human patient. It is contemplated that any embodiment involving a patient may also be applied to a subject, which refers to any organism that suffers physiologically as a result from infection by *Staphylococcus*. In certain embodiments, the subject is a mammal, which includes but is not limited to dogs, cats, cows, horses, pigs, monkeys, and sheep. In certain aspects, the patient is not a patient that has been determined to have cancer or that is under treatment for cancer. In some aspects, the subject is defined as a subject that has not been determined to have an HIV or HCV infection.

In certain aspects a patient is administered a metalloprotease inhibitor within at least about, at most about, or about 1, 2, 3, 4, 5, 6, 7, 8, 9, or 10 hours, days, or weeks of being determined to have a Staphylococcal infection.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of an ADAM10 inhibitor, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 nanograms (ng), micrograms (mcg), milligrams (mg), or grams of ADAM10 inhibitor, or any range derivable therein, in one dose or collectively in multiple doses. In some embodiments, the composition comprises between about 0.1 ng and about 2.0 g of ADAM10 inhibitor.

Alternatively, the composition may have a concentration of ADAM10 inhibitor that is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/ml or mg/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (µl) or milliliters (ml), or any range derivable therein. In certain embodiments, the patient is administered up to about 10 ml of the composition.

The amount of ADAM10 inhibitor that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/kilogram (kg) or mg/kg, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a pathogenic bacterial infection.

In a further aspect the patient can be at risk for *Staphylococcus* infection. In another embodiment the patient can be at risk for *Streptococcus* infection. In additional embodiments the patient is at risk for a pathogenic bacterial infection. In still further aspects, the patient is at risk for pneumonia.

Certain embodiments are directed to methods where the patient is immune deficient, is immunocompromised, is hospitalized, is undergoing an invasive medical procedure, has a respiratory infection, is infected with influenza virus or is on a respirator. For example, the patient can have a bacterial or viral respiratory infection, such as an infection associated with human respiratory syncytial virus (RSV), influenza virua, parainfluenza virus, rhinovirus or adenovirus.

In still a further aspect the patient has a *Staphylococcus* infection, which includes but is not limited to pneumonia, sepsis, bacteremia, corneal infection, skin infection, infection of the central nervous system, or toxic shock syndrome.

In certain aspects the methods can further comprise the step of monitoring the patient for a Staphylococcal and/or Streptococcal infection within a week of administering the metalloprotease inhibitor.

Methods can also include identifying an agent that inhibits *staphylococcus* infection comprising administering a metalloprotease inhibitor to an animal infected with *staphylococcus* or animal to be infected with *staphylococcus*, evaluating the effect of administration of the metalloprotease inhibitor on the survival of the animal or staphylococcal load, and selecting an agent that increases survival of the animal or decreases staphylococcal load in the animal. In certain aspects the agent is an antibody, antibody fragment, polypeptide, peptide or a small molecule. The method can further comprise screening a plurality of agents for metalloprotease inhibitor activity and identifying an agent having a metalloprotease inhibitor activity. In certain aspects the metalloprotease inhibitor is an ADAM inhibitor.

Methods can also include identifying an agent that inhibits *streptococcus*, infection comprising administering a metalloprotease inhibitor to an animal infected with *streptococcus* or animal to be infected with *streptococcus*, evaluating the effect of administration of the metalloprotease inhibitor on the survival of the animal or streptococcal load, and selecting an agent that increases survival of the animal or decreases streptococcal load in the animal. In certain aspects the agent is an antibody, antibody fragment, polypeptide, peptide or a small molecule. The method can further comprise screening a plurality of agents for metalloprotease inhibitor activity and identifying an agent having a metalloprotease inhibitor activity. In certain aspects the metalloprotease inhibitor is an ADAM inhibitor.

Any embodiments discussed in the context of *Staphylococcus* infection can be implemented with *Streptococcus* infection, as well as infection with *Clostridium, Streptococcus, Listeria, Bacillus,* or *Arcanobacterium*. This includes, but is not limited to, infection by a specific species of these bacteria, such as *Streptococcus intermedius, Streptococcus pyogenes, Clostridium septicum,* and *Listeria monocytogenes*.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The term "anti-infective" when used in the claims and/or specification includes an agent capable of acting against infection, by inhibiting the spread of an infectious agent or by killing the infectious agent outright. Anti-infective is a general term that encompasses antibacterials, antibiotics, antifungals, antiprotozoans and antivirals.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 18A-18B. Hla-mediated E-cadherin cleavage on bronchial epithelial cells is inhibited by the ADAM10-specific inhibitor GI254023X. (A) Surface expression of ADAM10 on 16HBE14o-cells, detected by flow cytometric analysis. (B) Time and concentration dependence of Hla-mediated cytotoxicity in 16HBE14o-cells.

FIGS. 19A-19B. GI254023X prevents Hla-induced lung epithelial barrier disruption in vivo through a host-directed mechanism. (A) BAL fluid analysis for total cell count (left) and protein exudation (right) in C57BL/6J mice (n=5) treated with either DMSO or GI254023X four hours following intranasal instillation of 0.4 micrograms Hla. * denotes P<0.05 (B) Hla-induced rabbit red cell hemolysis recorded as OD450 of supernatants following red cell or Hla treatment with DMSO vehicle or GI254023X.

FIGS. 20A-20C. Role of *S. aureus* a-hemolysin in lethal infection and endothelial barrier disruption. (A) BALB/c mice (n=10) were inoculated with wild-type (WT) or toxin deficient (Hla-) *S. aureus* Newman (1×10$^8$ CFU, upper panel) and USA300/LAC (2.5×10$^7$ CFU, lower panel) via retroorbital intravenous route and observed for acute lethal disease. (B) Human pulmonary artery endothelial cells (HPAECs) transfected with either irrelevant (irr) or ADAM10-specific siRNA (A10) were treated with 150 nM purified Hla or Hla$_{H35L}$ and cell-associated metalloprotease activity was measured using a fluorogenic substrate assay. (C) HPAECs were treated with the indicated concentrations of purified Hla or with PBS or Hla$_{H35L}$ mutant, and barrier resistance was continuously measured utilizing an electric cell-substrate impedance sensing (ECIS) system.

FIG. 21. BALB/c mice treated with 200 mg/kg GI254023X/day or DMSO control were examined following intravenous injection of *S. aureus* strain Newman to evaluate lethal disease progression (n=18).

DETAILED DESCRIPTION OF THE INVENTION

Figure 1:
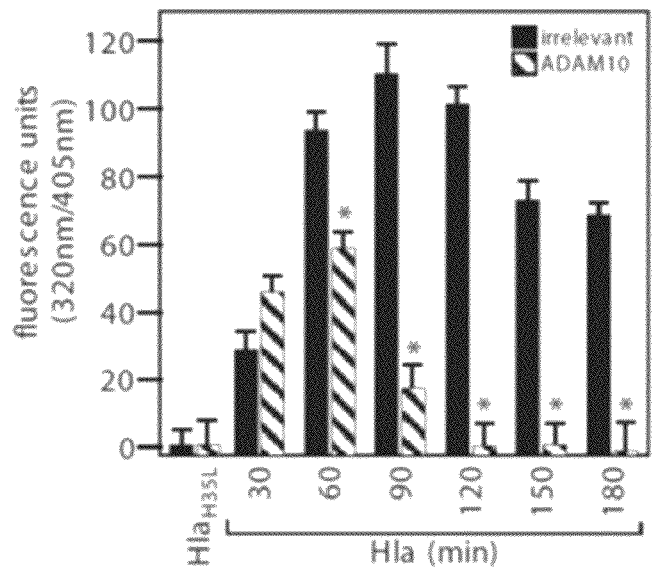
FIG. 1. S. aureus Hla causes cellular metalloprotease-dependent cleavage of E-cadherin. Hla treatment of A549 alveolar epithelial cells stimulates cell-associated metalloprotease activity. Cells transfected with irrelevant (in) or ADAM10 siRNA were treated with 10 micrograms/ml (300 nM) active Hla or the non-toxigenic mutant $Hla_{H35L}$, and cell-associated metalloprotease activity assessed with a methyl-coumarin derivitized fluorescent substrate.

Epithelial and endothelial barriers are a potent host defense against invasive bacterial infection. Pathogens circumvent this barrier through virulence factors that target specific structural elements of the epithelium, impairing its integrity (Kim et al., 2010a). Critical bacterial targets within the epithelium include focal adhesion complexes, apical tight junction proteins, and the cadherin:catenin protein complex that comprises the adherens junction. Staphylococcus aureus is a leading cause of bacteremia, pneumonia, skin and soft tissue infection and lethal toxin-mediated syndromes (Lowy et al., 1998). This organism exhibits a dual interaction with its human host, existing as a harmless skin commensal and deadly invasive pathogen armed with multiple virulence factors. S. aureus alpha-hemolysin (Hla) is a pore-forming cytotoxin that contributes to the pathogenesis of pneumonia, skin infection, and corneal infection (O'Callaghan et al., 1997; Kennedy et al., 2010; Bubeck Wardenburg et al., 2007a, 2007b). Further, Hla potentiates the penetration of S. aureus toxic shock syndrome toxin across the vaginal epithelium (Brosnahan et al., 2009). Pore-forming cytotoxins (PFTs) are a large family of secreted bacterial virulence factors characterized by their ability to assemble into multimeric, membrane-perforating complexes that cause eukaryotic cell injury and death (Gonzalez et al., 2008, which is hereby incorporated by reference). Other than bacteria, many organisms, such as cnidarians, mushrooms, plants, sea anemones and earthworms, also produce PFTs (Gonzalez et al., 2008, Iacovache et al., 2008). PFTs are secreted by the pathogens in a water-soluble form. Once secreted, PFTs diffuse towards their target cell and bind to the target cell via a specific receptor, usually with high affinity. After binding, PFTs often multimerizes into an amphipathic structure that finally inserts in the target cell membrane and forms a pore (Gonzalez et al., 2008).

There are two major types of PFTs, α-PFTs and β-PFTs. α-PFTs insert into the lipid bilayer of the target cell as α-helices. α-PFTs family includes, but not limited to, pore-forming colilcins secreted by Escherichia coli, the translocation domain of Diphtheria toxin, mammalian anti-apoptotic protein Bc12, Cry toxins from Bacillus thuringiensis. β-PFTs contain a high percentage of β-structure, and cross the membrane as β-barrels. β-PFTs family includes, for example, aerolysin from Aeromonas hydrophila, α-toxin from Staphylococcus aureus, cholesterol-dependant cytolysins (CDCs) (Gonzalez et al., 2008).

Among these PFTs, aerolysin is a representative toxin that forms small pores. Aerolysin is secreted by various species of the genus Aeromonas. A homologue of aerolysin, α-toxin, is produced by Clostridium septicum. Both aerolysin and α-toxin homologue are secreted as inactive protoxins, which are activated by proteolytic cleavage and bind to GPI anchored membrane proteins at the target cell surface. α-toxin from S. aureus is another small pore forming PFT (Gonzalez et al., 2008). CDCs are a large family of pore-forming toxins that are produced by more than 20 members from 24 different Gram-positive bacterial species, such as Clostridium, Streptococcus, Listeria, Bacillus, and Arcanobacterium (Gonzalez et al., 2008, Tweten, 2005). For example, CDCs family include Streptolysin O (SLO) from Streptococcus pyogenes, Listeriolysin O (LLO) from Listeria monocytogenes, Pneumolysin O (PLY) from Streptococcus pneumoniae, and Perferingolysin O (PFO) from Clostridium perfringens (Gonzalez et al., 2008). CDCs are characterized by absolute dependence on the presence of membrane cholesterol and the formation of large pores (Tweten, 2005).

Staphylococcus aureus encodes multiple PFTs, the most prominent and well-studied of which is α-hemolysin (Hla) (Tomita and Kamio, 1997). Hla is essential for the pathogenesis of diseases involving epithelial cell-lined interfaces, including pneumonia, dermonecrotic skin infection, corneal infection, and toxic shock syndrome (O'Callaghan et al., 1997; Kennedy et al., 2010; Bubeck Wardenburg et al., 2007a; Bubeck Wardenburg et al., 2007b; Brosnahan et al., 2009). Cellular injury induced by Hla has been attributed to its ability to form a heptameric structure, creating a central 1-2 nm pore structure that penetrates the eukaryotic lipid bilayer (Song et al., 1996). Mutant forms of the toxin that fail to form a stable oligomeric pore are non-toxigenic (Walker and Bayley, 1995; Jursch et al., 1994; Menzies and Kernodle, 1994). Treatment of cells or animals with β-cyclodextrin compounds that structurally interfere with pore function also abrogate toxicity (Karginov et al., 2007; Ragle, 2010). The identification of ADAM10 as a cellular receptor for Hla provides an opportunity to elucidate the role of the receptor in disease and define the mechanisms by which the toxin causes cell injury.

Hla utilizes A Disintegrin and Metalloprotease 10 (ADAM10) as a cellular receptor (Wilke and Bubeck Wardenburg, 2010). Zinc-dependent catalysis by ADAM10 mediates proteolytic cleavage of a number of ectodomain-containing proteins including E-cadherin (Reiss and Saftig, 2009; Maretzky et al., 2005). The homotypic interaction of E-cadherin molecules between neighboring cells provides tensile strength to the epithelium at the adherens junction (Shapiro and Weis, 2009). Surprisingly, Hla induces or stimulates the enzymatic activity of ADAM10 that leads to the direct proteolytic cleavage of the extracellular domain of E-cadherin, releasing the N-terminal ectodomain and thereby destroying the E-cadherin-dependent linkage between adjacent cells. Thus, ADAM10 is more than just a receptor for Hla, it also contributes to Hla related pathology. The profile of Hla-dependent *S. aureus* diseases strongly suggests that this toxin is a principal mediator of staphylococcal injury to the epithelium. It is contemplated that Hla upregulates ADAM10 metalloprotease activity upon binding, leading to enhanced E-cadherin cleavage.

To assess whether Hla binding alters cellular metalloprotease activity, and more specifically ADAM10-dependent activity, a fluorogenic peptide cleavage assay was performed on A549 alveolar epithelial cells treated with a subcytolytic concentration (10 micrograms/ml, ~300 nM) of active Hla. Hla induced cell-associated metalloprotease activity in cells treated with irrelevant siRNA (FIG. 1, bars). This activity required toxin oligomerization, as the non-oligomerizing $Hla_{H35L}$ mutant (Menzies and Kernodle, 1994) was incapable of eliciting this response (FIG. 1). ADAM10 siRNA treated cells exhibited toxin-induced metalloprotease activity comparable to irrelevant siRNA transfected cells at 30 minutes (FIG. 1; hatched bars), becoming blunted by 60 minutes and declining to baseline by 120 minutes. The initial rise in cell-associated metalloprotease activity in ADAM10 siRNA treated cells may result from residual ADAM10 expression observed in these cells following knockdown (Wilke and Bubeck Wardenburg, 2010), or alternatively, other cellular metalloproteases.

To examine whether toxin-induced metalloprotease activity resulted in E-cadherin cleavage, A549 cells were treated with 20 micrograms/ml active toxin over a 3 hour time course. Cell lysates were examined for the presence E-cadherin by immunoprecipitation and immunoblotting using an antibody directed against the C-terminal cytoplasmic domain of the protein. ADAM10 cleavage of E-cadherin releases the N-terminal extracellular domain from the cell, leading to a reduction in full-length (FL) protein and the appearance of a membrane-tethered, intracellular C-terminal fragment (CTF1) (Maretzky et al., 2005). The CTF is further processed by cellular proteases yielding smaller fragments (CTF2 and CTF3). Ionomycin potently induces the metalloprotease activity of ADAM10 (Murphy, 2009), stimulating E-cadherin cleavage when compared to treatment with the DMSO vehicle or the $Hla_{H35L}$ mutant. E-cadherin cleavage is evident as early as 15 minutes following Hla treatment, with further accumulation of the CTFs upon longer exposure to the toxin. Treatment of A549 cells with the peptidomimetic hydroxamate inhibitor TAPI-1, a zinc-dependent metalloprotease inhibitor, impaired Hla-induced E-cadherin cleavage as evidenced by the reduced accumulation of cleavage fragments detected by Western blot analysis, in contrast to the rapid detection of CTFs in cells treated with the DMSO vehicle and Hla. Immunofluorescense microscopy performed on cells treated with active Hla confirmed the loss of E-cadherin from the cell surface when non-permeabilized cells were stained with an antibody recognizing the extracellular domain of the protein. TAPI-1 mediated metalloprotease inhibition preserved surface expression of E-cadherin.

Having shown that Hla causes metalloprotease-dependent E-cadherin cleavage, the requirement for ADAM10 in this process was examined. A549 cells were transfected with irrelevant or ADAM10-specific siRNA, cultured in the presence of Hla for 3 hours, and E-cadherin cleavage was assessed. E-cadherin CTFs were generated in irrelevant siRNA-transfected control cells treated with ionomycin or Hla, however, E-cadherin CTFs were not evident when ADAM10 siRNA treated cells were cocultured with toxin. The preservation of E-cadherin surface expression following toxin treatment in ADAM10 knockdown cells was also evident by immunofluorescense microscopy.

Figure 2:
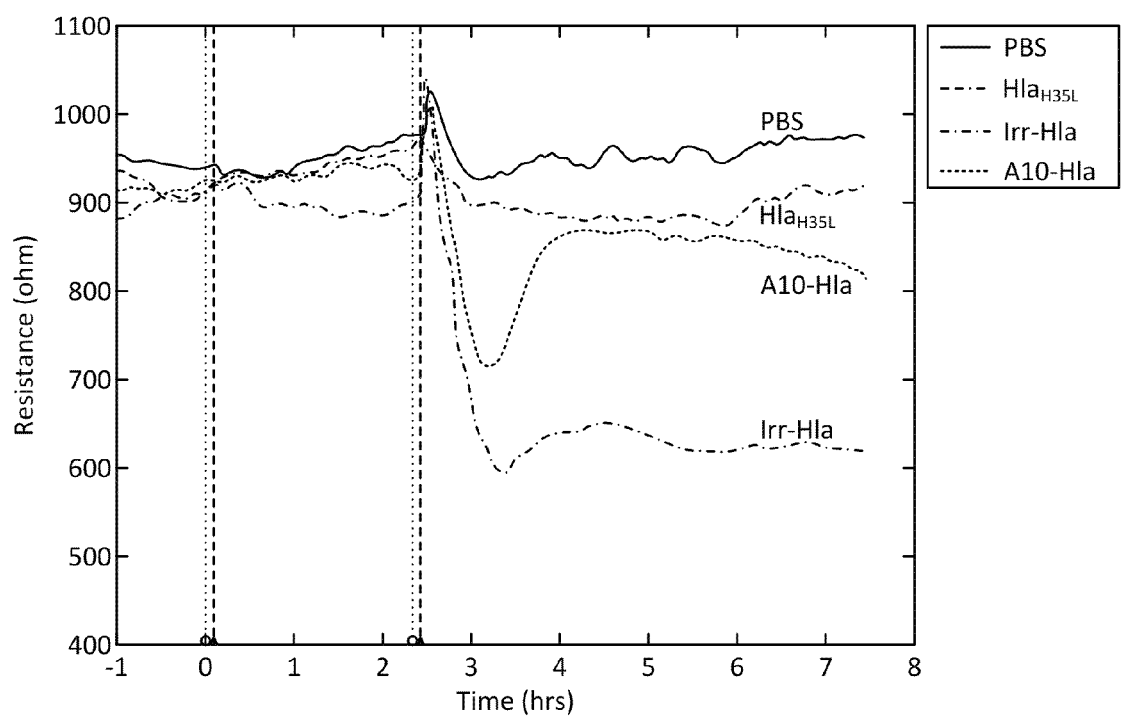
FIG. 2. ADAM10 is required for Hla-induced E-cadherin cleavage. Hla leads to ADAM10-dependent loss of epithelial monolayer resistance. Electrical cell-substrate impedance sensing (ECIS) was utilized to monitor resistance of A549 monolayers of control cells treated with PBS or the $Hla_{H35L}$ mutant (50 micrograms/ml), or irrelevant (irr) and ADAM10 (A10) siRNA transfectants treated with Hla.

E-cadherin containing adherens junctions play an integral role in the formation and maintenance of epithelial barriers (Gumbiner, 1996). It was contemplated that toxin-dependent E-cadherin cleavage may result in a physiologic disturbance of this barrier. Electrical cell-substrate impedance sensing (ECIS) was therefore utilized to record toxin-induced changes in the resistance of a confluent A549 monolayer. Following the addition of Hla to cells transfected with irrelevant siRNA, monolayer resistance declined dramatically over 1 hour (FIG. 2). Loss of the resistive barrier requires ADAM10 expression, as siRNA-mediated knockdown of ADAM10 leads to preservation of barrier function following a transient decline in resistance, likely attributable to incomplete knockdown of ADAM10. Neither control PBS nor the non-toxigenic $Hla_{H35L}$ mutant impacted cellular resistance.

Figures 3A, 3B:
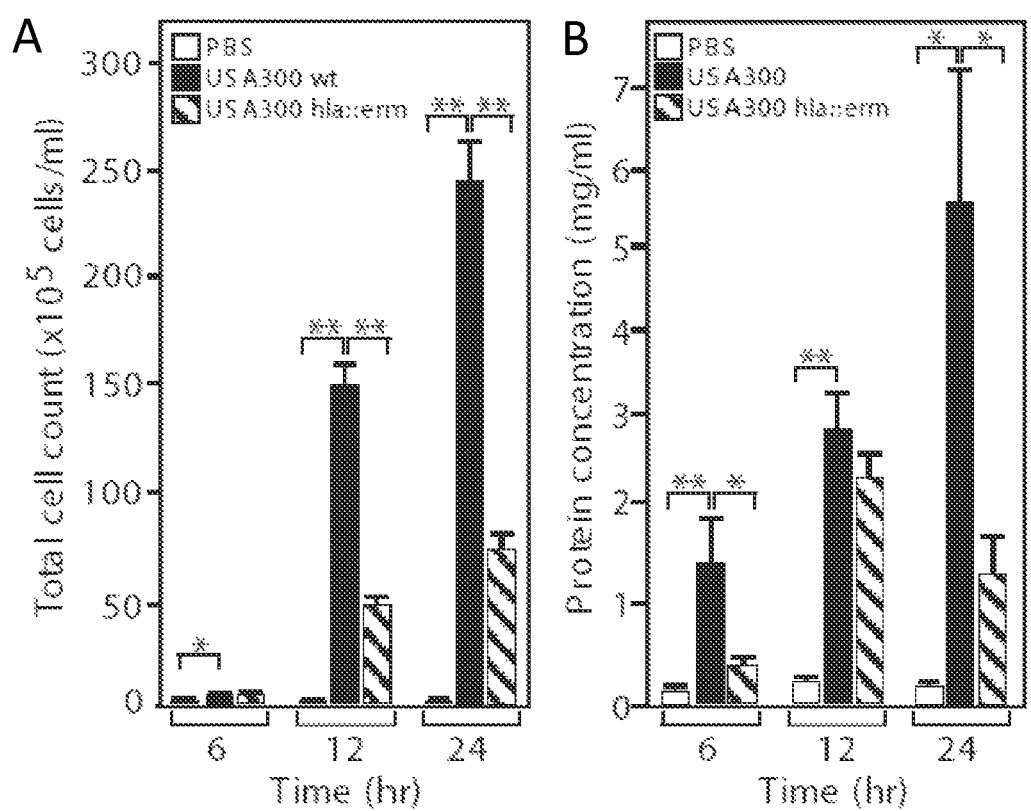
FIGS. 3A-3B. Hla is required for E-cadherin cleavage and disruption of lung epithelial barrier function in S. aureus pneumonia. 7 week old C57B1/6J mice were infected via intranasal route with $2-3\times10^8$ S. aureus USA300 or its isogenic mutant harboring an insertional disruption of the hla locus (USA300 hla::erm). Simultaneous assessments of barrier disruption were made assessing bronchoalveolar lavage (BAL) samples for total cell count (A) and protein concentration (B) in groups of 5 animals each following the instillation of 1 ml PBS into the lung. Statistical analysis was performed with the two-tailed Student's t-test where * denotes $p<0.05$ and ** denotes $p<0.01$.

Acute lung injury caused by infectious and other inflammatory stimuli is associated with a breach of epithelial and endothelial barrier function, with resultant influx of cells and proteinaceous fluid into the alveolar space (Matthay and Zemans, 2010). To examine whether E-cadherin cleavage resulted from *S. aureus* lung infection, animals were infected with live wild-type *S. aureus* strain USA300/LAC or its isogenic mutant harboring a transposon insertion in the hla locus, precluding Hla expression (USA300 hla::erm) (Bubeck Wardenburg et al., 2007b). At 6, 12 and 24 hours post-inoculation, bronchoalveolar lavage (BAL) was performed to gather evidence for E-cadherin cleavage as measured by the presence of the released N-terminal extracellular fragment (NTF). The E-cadherin NTF was immunoprecipitated from the BAL fluid using an antibody directed against the extracellular portion of the protein, followed by detection by immunoblotting. PBS treatment led to minimal detection of the E-cadherin NTF in BAL fluid, in contrast to infection with USA300, after which the NTF was detectable at 6 hours, increasing at both 12 and 24 hours. Infection with an Hla-deficient strain, USA300 hla::erm, also led to minimal detection of the NTF as seen in PBS controls. Cellular influx into the alveolar space was measured by cell count analysis in BAL fluid. Evidence for barrier disruption was seen following infection with USA300, which resulted in a dramatic increase in the total cell counts by 12 hours, further increasing by 24 hours post-infection (FIG. 3A). A blunt increase in cellular infiltrate was evident in USA hla::erm infected mice (FIG. 3A). Protein content in the BAL fluid was simultaneously examined, revealing protein accumulation in the BAL fluid as early as 6 hours in USA300 infected animals, rising through the 24 hour timepoint (FIG. 3B). An initial increase in the protein content of the BAL fluid was seen at 6 and 12 hours post-infection with USA300 hla::erm, which was equivalent to the increase observed after wild-type infection at 12 hours (FIG. 3B). The total protein in the BAL fluid elicited by the mutant strain decreased, however, by 24 hours.

Figures 4A, 4B, 4C, 4D:
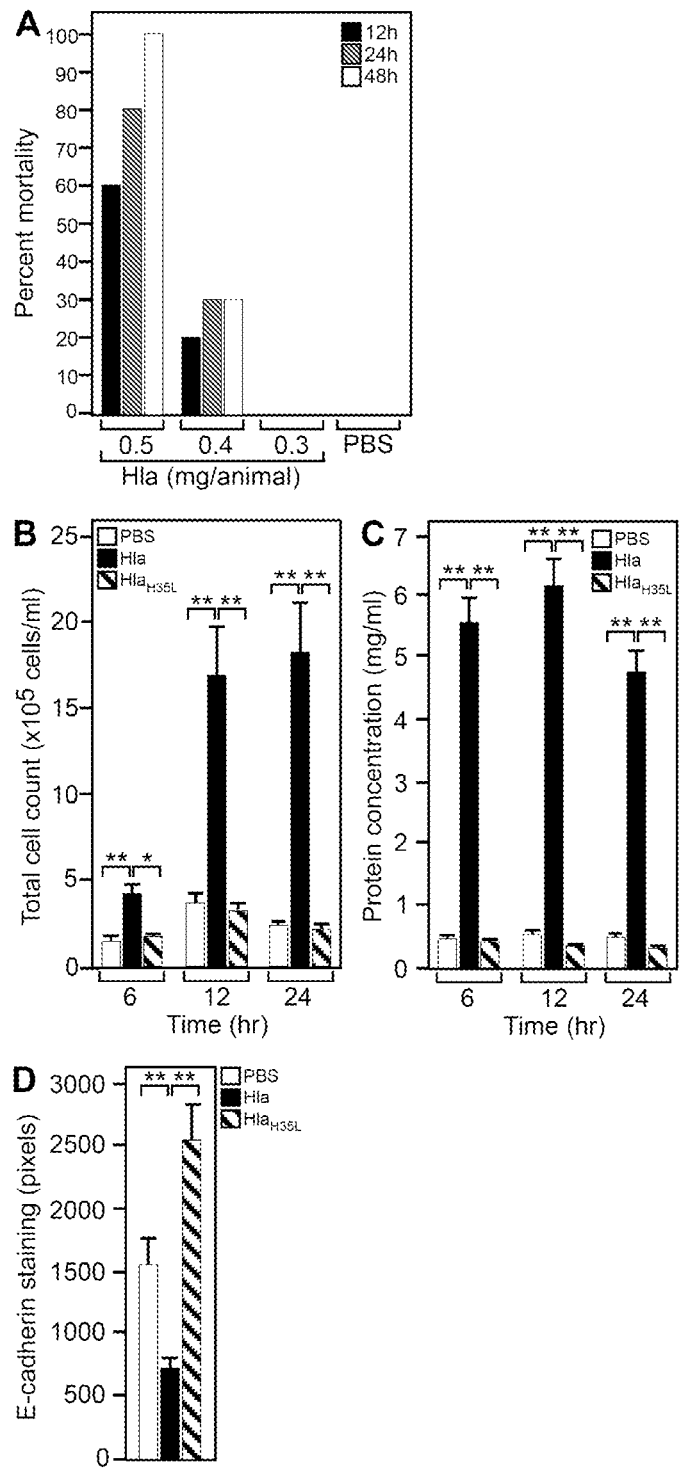
FIGS. 4A-4D. Hla is sufficient for E-cadherin cleavage and disruption of lung epithelial barrier function in S. aureus pneumonia. 7 week old C57B1/6J mice received varying intranasal dose of purified, endotoxin-free Hla, nontoxigenic $Hla_{H35L}$, or control PBS and mortality was measured over a 48 hr period (A). For panels (B), (C) and (D), 7 week old C57B1/6J mice received an intranasal dose of 0.4 micrograms purified, endotoxin-free Hla, nontoxigenic $H_{laH35L}$, or control PBS and BAL samples were analyzed at 6, 12, and 24 hours for total cell count (B), protein concentration (C) and E-cadherin immunofluorescence.

To examine the sufficiency of Hla in eliciting E-cadherin cleavage in the mouse lung, purified Hla, active Hla or a non-toxigenic mutant form of the toxin, $Hla_{H35L}$, were delivered to mice via intranasal route. Active Hla treatment resulted in a severe disease process in which 100% of mice receiving 0.5 micrograms of toxin succumbed to injury within 48 hours (FIG. 4A). A lesser degree of mortality was observed with 0.4 micrograms toxin administration; delivery of doses lower than 0.4 micrograms was not associated with mortality. Mice were treated with 0.4 micrograms active Hla or the Hla$_{H35L}$ mutant toxin, and E-cadherin cleavage in BAL samples was measured. Hla exposure led to the rapid detection of the E-cadherin NTF in BAL fluid, consistently observed at all timepoints examined. In contrast, NTF detection in the mice treated with the PBS control or Hla$_{H35L}$ was minimal. Total cell counts in BAL fluid from Hla-treated mice increased over the 24 hour time course, most notably at 12 and 24 hours (FIG. 4B). A prominent increase in the alveolar protein exudate was observed following treatment with purified Hla as early as 6 hours, consistent with the kinetics of E-cadherin cleavage product detection (FIG. 4C). Notably, the protein content of BAL fluid in mice treated with Hla$_{H35L}$ did not increase, suggesting that protein accumulation in the first 12 hours following live infection with the USA300 hla:: erm mutant is attributable to a general inflammatory process caused by the presence of live microorganisms in the lung. The loss of pulmonary E-cadherin expression following Hla treatment was evident by immunohistochemical analysis, in which staining was markedly reduced in the toxin-treated mice. Quantification of E-cadherin expression in lung tissue was performed using an Automated Cell Imaging System (ACIS), confirming these findings (FIG. 4D). Hematoxylin and eosin (H+E) staining of the corresponding lung tissue samples demonstrated the accumulation of proteinaceous exudates in the alveolar space of toxin-treated animals, consistent with BAL protein quantification. Hla is sufficient to induce E-cadherin cleavage in diverse epithelia. 7 week old C57B1/6J mice received an intranasal dose of 0.4 micrograms purified, endotoxin-free Hla, nontoxigenic Hla$_{H35L}$, or control PBS and BAL samples were analyzed at 6, 12, and 24 hours as described for the presence of the N-terminal E-cadherin cleavage fragment (NTF). Histopathologic assessment of murine lung tissues or porcine vaginal tissues treated with active Hla or control PBS. Murine lung tissues derived from animals treated with 0.4 micrograms active Hla or porcine vaginal tissues treated ex vivo with active Hla for 1 hour (120 micrograms/ml) were fixed in neutral buffered formalin, sectioned, and analyzed by hematoxylin and eosin staining or E-cadherin immunohistochemistry.

E-cadherin is ubiquitously expressed on diverse epithelial surfaces, raising the possibility that other Hla-mediated pathogenic processes also require the specific action of the toxin to cleave this substrate through ADAM10. Hla potentiates the penetration of toxic-shock syndrome toxin-1 (TSST-1) across the vaginal epithelium, allowing this toxin to enter the deeper tissues and contribute to lethal systemic disease (Brosnahan et al., 2009). ADAM10 is expressed on vaginal epithelial cells, suggesting that Hla-induced E-cadherin cleavage may provide the molecular mechanism for TSST-1 mucosal entry. Hla treatment induced a nearly complete loss of E-cadherin from the vaginal mucosa as assessed by immunohistochemical analysis; this occurred in the apparent absence of overt cytopathic injury to the surface epithelium.

Having shown that Hla induces the disruption of epithelial barriers in an ADAM10-dependent manner, the role of ADAM10 in Hla induced disruption of endothelial barriers was examined. In the endothelium, vascular endothelial (VE) cadherin is a transmembrane protein that is a part of the adherens junction network of proteins. Due to the lack of tight junctions, the adherens junction in the endothelium is responsible for the ability of endothelial cells to form a barrier between the bloodstream and the adjacent tissue. The N-terminal, extracellular portion of VE-cadheren forms homotypic interactions with VE-cadheren proteins of neighboring cells, linking adjacent cells together. The C-terminal portion binds intracellularly to other adherens junction proteins, most commonly the catenins, which bind the actin cytoskeleton maintaining cell integrity and structure. Similarly to E-cadherin, zinc-dependent catalysis by ADAM10 mediates proteolytic cleavage of VE-cadherin and it is contemplated that Hla upregulates ADAM10 metalloprotease activity upon binding, leading to enhanced VE-cadherin cleavage.

Figure 5A:
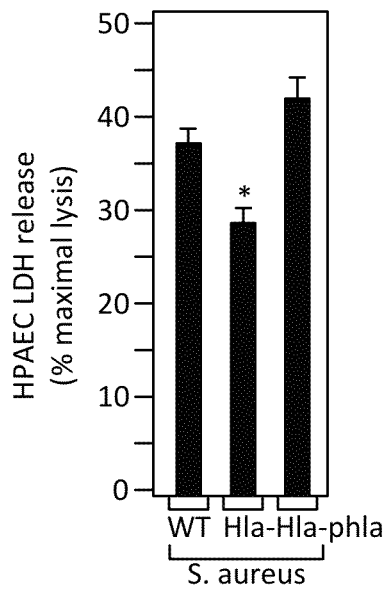
FIGS. 5A-5D. Effect of alpha toxin on endothelial cells. (A) Human pulmonary artery endothelial cells (HPAEC) infected with WT S. aureus strain Newman, Newman lacking alpha toxin (Hla-) and Newman with alpha-toxin complemented on a high copy plasmid (Hla-phla). HPAEC and bacteria were incubated for 4 hours and cell death measured by LDH release. (B) Treatment of irrelevant or ADAM10 specific siRNA transfected HPAECs with increasing concentrations of purified, active Hla for 4 hours. HPAEC death measured by LDH release. (C) HPAECs were treated with 5 micrograms/mL Hla, and the metalloprotease activity was measured using a metalloprotease specific fluorogenic substrate, the fluorescence of which was monitored at the excitation and emission wavelengths of 320 and 405 nm, respectively. (D) Measurement of metalloprotease activity in HPAECs transfected with irrelevant or ADAM10 specific siRNA. In all cases,*denotes $P<0.05$.
Figure 5B:
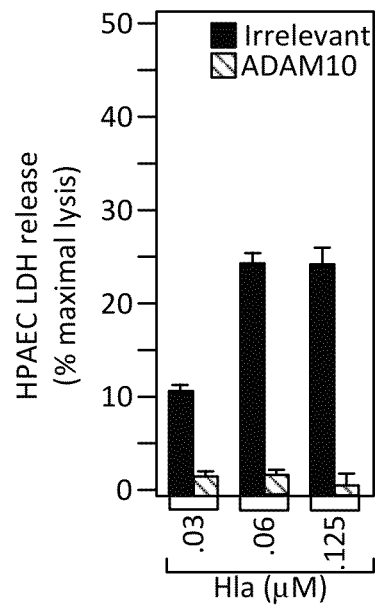

To assess whether Hla exhibits cytotoxic activity against endothelial cells and, more specifically, the role of ADAM10 in this activity, Hla-induced LDH release was used to monitor cell death in human pulmonary artery endothelial (HPAEC) cells. Treatment of HPAECs with S. aureus strain Newman for 4 hours resulted in the lysis of 37% of the HPAEC cells (FIG. 5A). To determine the role of Hla in the observed HPAEC cell lysis, HPAEC cells were treated with a S. aureus Newman strain in which the gene encoding Hla was disrupted (Hla-) or an Hla deficient strain harboring a high copy plasmid expressing Hla (Hla-pHla). Treatment with the Hla deficient strain resulted in 20% less HPAEC cell lysis as measured by LDH release than treatment with an isogenic wild type strain while treatment with the S. aureus Hla deficient strain harboring an Hla plasmid resulted in an increase in HPAEC cell lysis (FIG. 5A). In addition, treatment with increasing concentrations of purified active Hla resulted in a dose dependent lysis of HPAEC cells. The knockdown of ADAM10 expression using a specific siRNA resulted in the abrogation of LDH release after 4 hour toxin treatment as compared to HPAECs transfected with irrelevant siRNA demonstrating the integral role of ADAM10 in Hla-mediated endothelial cell lysis (FIG. 5B).

Figure 5C:
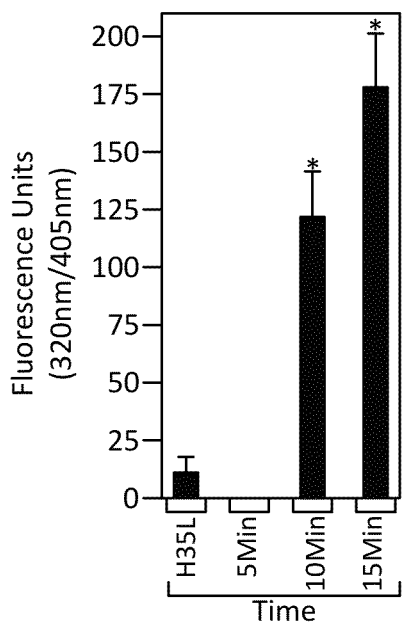
Figure 5D:
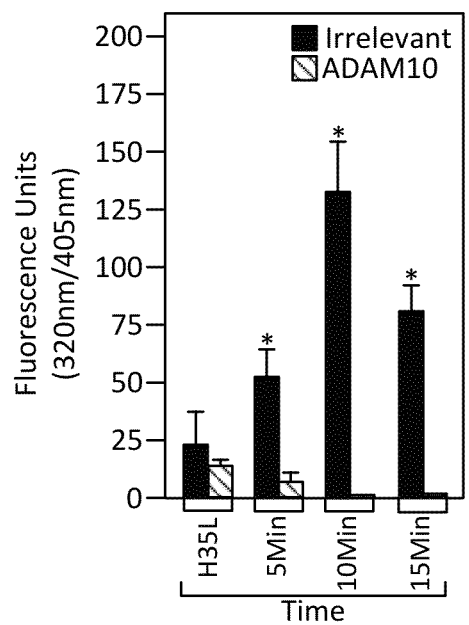

To assess the ability of Hla to stimulate ADAM10 metalloprotease activity in endothelial cells, HPAECs were treated with Hla or Hla$_{H35L}$, a mutant capable of binding to cells but lacking the ability to form the heptameric pore complex. After treatment, a metalloprotease specific fluorogenic substrate was added and fluorescence was monitored. Treatment with Hla resulted in a time dependent increase in metalloprotease activity in contrast to treatment with the H35L mutant, which did not induce an increase in metalloprotease activity (FIG. 5C). This metalloprotease activity was ADAM10 specific as the knockdown of ADAM10 expression using siRNA abrogated the ability of Hla to induce metalloprotease activity (FIG. 5D).

Based on the observation that Hla stimulates ADAM10 activity in endothelial cells, the cleavage of VE-cadherin, a known substrate of ADAM10, in response to Hla treatment was tested. To monitor Hla-induced cleavage of VE-cadherin, Human Umbilical Vein Endothelial (HUVEC) cells were treated with purified Hla from 5 min to 1 hr. Immunoprecipitation of VE-cadherin using a C-terminal specific antibody demonstrated a time dependent decrease in full length (FL) VE-cadherin. This decrease in full length VE-cadherin levels was not observed when HUVEC cells were treated with Hla$_{H35L}$ for 1 hr. A hallmark of ADAM10 dependent cleavage of VE-cadherin is the formation of a ~35kD C-terminal fragment (CTF) that is released from the cell membrane and processed. In cells treated with purified Hla, the loss of FL VE-cadherin was accompanied by the appearance of a CTF band indicating that the loss of VE-cadherin was a result of ADAM10 dependent cleavage. As a second method of monitoring the loss of VE-cadherin, confocal immunofluorescence microscopy was performed utilizing a C-terminal specific antibody to bind VE-cadherin. In addition, visualization of β-catenin, another protein involved in the maintenance of the adherins junction and which binds to the C-terminus of VE-cadherin was performed. Treatment with purified Hla for up to 30 minutes resulted in loss of VE-cadherin and β-catenin from the membrane with a concomitant increase in punctate intracellular staining. This intracellular staining is indicative of the processing of the C-terminal fragment of VE-cadherin and β-catenin, which have been shown in previous studies to be processed simultaneously upon metalloprotease dependent cleavage. Loss of VE-cadherin and β-catenin on the cell surface was also accompanied by a loss of cell-cell contacts and an increase in cell rounding, as would be expected as VE-cadherin is the major protein responsible for maintenance of the adherens junctions.

Figure 6:
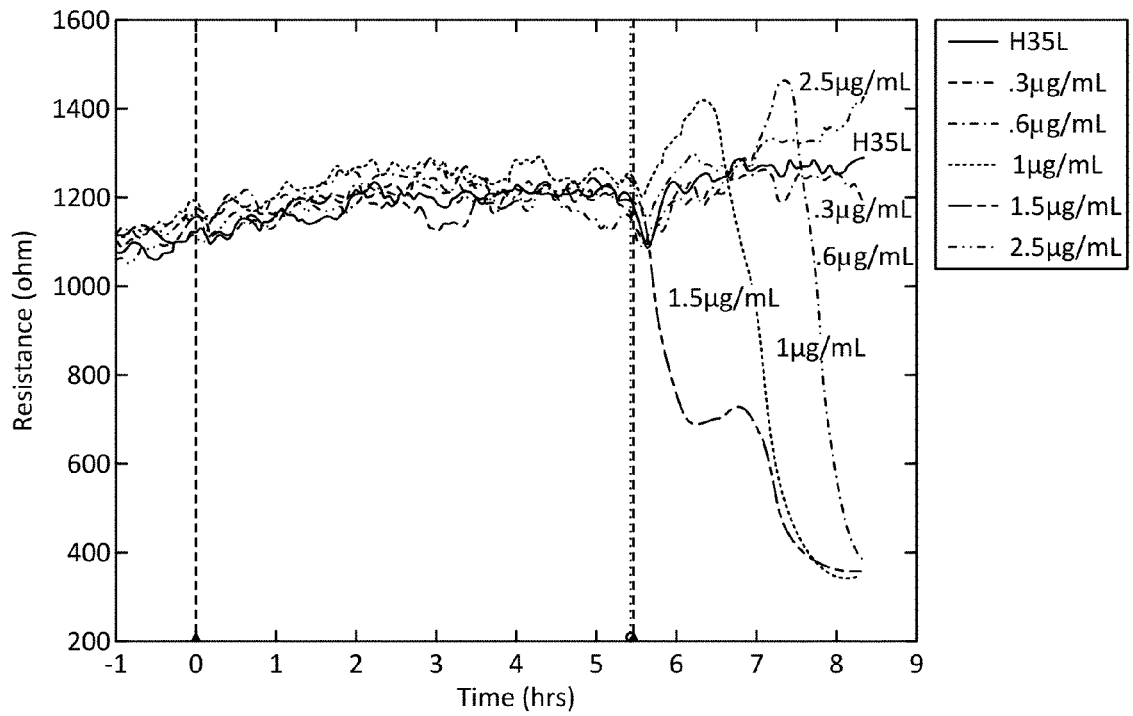
FIG. 6. Alpha-hemolysin results in the loss of endothelial barrier in HPAECs. HPAECs treated with up to 2.5 micrograms/mL Hla and barrier resistance was measured utilizing an endothelial cell substrate impedance sensing (ECIS) system.

The endothelium is an integral part of the innate immune response whose barrier capabilities must be overcome in order for bacterial pathogens to disseminate through the host. To monitor the role of Hla in endothelial barrier disruption, an endothelial cell substrate impedance sensing (ECIS) system was used to measure transendothelial electrical resistance (TEER). HPAEC cells were plated in wells containing a gold film electrode and allowed to grow to confluency. Cells that have formed a monolayer restrict the current that is flowing through the gold electrode resulting in an increase in cellular resistance. HPAEC cells that had formed a barrier were then treated with varying levels of purified Hla or Hla$_{H35L}$ and changes in resistance were monitored. Hla resulted in a complete loss of barrier function as measured by a decrease in cellular resistance in a dose dependent manner (FIG. 6). Cells that were treated with the mutant form of toxin, Hla$_{H35L}$, retained electrical resistance over the course of the experiment.

Figure 7:
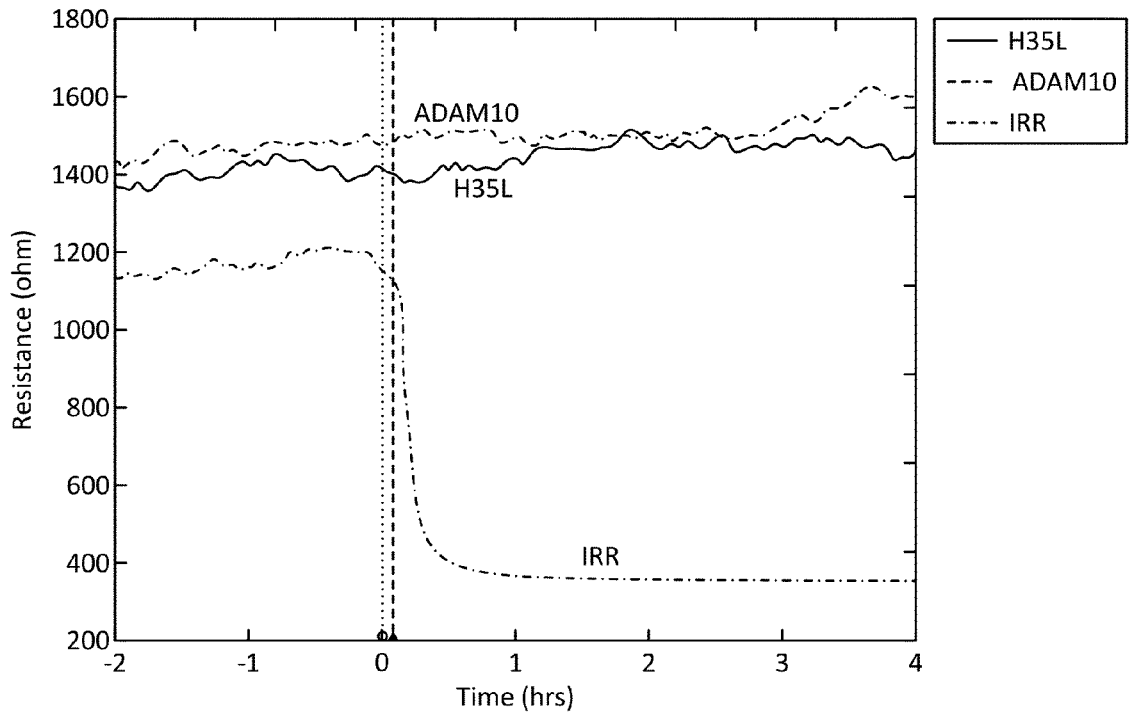
FIG. 7. Alpha-hemolysin results in the loss of endothelial barrier in HPAECs in an ADAM10 dependent manner. HPAECs transfected with siRNA treated with 2.5 micrograms/mL Hla and barrier resistance was measured utilizing an endothelial cell substrate impedance sensing (ECIS) system.

To examine whether Hla-mediated effects are dependent on ADAM10, ADAM10 was knocked down in HPAEC cells using an ADAM10 specific siRNA as described above. Transfection with siRNA resulted in complete loss of expression of ADAM10 as determined by flow cytometric analysis. Immunoprecipitation of VE-cadherin in HPAEC cells treated with Hla showed that knockdown of ADAM10 resulted in the inability of Hla to induce the cleavage VE-cadherin. Immunofluorescence microscopy using cells transfected with ADAM10 siRNA and treated with Hla demonstrated that VE-cadherin and β-catenin remained on the cell surface, cell-cell contacts remained intact and no accumulation of VE-cadherin and β-catenin punctate intracellular staining occurred. Finally, ECIS experiments demonstrated that ADAM10 knockdown resulted in the inability of Hla to induce the disruption of endothelial barrier function as no decrement in resistance was observed after Hla treatment (FIG. 7). In all assays, cells that were transfected with irrelevant siRNA showed the same sensitivity to Hla treatment as untransfected HPAEC cells.

Figure 8:
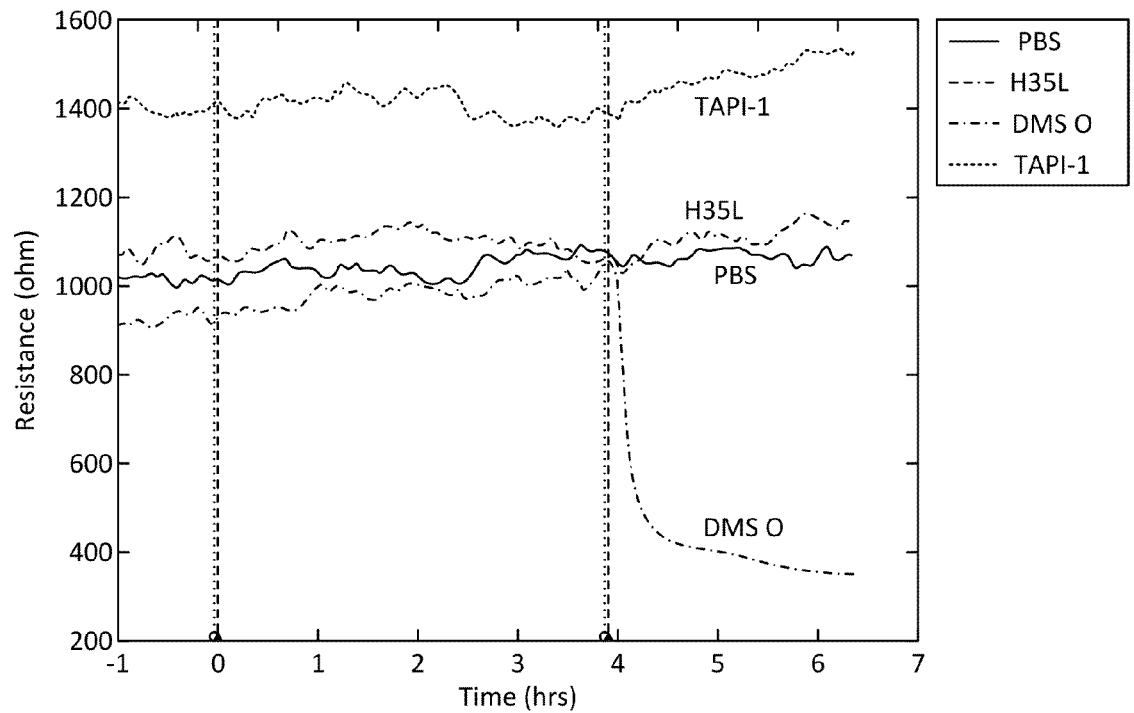
FIG. 8. HPAECs pre-incubated overnight with 20 micromolar TAPI-1 and treated with up to 2.5 micrograms/mL Hla and barrier resistance was measured utilizing an endothelial cell substrate impedance sensing (ECIS) system. Pre-treatment with TAPI-1 or treatment with the H35L mutant, which does not induce an increase in metalloprotease activity, or PBS did not result in loss of barrier function, as measured by a decrease in cellular resistance. In contrast, treatment with DMSO did result in a decrease in cellular resistance.
Figure 9:
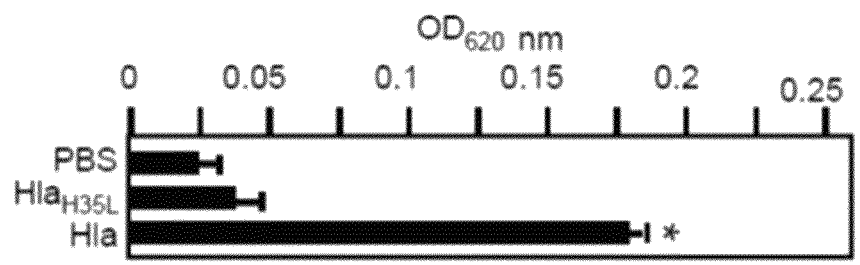
FIG. 9. Hla mediated barrier disruption in vivo as measured by Miles Assay. BALB/c mice were injected subcutaneously with 1 micrograms purified Hla followed 3 hours later by retro orbital intravenous injection of 2% Evans Blue dye. Dye extravasation measure by extraction in 100% formamide at 95° C. Mice were also treated with $Hla_{H35L}$ mutant, which does not induce an increase in metalloprotease activity, and PBS.
Figure 10:
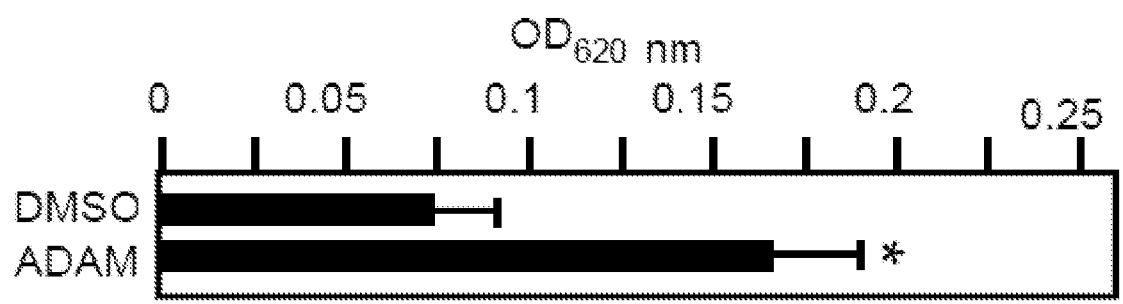
FIG. 10. BALB/c mice were treated with 2 mg/day of the ADAM10 specific inhibitor GI254023X (labeled ADAM) for 4 days or with DMSO and Miles Assay was performed as described previously.

Having shown that Hla causes ADAM10-dependent VE-cadherin cleavage, the ability of a metalloprotease specific inhibitor to prevent Hla-induced disruption of endothelial barrier function was examined. HPAEC cells were pretreated with the peptidomimetic inhibitor TAPI-1 and subjected to previously presented biochemical, immunofluorescence and ECIS assays. Virtually identically to the experiments in which ADAM10 was knocked down, pretreatment with TAPI-1 prevented VE-cadherin cleavage as shown by Western blot analysis, immunofluorescence and the maintenance of barrier function as measured by ECIS (FIG. 8). This is in contrast to the DMSO control in which sensitivity to toxin treatment is not affected.

Septic infection is accompanied by widespread vascular permeability, which leads to severe inflammation, tissue edema, and often death. In light of the Hla-induced VE-cadherin cleavage observed above, the ability of Hla to induce vascular leakage was measured in vivo. Mice were injected subcutaneously with purified, endotoxin-free Hla, nontoxigenic Hla$_{H35L}$, or control PBS and 3 hours later 2% Evans Blue dye was administered by intravenous injection. Extravasation of Evans blue dye from the vascular space into the tissues at the site of injection was visualized. Hla resulted in severe vascular leakage at the injection site, while no leakage occurred with the non-toxigenic Hla$_{H35L}$ mutant or PBS control.

A. TREATMENT METHODS

Methods of the present invention include treatments for a disease or condition caused by a pathogen, for example, a *staphylococcus* or *streptococcus* pathogen, that stimulates or induces metalloprotease activity, in particular ADAM10 activity. A metalloprotease inhibitor can be given to treat a person infected with or exposed to *staphylococcus* or suspected of having been exposed to *staphylococcus* or at risk of developing a *Staphylococcus* infection. A metalloprotease inhibitor can also be given to treat a person infected with or exposed to *streptococcus* or suspected of having been exposed to *streptococcus* or at risk of developing a *Streptococcus* infection. Methods may be employed with respect to individuals who have tested positive for exposure to *staphylococcus* or *streptococcus* or who are deemed to be at risk for infection based on possible exposure.

In particular, embodiments concern methods of treatment for staphylococcal infection, particularly infections associated with the loss of endothelial or epithelial barrier function. These infections include, but are not limited to pneumonia, sepsis, corneal infections, respiratory infections, skin infections, sinus infections, infections of the central nervous system, or toxic shock syndrome. *Staphylococcus* infections of the skin that can be treated using the methods and compositions of the invention include, but are not limited to, dermonecrotic skin infections, eczema, secondary infections associated with eczema (including atopic dermatitis), impetigo, ecthyma, cellulitis, folliculitis, psoriasis, boils (furuncles and carbuncles) and sycosis.

In some embodiments, the treatment is administered in conjunction with *Staphylococcus* antigens or antibodies that bind *Staphylococcus* bacteria and/or their proteins and/or carbohydrates. Furthermore, in some examples, treatment comprises administration of other agents commonly used against bacterial infection, such as one or more antibiotics.

The compositions and related methods of the present invention, particularly administration of a metalloprotease inhibitor, may also be used in combination with the administration of traditional therapies. These include, but are not limited to, the administration of vaccines; anti-bacterial antibodies; or antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a metalloprotease inhibitor therapy is used in conjunction with other antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the metalloprotease inhibitor is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the compositions of the present invention to a patient/subject will follow general protocols for the administration of such compounds, taking into account the toxicity, if any, of the composition, or other compositions described herein. It is expected that the treatment cycles would be repeated as necessary. It also is contemplated that various standard therapies, such as hydration, may be applied in combination with the described therapy.

B. METALLOPROTEASE INHIBITORS

Metalloproteases (also called metalloproteinases) are a superfamily of proteinases (enzymes) classified into families and subfamilies as described, for example, in Hooper (1994). Examples of metalloproteases include the matrix metalloproteases (MMPs) such as the collagenases (MMP1, MMP8, MMP13), the gelatinases (MMP2, MMP9), the stromelysins (MMP3, MMP10, MMP 11), matrilysin (MMPI), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteases such as aggrecanase, the endothelin converting enzyme family and the angiotensin converting enzyme family.

Collectively, the metalloproteases are known to cleave a broad range of matrix substrates such as collagen, proteoglycan and fibronectin. Metalloproteases are implicated in the processing, or secretion, of biological important cell mediators, such as tumor necrosis factor (TNF); and the post translational proteolysis processing, or shedding, of biologically important membrane proteins, such as the low affinity IgE receptor CD23 (see, e.g., Hooper et al., 1997).

Members of the ADAM family are cell surface proteins with a unique structure possessing both potential adhesion and protease domains. Sheddase, a generic name for the ADAM metalloprotease, functions primarily to cleave membrane proteins at the cellular surface. Once cleaved, the sheddases release soluble ectodomains with an altered localization and function.

Although a single ADAM metalloprotease may "shed" a variety of substances, multiple proteases can cleave the same substrate resulting in different consequences. ADAM10 (EC#: 3.4.24.81) is a sheddase, and has a broad specificity for peptide hydrolysis reactions. Data on the ADAM10 shedding of the ephrin/eph complex associated with Eph on one cell surface has determined that ADAM10 cleaves ephrin within the ephrin/eph complex formed between two cell surfaces. When ephrin is freed from the opposing cell, the entire ephrin/eph complex is endocytosed. This shedding in trans had not been previously shown, but may well be involved in other shedding events.

The disintegrin and cysteine-rich domain of ADAM10 play an essential role in regulation of protease activity in vivo. Recent experimental evidence suggests that this region, which is distinct from the active site, may be responsible for substrate specificity of the enzyme. This domain binds to particular regions of the enzyme's substrate, allowing peptide bond hydrolysis to occur in well defined locations on certain substrate proteins. Thus, a polypeptide, peptide, or small molecule that binds and blocks either the active site or the substrate binding site would inhibit ADAM10 activity or function.

The proposed active site of ADAM10 has been identified by sequence analysis, and is identical to enzymes in the Snake Venom metalloprotein domain family. The consensus sequence for catalytically active ADAM proteins is HEXGHNLGXXHD (SEQ ID NO 5). Structural analysis of ADAM17, which has the same active site sequence as ADAM10, suggests that the three histidines in this sequence bind a $Zn^2$ ion, and that the glutamate is the catalytic residue.

The ADAM10 active site is homologous to those of well studied zinc-proteases such as carboxypeptidase A and thermolysin. It follows that ADAM10 utilizes a similar mechanism as these enzymes. In zinc proteases, the key catalytic elements have been identified as a glutamate residue and a $Zn^{2+}$ ion coordinated to histidine residues.

ADAM10 inhibitors include compounds, polypeptides, peptides, nucleic acids or ligands, including pharmaceutically acceptable salts thereof, that inhibit the production or function of the ADAM10 enzyme. In certain aspects an inhibitor reduces or inhibits the metalloprotease activity of ADAM10. ADAM10 inhibitors include INCB7839 (trastuzumab, Incyte Co.), INCB3619; XL784; XL081; XL781; (Exelixis), and GI254023X (Roche Molecular Biochemicals, described in Schulte et al., 2007 and U.S. Pat. Nos. 6,172,064, 6,191,150, and 6,329,400, each of which is incorporated herein by reference). Other metalloprotease inhibitors (MPIs) include, but are not limited to GW280264X (hydroxyamate-based ADAM10/ADAM17 inhibitor), ABT518 (Abbott Laboratories), Neovastat (AEterna Zentaris Inc.), Psovascar (AEterna Zentaris Inc.), BAY129566 (tanomastat, Bayer Ag), batimastat, DAl25 (Dong-A Pharmaceutical), AG3340 (F. Hoffmann-La Roche Ltd), nephrostat (Galderma SA), metastat (incyclinide, Galderma SA), ISV 120 (InSite Vision Incorporated), ISV615 (InSite Vision Incorporated), BB2516 (Merck & Co Inc), TA2516 (Mitsubishi Tanabe Pharma Corporation), BB2516 (*Vernalis* plc), AG3340 (F. Hoffmann-La Roche Ltd or Pfizer Inc.), ALTY0501 (Alacrity Biosciences, Inc.), PCK3145 (Ambrilia Biopharma Inc.), SPHR913 (Sinclair Pharma plc), RAV18 (MacroGenics Inc.), ALCH1005 (AngioLab, Inc.), ALSL1023 (AngioLab, Inc.), ObX DF (inulin fiber, AngioLab, Inc.), Recombinant HSA-TIMP-2 (AngioLab, Inc.), TIMP2 ANGIOLAB (AngioLab, Inc.), AZD1236 (AstraZeneca Plc), BMS275291 (Bristol-Myers Squibb Company), D1927 (Bristol-Myers Squibb Company), CTS1027 (Conatus Pharmaceuticals Inc.), DAC:MMPI (ConjuChem Inc.), CPA926 (Daiichi Sankyo Company, Limited), Galardin (Daiichi Sankyo Company, Limited), DX2400 (Dyax Corp), Vasosten (Human Genome Sciences Inc), PerioNx (Interleukin Genetics Inc), BB3644 (Merck & Co Inc), BB2827 (Merck & Co Inc), MMI270 (Novartis AG), ON04817 (Ono Pharmaceutical Co., Ltd.), AG3433 (Pfizer Inc), TMI005 (Pfizer Inc), PG116800 (Procter & Gamble Company), PG530742 (Procter & Gamble Company), CR3294 (Rottapharm SpA), 53304 (Shionogi & Co., Ltd.), 53536 (Shionogi & Co., Ltd.), INN01137 (Tetragenex Pharmaceuticals, Inc.), INN01147 (Tetragenex Pharmaceuticals, Inc.), CDP845 (UCB S.A.), CT1166 (UCB S.A.), CT1746

(UCB S.A.), D9120 (UCB S.A.), PG116800 (Warner Chilcott Limited), PG530742 (Warner Chilcott Limited), trocade (F. Hoffmann-La Roche Ltd), WY48989 (Pfizer Inc), PUP1 (Abiogen Pharma S.p.A.), MMP Protease Inhibitor JIANGSU (Jiangsu Hengrui Medicine Co., Ltd.), V85546 (Merck Serono S.A.), MMP-13 Inhibitor AMGEN (Amgen Inc.), CR074 (Amgen Inc.), CP471358 (Pfizer Inc), and DAl25 (Dong-A Pharmaceutical), (R)—N4-Hydroxy-N1-[(S)-2-(1H-indol-3-yl)-1-methylcarbamoyl-ethyl]-2-isobutyl-succinamide; 1,10-Phenanthroline monohydrate; 4-Aminobenzoyl-Gly-Pro-D-Leu-D-Ala hydroxamic acid (FN-439); a2-Macroglobulin from human plasma (a2-M); 3-[[1-[(2-(Hydroxymethyl)-1-pyrrolidinyl)carbonyl]-2-methylpropyl]carbamoyl]octanohydroxamic acid; (N-[(2S, 3R)-3-Amino-2-hydroxy-4-phenylbutyryl]-L-leucine hydrochloride); Dichloromethylenediphosphonic acid disodium salt; Doxycycline hydrate; Ethylenediaminetetraacetic acid disodium salt dihydrate; Isoamylphosphonyl-Gly-Pro-Ala dipotassium salt; N-(Methoxysuccinyl)-Ala-Ala-Pro-Val-chloromethyl ketone (N-(Methoxysuccinyl)-L-alanyl-L-alanyl-L-prolyl-L-valine chloromethylketone); (N-($\alpha$-Rhamno-pyranosyl-phos-phono)-L-leucyl-L-tryptophan disodium salt; N-($\alpha$-Rhamno-pyranosyl-oxy-hydroxy-phosphinyl)-Leu-Trp disodium salt); Pro-Leu-Gly hydroxamate hydrochloride; Z-Pro-Leu-Gly hydroxamate; 7-Methoxycoumarin-4-acetyl-Arg-Pro-Lys-Pro-Tyr-Ala-Nva-Trp-Met-(2,4-dinitrophenyl)Lys amide; 7-Methoxycoumarin-4-acetyl-Pro-Leu-Gly-Leu-$\beta$-(2,4-dinitrophenylamino)Ala-Arg amide (7-Methoxycoumarin-4-acetyl-P-L-G-L-$\beta$-(2,4-dinitrophenylamino)A-R amide); N-(2,4-Dinitrophenyl)-Pro-Leu-Gly-Cys(Me)-His-Ala-D-Arg amide; Nobiletin (3', 4',5,6,7,8-Hexamethoxyflavone); (6S,7S)—N-Hydroxy-5-methyl-6-[(4-phenylpiperidin-1-yl)carbonyl]-5-azaspiro[2.5]octane-7-carboxamide, (6S,7S)—N-Hydroxy-5-methyl-6-[(4-phenyl-3,6-dihydropyridin-1(2H)-yl) carbonyl]-5-azaspiro[2.5]octane-7-carboxamide, (6S,7S)—N—Hydroxy-6-{[(3-phenylpyrrolidin-1-yl]carbonyl}-5-azaspiro[2.5]octane-7-carboxamide, (6S,7S)—N-Hydroxy-6-((4-(methylsulfonyl)phenyl)-3,6-d-ihydropyridin-1(2H)-yl)carbonyl)-5-azaspiro(2,5)octane-carboxamide, (2S,3S)—N-hydroxyl-1-methyl-24(10aS)-3,4,10,10a-tetrahydropyrazino (1,-2-a)indol-2(1H)-yl-carbonyl) piperidine-3-carboxamide, (6S,7S)—N-Hydroxy-6-((10aS)-3,4,10,10a-tetrahydropyrazino(1,2-a)-indol-2(1H)-yl-carbonyl)-5-azaspiro(2,5)octane-7-carboxamide, (6S,7S)—N-Hydroxy-6-((4-(3-(methylsulfonyl)phenyl)-3,6-dihydropyridin-1(2H)-yl)carbonyl)-5-azaspiro(2,5)octane-7-carboxamide, methyl (6S,7S)-7-[(hydroxyamino) carbonyl]-6-[(4-phenyl-3,6-dihydropyridin-1(2H)-yl) carbonyl]-5-azaspiro[2.5]octane-5-carboxylate, benzyl (6S, 7S)-7-[(hydroxyamino)carbonyl]-6-[(4-phenyl-3,6-dihydropyridin-1(2H)-yl)carbonyl]-5-azaspiro[2.5]octane-5-carboxylate, (6S,7S)—N-Hydroxy-5-(methylsulfonyl)-6-[(4-phenyl-3,6-dihydropyridin-1(2H)-yl)carbonyl]-5-azaspiro[2.5]octane-7-carboxamide, and (6S,7S)—N-Hydroxy-6-{[4-(3-methoxyphenyl)piperidin-1-yl]carbonyl-5-methy-1-5-azaspiro[2.5]octane-7-carboxamide. Other small molecule inhibitors of ADAM10 include N-hydroxy-1,4-disubstituted piperazine-2-carboxamides and derivatives thereof (as described in U.S. Ser. Nos. 10/518,110 and 12/605,118, "Human ADAM-10 inhibitors", which are incorporated herein by reference), any of the Aza spiro alkane derivatives described in U.S. Pat. No. 7,723,349 and U.S. patent application Ser. Nos. 12/327,313, and 13/184,860 "Aza spiro alkane derivatives as inhibitors of metalloproteases", which are incorporated herein by reference including a compound of the formula I

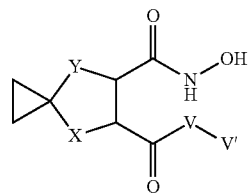

or an enantiomer, diastereomer, solvate, or pharmaceutically acceptable salt thereof, wherein: X is $CH_2NR_b$; Y is $(CH_2)_i$; V is piperidin-1-yl, piperazin-1-yl, pyrrolidin-1-yl, pyridin-1-yl or 3,6-dihydropyridin-1-yl each substituted with 0-5 $R_e$; V' is phenyl substituted with 0-5 $R_e$; $R_b$ is H, C(O)O $(CR_b'R_c')_r$-T, or $C(O)(CR_b'R_c')_r$-T; $R_b'$ and $R_c'$ are both H; $R_e$ is H, $C_{1-6}$ alkyl, OH, Cl, F, Br, I, CN, $NO_2$, methoxy, ethoxy, n-propoxy, isopropoxy, phenoxy, benzyloxy, amino, $(C_{1-4})$ alkylamino, $(C_{2-8})$ dialkylamino, $C(O)O(C_{1-4}$ alkyl), $CONH_2$, $CONH(C_{1-4}$ alkyl), $CON(C_{1-4}$ alkyl)$_2$, $C_{1-6}$ haloalkyl, phenyl, cyclopropyl, cyclobutyl, cyclopentyl, cyclohexyl, cycloheptyl, benzyl, or phenethyl; T is H, $C_{1-10}$ alkyl substituted with 0 to 5 $R_b'$; $C_{2-10}$ alkenyl substituted with 0-3 $R_b'$, or heterocyclyl substituted with 0-5 $R_b$; i is 1 or 2; and r is 0, 1 or 2.

Further MPIs useful according to the methods of the present invention include TAPI-1, BMS-275291, and CGS27023A.

Compounds that decrease expression and/or activity of ADAM10 include, but are not limited to, the compounds set forth in U.S. patent application Ser. No. 12/160,862 or U.S. Pat. Nos. 7,638,301, 8,034,783, 6,172,064, 6,329,400, and 6,191,150, each of which are incorporated herein by reference.

Further hydroxamate compounds suitable as MPIs include one or more of those referred to above as well as those described in, for example, WO 03/051825; WO 03/106381; U.S. Patent Ser. No. 60/534,501; 60/512,016; or 60/515,352, each of which is incorporated herein by reference in its entirety.

Further compounds that are suitable include a magnesium salt/complex of a compound of formula I, as further described in U.S. patent application Ser. No. 12/682,874 and U.S. Pat. Nos. 7,629,341 and 7,989,661, which are incorporated herein by reference in their entirety:

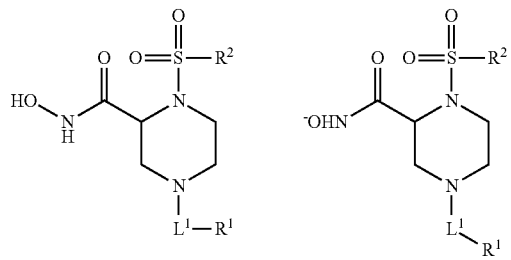

wherein $L_1$ is —C(O)—, —S(O)$_2$—, or —(CH$_2$)$_n$—; $R_1$ is —H, —OR$_{11}$, —(CH$_2$)$_n$R$_{11}$, —C(O)R$_{11}$, or —NR$_{12}$R$_{13}$; R$_{11}$, R$_{12}$, and R$_{13}$ are each independently: a) R$_{50}$; b) saturated or mono- or poly-unsaturated $C_5$-$C_{14}$-mono- or fused poly-cyclic hydrocarbyl, optionally containing one or two heteroatoms per ring, wherein the saturated or mono- or poly-unsaturated $C_5$-$C_{14}$-mono- or fused poly-cyclic hydrocarbyl is optionally substituted with one or two independently selected $R_{50}$ substituents; c) $C_1$-$C_6$-alkyl, $C_2$-$C_6$-alkenyl, $C_2$-$C_6$-alkynyl, or —C(O)H, each of which is optionally substituted with one, two or three substituents independently selected from $R_{50}$ and saturated or mono- or poly-unsaturated $C_5$-$C_{14}$-mono- or fused poly-cyclic hydrocarbyl, optionally containing one or two heteroatoms per ring and optionally substituted with one, two or three independently selected $R_{50}$ substituents; or d) $R_{12}$ and $R_{13}$, together with the N to which they are covalently bound, form a $C_5$-$C_6$ heterocycle optionally containing a second heteroatom, wherein the $C_5$-$C_6$ heterocycle is optionally substituted with one or two independently selected $R_{50}$ substituents; $R_2$ is —$R_{21}$-$L_2$-$R_{22}$; $R_{21}$ is saturated or mono-, or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents; $L_2$ is —O—, —C(O)—, —CH$_2$—, —NH—, —S(O)$_2$—, or a direct bond; $R_{22}$ is saturated or mono- or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents; and $R_{50}$ is $R_{51}$-$L_3$-(CH$_2$)$_n$—; $L_3$ is —O—, —NH—, —S(O)$_{0\text{-}2}$—, —C(O)—, —C(O)O—, —C(O)NH—, —OC(O)—, —NHC(O)—, —C$_6$H$_4$—, or a direct bond; $R_{51}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$ alkyl amino, di-$C_1$-$C_6$ alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two heteroatoms per ring, wherein $R_{51}$ is optionally substituted with one, two, or three substituents selected from the group consisting of: $C_1$-$C_6$-alkyl, halo, —CF$_3$, —OCF$_3$, —OH, —NH$_2$, mono-$C_1$-$C_6$ alkyl amino, and di-$C_1$-$C_6$ alkyl amino; and $R_{52}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$ alkyl amino, di-$C_1$-$C_6$ alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two heteroatoms per ring; and wherein n is 0, 1, 2, or 3; provided that an O or S is not singly bonded to another 0 or S in a chain of atoms.

Further compounds that are suitable include a compound and pharmaceutically acceptable salts of formula II, as further described in Chinese Patent application 102206206, which is incorporated herein by reference in its entirety:

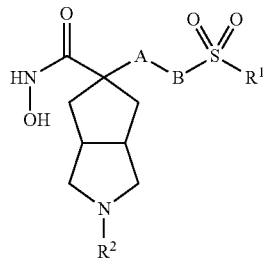

wherein A=(un)substituted (CH$_2$)$_m$, m=1 or 2; B=(NH)$_n$, n=0 or 1; R$^1$=(un)substituted alkyl, cycloalkyl, heterocyclyl, or aryl, etc.; R$^2$=H, (un)substituted alkyl, alkoxy, or aryl, etc.

Further compounds that are suitable include those described in U.S. patent application Ser. No. 10/782,679, incorporated by reference herein in its entirety. Compounds that are suitable include ADAM10 inhibitors that comprise hydroxamic acid or N-formylhydroxylamine functional groups.

In another aspect, the presently disclosed subject matter provides isolated human ADAM10 prodomain consisting of an amino acid sequence present in amino acid residues 18-212 of human ADAM10 protein, the peptide having the functionality of modulating ADAM10 protein activity. In another aspect, the presently disclosed subject matter provides isolated human ADAM10 prodomain comprising the sequence set forth in SEQ ID NOs 1-4, or a sequence having at least 95% homology to any of SEQ ID NOs 1-4 and having the functionality of modulating ADAM10 activity. In another aspect, the presently disclosed subject matter provides isolated human ADAM10 prodomain consisting of the sequence set forth in SEQ ID NOs 1-4, or a sequence having at least 95% homology to any of SEQ ID NOs 1-4 and having the functionality of modulating ADAM10 activity. U.S. patent application Ser. No. 11/897,018 is incorporated herein by reference in its entirety.

In another aspect, the presently disclosed subject matter provides a compound of structural formula III, as described in U.S. Pat. No. 7,498,358, incorporated by reference in its entirety herein,

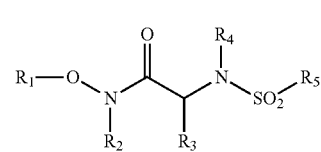

or a pharmaceutically acceptable salt thereof, wherein $R_1$ is selected from hydrogen, alkyl, alkanoyl, arylalkyl, and arylalkanoyl, wherein the arylalkyl and arylalkanoyl groups are unsubstituted or substituted with 1, 2, 3, 4, or 5 $R_6$ groups; $R_6$ at each occurrence is independently selected from halogen, hydroxy, —NO$_2$, —CO$_2$R$_{10}$, —CN, alkyl, alkoxy, haloalkyl, and haloalkoxy; $R_2$ is selected from hydrogen, alkyl, alkoxy, alkanoyl, arylalkyl and arylalkanoyl, wherein the arylalkyl and arylalkanoyl groups are unsubstituted or substituted with 1, 2, 3, 4, or 5 $R_6$ groups; $R_3$ is -Z-Q-J, wherein Z is selected from alkyl, alkoxyalkyl, alkylthioalkyl, and alkenyl, each of which is unsubstituted or substituted with 1 or 2 groups that are independently selected from alkoxy, hydroxy, and halogen; Q is selected from a direct bond between Z and J, —C(=O)—, aryl, heteroaryl, and heterocycloalkyl, wherein the aryl, heteroaryl, or heterocycloalkyl group is unsubstituted or substituted with 1 or 2 groups that are independently selected from alkyl, halogen, —NR$_8$R$_9$, and alkoxy; J is —C(=NR$_7$)NR$_8$R$_9$ or —NH—C(=NR$_7$)NR$_8$R$_9$ wherein R$_7$ is selected from H, CN, NO$_2$, alkyl, alkanoyl, arylalkanoyl and —C(=O)NR$_{10}$R$_1$1, wherein R$_{10}$ and R$_1$1 are independently selected from H, and alkyl, and R$_8$ and R$_9$ are independently selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from alkyl, alkoxy, hydroxy, and halogen; or $R_7$, $R_8$, and the nitrogens to which they are attached form a 5, 6 or 7 membered heterocycloalkyl group that is unsubstituted or substituted with 1, 2 or 3 groups that are independently selected from alkyl, alkoxy, hydroxy, and halogen; and $R_9$ is selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups; $R_4$ is selected from H, alkyl, and arylalkyl, wherein the arylalkyl group is unsubstituted or substituted with 1, 2, 3, 4, or 5 $R_6$ groups; and $R_5$ is -M-G-A, wherein M is aryl, wherein M is unsubstituted or substituted with 1, 2, 3, or 4 groups that are independently selected from halogen, alkyl, hydroxy, alkoxy, haloalkyl, —CN, haloalkoxy, and hydroxyalkyl; G is selected from a direct bond between M and A, $CH_2$, -alkyl-O—, —O-alkyl-, O, S, SO, and $SO_2$; A is aryl, wherein A is unsubstituted or substituted with 1, 2, 3, 4, or 5 groups that are independently selected from halogen, alkyl, alkoxy, haloalkyl, aryloxy, heteroaryloxy, arylalkoxy, heteroarylalkoxy, haloalkoxy, —CN, and $NO_2$; with the proviso that when M is phenyl, G is a direct bond between M and A, and A is phenyl, then at least one of the four remaining hydrogens on the phenyl ring of M, of M-G-A, must be substituted with a group independently selected from halogen, alkyl, hydroxy, alkoxy, haloalkyl, —CN, haloalkoxy, and hydroxyalkyl. MPIs suitable for use according to the methods of the present invention can be identified by any of numerous known assays testing for inhibitory activity of an ADAM.

1. General Pharmaceutical Compositions

In some embodiments, pharmaceutical compositions are administered to a subject. Different aspects of the present invention involve administering an effective amount of a composition to a subject. In some embodiments of the present invention, a composition comprising a metalloprotease inhibitor may be administered to the subject or patient to protect against or treat infection by one or more *staphylococcus* pathogens. Additionally, such compounds can be administered in combination with an antibiotic or another standard antibacterial therapy. Such compositions will generally be dissolved or dispersed in a pharmaceutically acceptable carrier or aqueous medium.

The active compounds of the present invention can be formulated for parenteral administration, e.g., formulated for injection via the intravenous, intramuscular, sub-cutaneous, or even intraperitoneal routes. The preparation of an aqueous composition that contains a compound or compounds that inhibit Hla stimulated or induced metalloprotease activity will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. In addition to the compounds formulated for parenteral administration, other pharmaceutically acceptable forms include, e.g., aerosolizable, inhalable, or instillable formulations; tablets or other solids for oral administration; time release capsules; creams; lotions; mouthwashes; and the like. The preparation of an such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

2. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject. In certain aspects of the present invention, the compositions may be administered either in vitro, ex vivo, or in vivo.

3. Antibodies and Passive Immunization

Another aspect of the invention is the administration of other therapies or vaccines in conjunction with a metalloprotease inhibitor. Methods of administering immunoglobulins directed at bacterial antigens to a recipient to prevent a staphylococcal infection can be considered a passive vaccine. Another aspect of the invention includes the use of active vaccines against staphylococcal infection in conjunction with metalloprotease inhibitors. Certain therapeutic methods include the administration of a therapeutic immunoglobulin or an antigen to stimulate or induce production of an immune response in a subject. A method of preparing an immunoglobulin for use in prevention or treatment of staphylococcal infection comprises the steps of immunizing a recipient or donor with a vaccine and isolating immunoglobulin from the recipient or donor. In certain aspect an immunoglobulin can bind to a cell surface protein, a toxin or any other component of the bacterium that is surface exposed, including, but not limited to lipoproteins and carbohydrate constituents of the bacterial cell wall. In other aspects an antibody may bind to Hla and inhibit the activation of a metalloprotease. A pharmaceutical composition comprising an immunoglobulin, with or without a metalloprotease inhibitor, and a pharmaceutically acceptable carrier can be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

The antibodies can be isolated to the extent desired by well known techniques such as affinity chromatography (Harlow and Lane, 1988). Antibodies can include antiserum preparations from a variety of commonly used animals, e.g. goats, primates, donkeys, swine, horses, guinea pigs, rats or man.

Any immunoglobulin, whether directed at ADAM10 or any bacterial antigen and produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex. In the case of an immunoglobulin directed at a metalloprotease, for example, ADAM10, the immunoglobulin may bind to the metalloprotease and inhibit its activation or activity.

A vaccine can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals, or where treatment is required and there is no time for the individual to produce antibodies in response to vaccination.

C. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

Example 1

ADAM10 knockout mice exhibit embryonic lethality at E9.5 owing to defects in development of the cardiovascular and central nervous systems and altered somitogenesis (Hartmann et al., 2002). To examine the requirement for ADAM10 in *S. aureus* pneumonia, mice harboring a deletion of ADAM10 in the intrapulmonary respiratory epithelium were created through conditional expression of Cre-recombinase under control of the surfactant protein C promoter (FIG. 15A) (Perl et al., 2002; Tian et al., 2008). Conditional knockout mice (ADAM10$^{\Delta/\Delta}$) were viable, without apparent alterations in lung architecture. Cre-dependent recombination was confirmed by PCR on alveolar epithelial cell genomic DNA harvested from control and ADAM10$^{\Delta/\Delta}$ mice, and loss of ADAM10 expression in lung tissue of knockout mice visualized by immunohistochemical staining. The survival of ADAM10$^{\Delta/\Delta}$ mice following infection with *S. aureus* was assessed relative to littermate controls, revealing resistance of the knockout animals to lethal staphylococcal pneumonia (FIG. 24). Histopathologic examination of lung tissue from ADAM10$^{\Delta/\Delta}$ mice following infection revealed limited influx of inflammatory cells into the alveolar space with preservation of alveolar structure, in contrast to severe airspace disease in control mice.

Figure 12A:
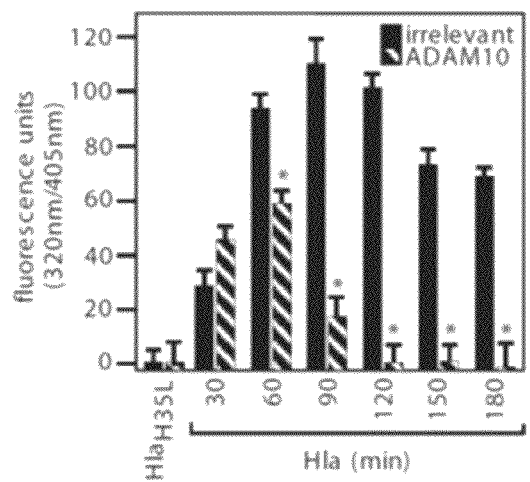
FIGS. 12A-12D. Hla induces ADAM10-dependent epithelial barrier disruption and E-cadherin cleavage. (A) Cell-associated metalloprotease activity measured in A549 cells transfected with irrelevant (In) or ADAM10 siRNA following treatment with 10 micrograms/ml (300 nM) active Hla or the non-toxigenic mutant Hla$_{H35L}$. Activity was quantified by detection of a fluorescent substrate product. (B) Electrical cell substrate impedance sensing (ECIS) recordings of A549 monolayers treated with PBS, the Hla$_{H35L}$ mutant (50 micrograms/ml), or irrelevant (Irr) and ADAM10 (A10) siRNA transfectants treated with 50 micrograms/ml Hla. (C and D) Cellular metalloprotease activity and E-cadherin cleavage induced by treatment of A549 cells with 10 micrograms/ml Hla, the monomeric Hla$_{H35L}$ mutant, a pre-pore locked mutant (Hla$_{PPL}$) that is reverted to the wild-type toxin in the presence of dithiothreitol (Hlapp$_L$+DTT), or Hla in the presence of the pore-blocking methyl-β-cyclodextrin (MβCD) (C), or by Hla in the presence of media (F12K), PBS, Dulbecco's PBS (DPBS) or PBS supplemented with 0.9 mM Ca$^{2+}$, 0.493 mM Mg$^2$ or 2.67 mM K$^+$ (D). Error bars represent SEM.
Figure 16A:
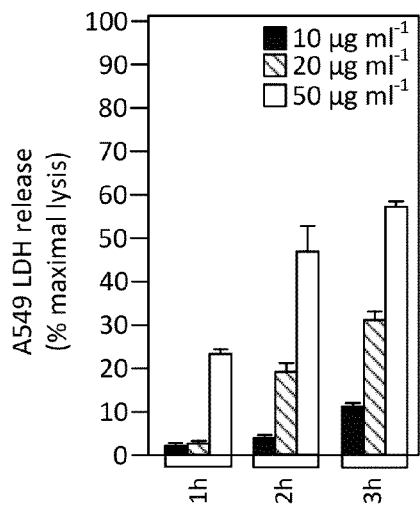
FIGS. 16A-16C. Role of ADAM10 in pore-forming toxin-mediated injury in vitro. (A) LDH release from A549 cells cultured in the presence of 10, 20, or 50 micrograms/ml active Hla for the indicated time periods. (B) siRNA-mediated knockdown of ADAM10 on A549 cells as demonstrated by flow cytometric assessment using an isotype control IgG (IgG ctl) or specific anti-human ADAM10 antibody to stain both irrelevant siRNA tranfected cells (Irr) or ADAM10 siRNA transfectants (ADAM10). (C) LDH release (upper panel) and cell-associated metalloprotease activity (lower panel) following treatment of A549 cells with the indicated concentrations of Hla (solid black bars) or pneumolysin (PLY, hatched bars).
Figure 16B:
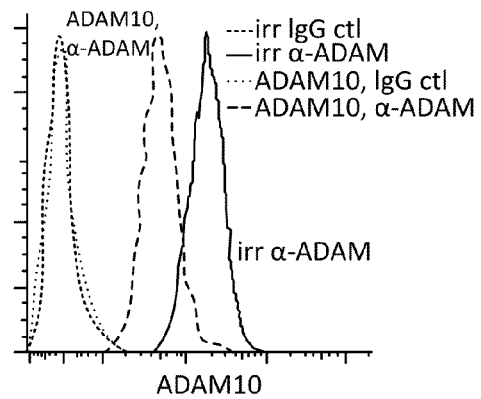

Zinc-dependent catalysis by ADAM10 results in the proteolytic cleavage of ectodomain-containing proteins that modulate epithelial cell attachment and migration, immunologic function, and cell signaling (Reiss and Saftig, 2009; Seals and Courtneidge, 2003). As epithelial barrier integrity is disrupted in *S. aureus* pneumonia, that ADAM10 enzymatic activity may contribute to toxin-mediated injury. To assess whether Hla binding alters ADAM10-dependent cellular metalloprotease activity, fluorogenic peptide cleavage assay was performed on A549 alveolar epithelial cells treated with 10 micrograms/ml active Hla (300 nM). This recombinant toxin harbors a specific activity of ~2000 hemolytic units (HU)/mg determined by previously defined methods (Bhakdi and Tranum-Jensen, 1991) causing limited cytotoxicity at concentrations 20 micrograms/ml (FIG. 16A). Hla induced metalloprotease activity in cells treated with irrelevant siRNA (FIG. 12A); a non-oligomerizing Hla$_{H35L}$ mutant (Menzies and Kernodle, 1994) was incapable of eliciting this response. ADAM10 siRNA-treated cells exhibited toxin-induced metalloprotease activity comparable to irrelevant siRNA transfected cells at 30 minutes (FIG. 12A; hatched), which became blunted by 60 minutes and declined to baseline by 120 minutes. The initial rise in metalloprotease activity in ADAM10 siRNA treated cells most likely results from residual ADAM10 expression consistently noted following knockdown (FIG. 16B and Wilke and Bubeck Wardenburg, 2010).

Figure 12B:
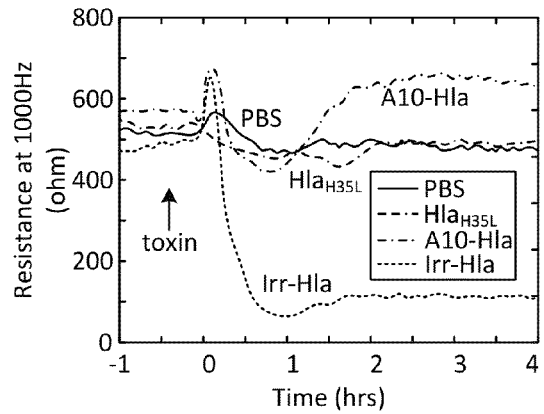

Based on the role of ADAM10 in epithelial tissue homeostasis, it was reasoned that toxin-dependent upregulation of ADAM10 activity may contribute to pathophysiologic disturbance of epithelial barrier function. Electrical cell substrate impedance sensing (ECIS) was utilized to record toxin-induced changes in electrical resistance of a confluent A549 monolayer. Following the addition of Hla to cells transfected with irrelevant siRNA, monolayer resistance declined over 1 hour (FIG. 12B). Knockdown of ADAM10 preserved barrier function, while neither PBS nor the non-toxigenic Hla$_{H35L}$ mutant impacted monolayer resistance.

Epithelial barriers provide a potent host defense against invasive bacterial infection. Pathogens circumvent this barrier through virulence factors that target structural elements of the epithelium, including focal adhesions, apical tight junctions, and the adherens junction E-cadherin-based protein complex (Kim et al., 2010). Activation of ADAM10 leads to proteolytic cleavage of the extracellular domain of E-cadherin, severing the homotypic E-cadherin linkage between adjacent cells to permit dynamic turnover and maintenance of the epithelium (Maretzky et al., 2005). B. fragilis and H. pylori impair epithelial barrier function through the secretion of metalloproteases that cleave E-cadherin in a manner similar to that of ADAM10 (Hoy et al., 2010; Wu et al., 1998). To examine whether Hla-induced ADAM10 activation resulted in E-cadherin cleavage, lysates from Hla-treated A549 cells were examined by immunoprecipitation and immunoblotting using an antibody directed against the C-terminal cytoplasmic domain of E-cadherin. ADAM10-mediated cleavage of E-cadherin releases the N-terminal extracellular domain from the cell, leading to a reduction in full-length (FL) protein and the appearance of an intracellular C-terminal fragment (CTF) (Maretzky et al., 2005). Ionomycin potently induces ADAM10 activity secondary to increased intracellular calcium concentration (Murphy, 2009), stimulating cleavage when compared to treatment with DMSO or the Hla$_{H35L}$ mutant. Cleavage was evident as early as 15 minutes following Hla treatment (20 micrograms/ml), and observed with sublytic toxin concentrations ranging from 1-50 micrograms/ml (30 nM to 1.5 micromolar) 1-hour exposure. Loss of E-cadherin via extracellular cleavage was readily visible by immunofluorescence microscopy.

Figures 13A, 13B, 13C, 13D:
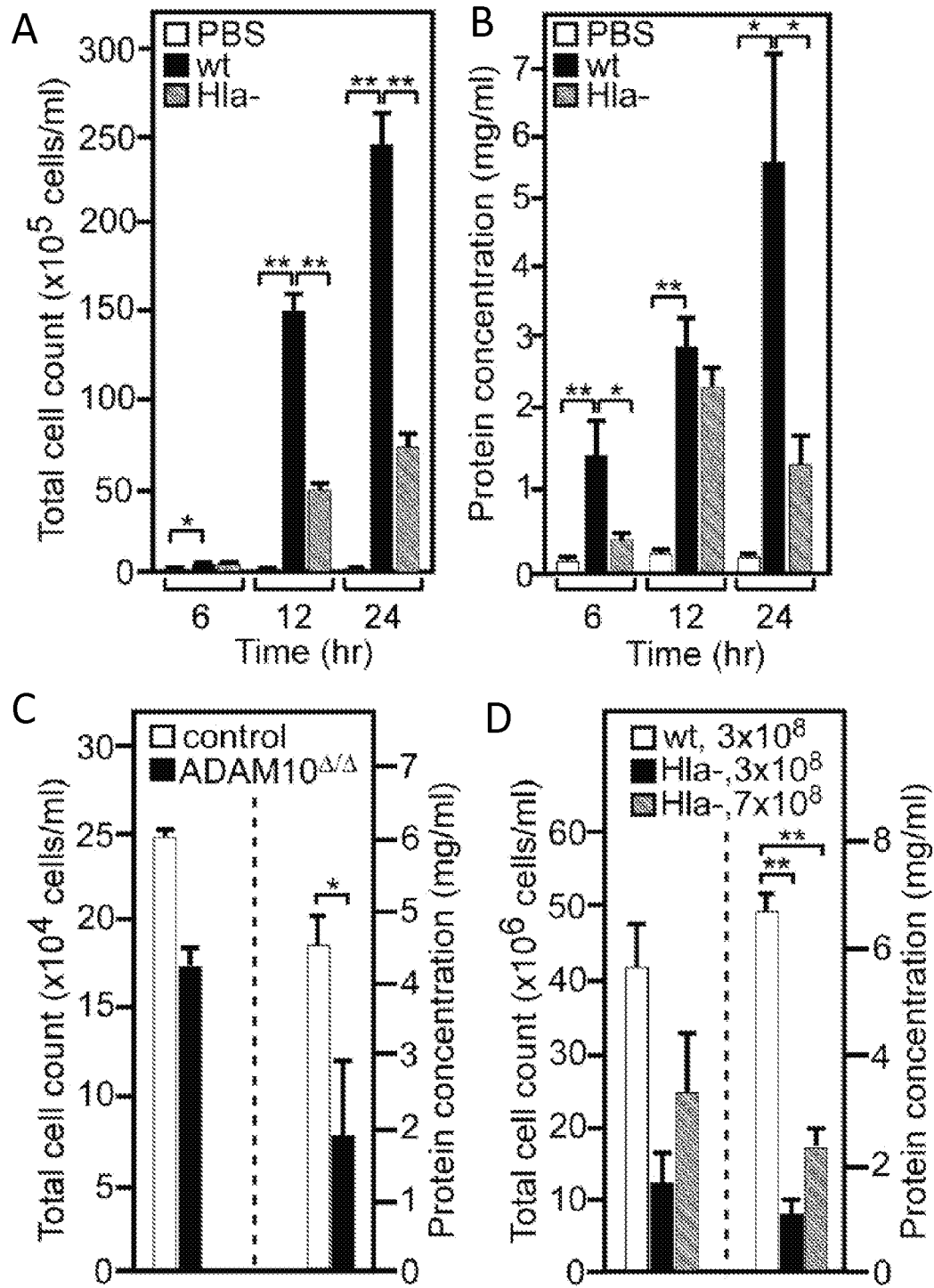
FIGS. 13A-13D. Hla is required for E-cadherin cleavage and disruption of epithelial barrier function in *S. aureus* pneumonia. Bronchoalveolar lavage (BAL) fluid analysis 6, 12, and 24 hours post-infection of C57BL/6J mice infected with *S. aureus* USA300 or its isogenic mutant harboring a disruption of the hla locus (Hla-) to assess E-cadherin cleavage. Simultaneous assessments of barrier disruption were made assessing BAL for cell count (A) and protein concentration (B) in groups of 7 animals. (C) Cell and protein content analysis in BAL fluid harvested from control and ADAM10$^{\Delta/\Delta}$ mice following treatment with 0.4 micrograms purified Hla delivered by intranasal route. (D) Cell/protein recovery from BAL samples of C57BL/6J mice infected with either 3×10$^8$ WT or Hla-*S. aureus* as compared to infection with 7×10$^8$ Hla-*S. aureus*. Statistical analysis was performed using a two-tailed Student's t-test, where * denotes P<0.05 and ** denotes P<0.02.

To examine the role of Hla in E-cadherin cleavage and epithelial barrier disruption in vivo, a murine model of S. aureus pneumonia was used. Strains that lack Hla expression are unable to cause disease in this model, while toxin neutralization protects against disease (Ragle et al., 2009; Bubeck Wardenburg and Schneewind, 2008). Acute lung injury incited by infectious and inflammatory stimuli is associated with a breach of epithelial barrier function, with influx of cells and proteinaceous fluid into the alveolar space (Matthay and Zemans, 2010). To examine E-cadherin cleavage in staphylococcal pneumonia, C57BL/6J mice were infected with wild-type (wt) S. aureus strain USA300/LAC or its isogenic mutant harboring a transposon insertion in the hla locus (hla::erm) (Bubeck Wardenburg et al., 2007a). Bronchoalveolar lavage (BAL) was performed to evaluate E-cadherin cleavage, measured by release of the N-terminal extracellular fragment (NTF). PBS treatment and infection with non-toxigenic mutant S. aureus led to minimal NTF detection, in contrast to wt infection where the NTF was detectable by 6 hours and prominent at 12 and 24 hours. Evidence for alveolar barrier disruption was observed as an increase in BAL cell counts following wt infection (FIG. 13A), a response that was blunted in hla::erm-infected mice at the 12 and 24 hour timepoints (FIG. 13A, hatched). Examination of BAL protein revealed exudation into the alveolar space by 6 hours in wt-infected animals, rising through 24 hours (FIG. 13B). Minimal protein influx was seen in hla::erm-infected mice at 6 and 24 hours, with increased protein content at 12 hours likely reflective of inflammation that occurs in response to an increasing bacterial tissue load (FIG. 13B, hatched bars) (Bubeck Wardenburg et al., 2007a; Bubeck Wardenburg et al., 2007b; Bubeck Wardenburg and Schneewind, 2008).

To examine the sufficiency of Hla in eliciting pulmonary E-cadherin cleavage, 0.4 micrograms Hla or Hla$_{H35L}$ was delivered to mice via intranasal route. Hla led to a rapid appearance of the NTF in BAL fluid. In contrast, NTF detection in PBS and Hla$_{H35L}$ treated mice was minimal. Cell counts from Hla-treated mice increased over 24 hours (FIG. 17A, left), coincident with increased alveolar protein exudate (FIG. 17A, right); these were not observed in mice treated with Hla$_{H35L}$. As early as 4 hours post toxin treatment, when signs of lung injury were minimal and indistinguishable between Hla$_{H35L}$ and active Hla treated mice, the loss of pulmonary E-cadherin expression following Hla treatment was evident by immunohistochemical analysis. Hla treatment induced minimal E-cadherin cleavage in ADAM10$^{\Delta/\Delta}$ mice as compared to littermate controls. BAL cell recovery in ADAM10$^{\Delta/\Delta}$ mice was comparable to littermate controls, while protein accumulation was significantly reduced (FIG. 13C). The requirement of ADAM10 in E-cadherin cleavage was also examined in vitro. E-cadherin CTF was generated in toxin-treated irrelevant siRNA-transfected A549 cells, however, it was not evident in ADAM10 knockdown cells. This preservation of E-cadherin surface expression was confirmed by immunofluorescence microscopy.

Figure 14A:
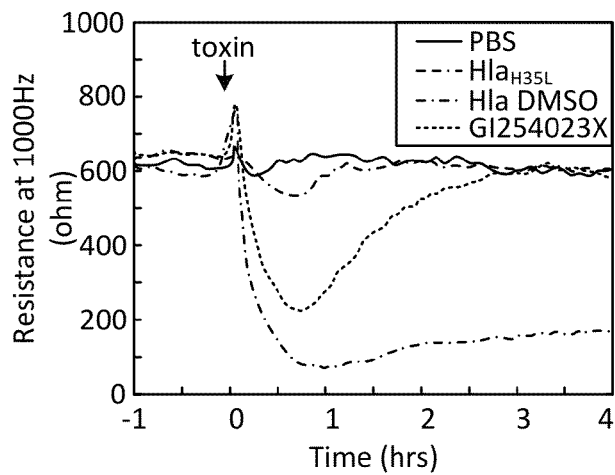
FIGS. 14A-14B. An ADAM10-specific metalloprotease inhibitor prevents Hla-mediated injury. (A) ECIS-based monitoring of A549 monolayer resistance following toxin treatment (20 micrograms/ml) of cells exposed to GI254023X (20 µM), PBS control, Hla$_{H35L}$, or Hla DMSO vehicle control. (B) Mortality curves in mice treated with DMSO vehicle or GI254023X upon challenge with lethal inocula of strain Newman (upper panel, n=14 mice, 5×10$^8$ *S. aureus* per mouse, lower panel, n=8 mice, 6.3×10$^8$ *S. aureus* per mouse).

The contribution of ADAM10 to Hla-mediated cellular injury raised the possibility that metalloprotease inhibition may mitigate toxin action. Treatment of A549 cells with the ADAM10-specific peptidomimetic hydroxamate inhibitor GI254023X nearly abrogated Hla-induced E-cadherin cleavage relative to that seen in control cells, supported by immunofluorescence microscopy examining E-cadherin-containing intercellular junctions. These findings correlated with preservation of epithelial barrier function upon toxin exposure (FIG. 14A). These findings were confirmed in the ADAM10-expressing bronchial epithelial cell line 16HBE14o-using flow cytometric analysis (FIG. 18A), which forms a polarized monolayer characterized by the assembly of apical tight and adherens junction complexes. 20 micrograms/ml active Hla was minimally cytotoxic to these cells (FIG. 18B), yet caused loss of E-cadherin expression and disruption of cell junctions that could be prevented by GI254023X. ADAM10 expression in the context of this polarized line was demonstrated at both the apical and basolateral poles, similar to findings previously reported in murine lung epithelium. GI254023X markedly impaired toxin binding and subsequent oligomerization on the surface of A549 cells.

Figure 14B:
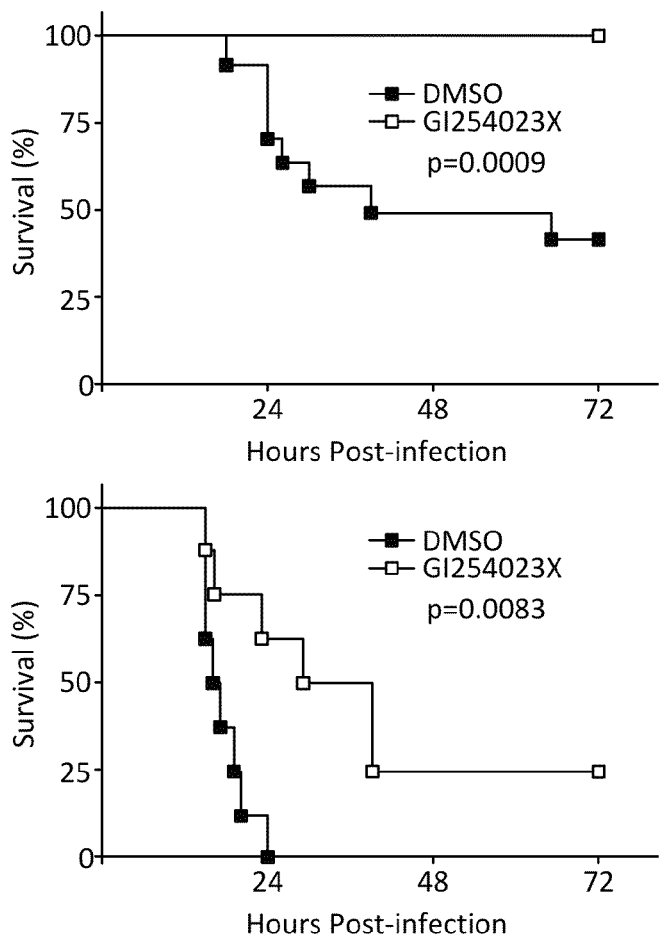

The potent mechanism by which GI254023X antagonizes Hla suggested that administration of this drug may mitigate lung injury. Treatment of mice with the ADAM10 inhibitor prevented E-cadherin cleavage in response to Hla treatment and reduced the accumulation of both cells and proteinaceous edema in the alveolar space (FIG. 19A). Mice receiving GI254023X were protected from rapidly lethal *S. aureus* pneumonia, displaying an increase in time to death and survival among some animals (FIG. 14B).

Example 2

Materials and Methods

Recombinant proteins, cell lines, antibodies and reagents. Tagged Hla and Hla$_{H35L}$ fusion proteins were prepared and purified as previously described (Wilke and Bubeck Wardenburg, 2010; Bubeck Wardenburg and Schneewind). The Hla$_{PPL}$ mutant was generated through the introduction of cysteine residues at positions 108 and 154. All recombinant preparations of wild-type Hla were standardized by assessment of the specific activity of the toxin as determined by described methods (Bhakdi and Tranum-Jensen, 1991). Active Hla utilized in this study demonstrated a specific activity of approximately 2000 hemolytic units (HU) per mg. The quantity of active toxin utilized for assays described is the following: cellular metalloprotease assays, 2 HU; ECIS, 30 HU; E-cadherin biochemical studies, 240 HU; E-cadherin immunofluoroescence studies, 8 HU; intranasal inoculation of mice with active Hla, 0.8 HU; LDH release assays, 0.7-3.5 HU. The number of hemolytic units utilized in each assay is a reflection of the intended toxin concentration, delivered in a volume adjusted proportionately to the surface area of the vessel in which cells were plated for the assay. This calculation ensures that toxin availability for cell binding is equilibrated on a cell-number basis between distinct assays. Methyl-β-cyclodextrin was purchased from Sigma and utilized at a final concentration of 10 μM.

A549 alveolar epithelial cells were cultured in F12K media supplemented with 10% fetal bovine serum and L-glutamine. 16HBE14o-bronchial epithelial cells were cultured in MEM media supplemented with 1% fetal bovine serum and L-glutamine as previously described (Illek et al., 2008).

Anti-human E-cadherin antibody directed against the C-terminal domain of the protein was purchased from BD Biosciences and used for immunoprecipitation and immunoblotting. Anti-human E-cadherin antibody for immunofluorescence microscopy was purchased from Abcam, while anti-E-cadherin antibody for mouse immunohistochemistry was purchased from Invitrogen. Anti-mouse E-cadherin ECCD-2 antibody directed against the N-terminal domain of the protein was purchased from Invitrogen. Anti-human ADAM10 antibody was purchased from R and D systems, while an anti-ADAM10 antibody used for mouse immunohistochemistry was purchased from Santa Cruz. Alexa Fluor®-conjugated secondary antibodies for detection with the LI-COR Odyssey Imaging System were purchased from Invitrogen.

The ADAM10 inhibitor GI254023X was synthesized by and purchased from OKeanos Tech., Ltd. The compound was generated according to a published synthetic path (Hoettecke et al., 2010). For in vitro studies, GI254023X was resuspended in DMSO and used at a concentration of 20 μM, applied to cells in complete media 12-16 hours prior to experimentation. For in vivo studies GI254023X was diluted in 0.1 M carbonate buffer to a 0.014 M stock, and ~200 mg kg$^{-1}$ GI254023X was delivered to mice once daily by intraperitoneal injection in a total volume of 100 μl. Drug dosing began 3-5 days prior to the delivery of purified Hla or infection with *S. aureus*, and was maintained throughout the course of observation.

Bacterial strains and culture. *S. aureus* strains Newman, USA300 and the Hla deficient USA300 strain containing a transposon insertion in the hla locus (Hla-) were described previously (Bubeck Wardenburg and Schneewind, 2008; Bubeck Wardenburg et al., 2007a; Bubeck Wardenburg et al., 2007b), these strains were propagated in tryptic soy broth (TSB).

Generation of ADAM10$^{Δ/Δ}$ conditional knockout mice. Double transgenic mice harboring the following transgenes were sued for breeding: 1) surfactant protein C (SP-C) promoter that drives expression of the reverse tetracycline transactivator (SP-C-rtTA) and 2) tetracycline operator-minimal CMV promoter-driven Cre recombinase ((tetO)$_7$CMV-Cre). This transgenic mouse model system permits conditional expression of the Cre-recombinase in intrapulmonary epithelial progenitor cells when pups are exposed to doxycycline in utero via the supply of the drug to pregnant dams. ADAM10$^{loxP/+}$ mice harboring loxP sites that flank exon 3 were purchased from Jackson Laboratories and bred to derive expand the colony of hemizygous mice and generate ADAM10$^{loxP/loxP}$ mice. SP-C-rtTA$^{tg/-}$/(tetO)$_7$CMV-Cre$^{tg/-}$ mice were bred to ADAM10$^{loxP/+}$ or ADAM10$^{loxP/loxP}$ to generate SP-C-rtTA$^{tg/-}$/(tetO)$_7$CMV-Cre$^{tg/-}$/ADAM10$^{loxP/+}$ triple transgenic mice. These mice were mated with SP-C-rtTA$^{tg/-}$/(tetO)$_7$CMV-Cre$^{tg/-}$/ADAM10$^{loxP/loxP}$ mice to generate triple transgenic mice homozygous for the ADAM10 floxed allele. When matings expected to render SP-C-rtTA$^{tg/-}$/(tetO)$_7$CMV-Cre$^{tg/-}$/ADAM10$^{loxP/loxP}$ mice were established, doxycycline was supplied in the drinking water at a concentration of 1 mg ml$^{-1}$ from E0-E14. Progeny were screened via PCR performed on genomic DNA to evaluate for the presence of the SP-C-rtTA and (tetO)$_7$CMV-Cre transgenes and to identify mice homozygous for the ADAM10 floxed allele. Screening of mice was performed as previously described (Tian et al., 2008; Perl et al., 2002). Littermate controls were derived from female mice lacking one or a combination of the SP-C-rtTA, (tetO)$_7$CMV-Cre, or ADAM10$^{loxP/loxP}$ transgenes. Documentation of excision of exon 3 in doxycycline-exposed SP-C-rtTA$^{tg/-}$/(tetO)$_7$CMV-Cre$^{tg/-}$/ADAM10$^{loxP/loxP}$ was performed on genomic DNA derived from alveolar type II (ATII) epithelial cells derived from triple transgenic mice, prepared as described previously (Rice et al., 2002).

siRNA experiments. siRNA treatment of cells was conducted as previously reported (Wilke and Bubeck Wardenburg, 2010). Briefly, 2×10$^6$ A549 cells in 0.05 ml of cold 1×PBS, pH 7.4, were electroporated with 125 picomoles of irrelevant or ADAM10 specific siRNA (Applied Biosciences) using an ECM 830 electroporator (BTX Genetronics) with a 96-well attachment. Cells were grown 48-72 hrs before being replated and used for experiments.

Metalloprotease assay. A549 cells were plated in 96 well tissue culture plates at a density of 1.5×10$^4$ cells/well 24 hours prior to experimentation. Cells were washed once in PBS then purified, active Hla, or Hla mutants (10 micrograms/ml or as specified), pneumolysin (as specified) or control PBS was added to each well in unsupplemented F12K media or specific buffers where noted for the time periods indicated. Cells were then washed once in 25 mM Tris, pH 8.0 buffer, and incubated at 37° C. with 10 micromolar fluorogenic peptide substrate (Mca-PLAQAV-Dpa-RSSSR—NH$_2$, R&D Systems) diluted in 25 mM Tris, pH 8.0. Following incubation, fluorescence intensity was read on a BioTek Synergy HT plate reader.

Preparation of toxin-treated lysates and western blotting. For detection of E-cadherin in A549 cells, 1×10$^6$ cells were plated in 10 cm tissue culture dishes 48-72 hours prior to experimentation. Cell monolayers were rinsed in PBS, then incubated with 20 micrograms/ml purified Hla or pneumolysin in F12K media or other buffers as indicated without supplements for the time periods described. Ionomycin (1 µM) or DMSO controls were added to monolayers 35 min prior to cell processing. Monolayers were then washed once with PBS and lysed in 1.8 ml lysis buffer (10 mM Tris pH 7.4, 150 mM NaCl, 1 mM EDTA, 1 mM EGTA pH 8.0, 0.5% NP-40, and 1% Triton X-100 containing protease inhibitor (Complete, Roche)). Cellular debris was pelleted by centrifugation at 13,000 rpm for 10 minutes, and clarified lysates utilized for E-cadherin immunoprecipitation with the described antibody and Protein G agarose (Thermo Scientific). Precipitates were resuspended in Laemmli buffer, heated to 90° C. for 5 min and proteins resolved on a 12% SDS-PAGE gel according to standard protocols. Immunoblotting was performed according to standard protocols, and images were obtained with a LI-COR Odyssey Imaging System for detection of Alexa Fluor® conjugated secondary antibodies.

Fluorescence microscopy and immunohistochemistry. A549 or 16HBE14o-cells were seeded onto coverslips in 24 well plates at a density of $8 \times 10^4$ 48-72 hours prior to experimentation. Cells were then treated with 20-50 micrograms ml active Hla in F12K media without supplements for the time periods indicated. After washing cells three times in PBS, the cells were fixed in 4% paraformaldehyde in PBS for 10 minutes, then incubated with PBS containing 1% bovine serum albumin for 30 minutes, washed and incubated with mouse monoclonal anti-E-cadherin recognizing the extracellular domain of the protein (1 micrograms/ml in PBS, Abcam) for 1 hour at room temperature. After washing, the cells were incubated with Alexa Fluor® 488 goat anti-mouse antibody (1:5000 dilution) for 1 hour at room temperature, washed, mounted in ProLong® Gold with DAPI (Invitrogen) and visualized using an Olympus DSU confocal microscope. Image processing and analysis of immunofluorescence microscopy was performed with ImageJ software (found on the world wide web at rsbweb.nih.gov/ij/).

Tissue specimens for immunohistochemical analysis were fixed in 10% neutral buffered formalin, paraffin embedded, sectioned, subjected to antigen retrieval, and stained for 1 hour with either anti-ADAM10 antibody (5 micrograms $ml^{-1}$) or anti-E-cadherin antibody (20 micrograms $ml^{-1}$). Secondary staining with a biotinylated anti-mouse (ADAM10) or HRP anti-rat (E-cadherin) antibody (1:100) was followed by detection using an ABC/DAB chromagen system for ADAM10 stained samples or an HRP-polymer/DAB chromagen system for E-cadherin stained samples. All sections were counterstained with hematoxylin. Visualization and image capture was performed using an Olympus FSX-100 microscope or a Zeiss Axioskop microscope (100×images only).

Epithelial cell impedance sensing studies. The effect of Hla on lung epithelial barrier function was measured with an electrical cell substrate impedance sensing system (ECIS, Applied BioPhysics). $8 \times 10^4$ A549 cells in 300 microliters complete medium were seeded in 8W10E cultureware and incubated at 37° C. in a $CO_2$ incubator. Electrical resistance of the cell layer was recorded continuously until a stable resistance of approximately 500-600 ohms was documented, signifying confluence of the monolayer.

Flow cytometry and LDH release assays. For flow cytometry, $2.5 \times 10^5$ cells per condition were washed in a PBS-1% BSA solution, then incubated for sequential 1 hour periods on ice with the indicated primary and secondary antibodies diluted in a 200 microliters total volume of PBS-1% BSA, with three washes in PBS-1% BSA between steps. Cells were analyzed on a BD FACScan.

For LDH release assays, cells were washed and plated in F12K media at a density of $1.5 \times 10^4$ cells per well. The subsequent day, cells were washed in F12K media and cultured at 37° C. with media containing the indicated concentration of recombinant toxin. LDH activity was determined using a cytotoxicity detection kit (Roche).

Murine S. aureus infection, treatment with active Hla, and bronchoalveolar lavage. For studies using wild-type mice, 50 ml culture aliquots of strains USA300 or USA300 Hla- were centrifuged and bacterial pellets were washed in PBS, pelleted, then resuspended in 1650 microliters of PBS. 30 microliters of this suspension was introduced to each mouse via intranasal route, delivering an inoculum of $2-3 \times 10^8$ S. aureus per mouse. For studies in which an inoculum of $7 \times 10^8$ Hla-S. aureus was delivered, a 50 ml culture was resuspended in 400 microliters of PBS. For acute lethal disease studies using $ADAM10^{-/-}$ mice, their littermate controls and GI254023X-treated mice, 50 ml culture aliquots of S. aureus strain Newman were prepared as stated above, except resuspended in 600 microliters of PBS to deliver an inoculum of $4-6 \times 10^8$ staphylococci per mouse. All animals utilized in these studies weighed between 16-19 g to maintain consistency with the S. aureus pneumonia model previously developed and extensively characterized in C57BL/6J mice (Bubeck Wardenburg and Schneewind, 2008; Bubeck Wardenburg et al., 2007a; Bubeck Wardenburg et al., 2007b). Purified, active Hla rendered endotoxin free via serial extraction with Triton-114 was delivered to all mice by intranasal inoculation in a total volume of 30 microliters. Animal experiments were reviewed, approved, and supervised by the Institutional Animal Care and Use Committee at the University of Chicago.

For bronchoalveolar lavage, mice were anesthetized as described, and the trachea exposed by midline skin incision. A 20-gauge catheter was inserted via direct visualization into the trachea, followed by the instillation of 1 ml of sterile PBS supplemented with protease inhibitor (Roche). 500 microliters of lavage fluid was recovered per animal. The number of total cells was enumerated, then cells were spun down and the supernatant was used for protein concentration assay (Bio Rad DC protein Assay kit) and immunoprecipitation of E-cadherin.

To calculate clinical disease severity scores, animals received an activity assessment score as follows: 1—animal is bright, alert, active, eating and drinking normally; 2—alert but somewhat less active, feces and urine present in cage; animals spontaneously move about in cage upon visual inspection of the cage (not necessary to move the cage); 3—animal less alert, not huddled, fur not ruffled; only move when the cage is moved—no spontaneous movement in the cage upon visual inspection; 4—animals huddled with ruffled fur; decreased or absent spontaneous movement upon visual inspection of cage, however when animal is touched, will readily move; maintains 'righting reflex'; 5—hunched and ruffled, animal does not move when touched, or absent 'righting reflex'; 6—recumbent; 7—death. This score was added to the weight loss of the animal at each respective time point relative to the start of the experiment to derive the overall clinical disease severity score.

Statistical analysis. Statistical significance of cell accumulation and protein concentration in BAL fluid as well as intensity quantification for immunofluorescence microscopy and clinical disease severity was calculated using the two-tailed Student's t-test. Significance of animal mortality studies was quantified by logrank test.

Results

Figure 11:
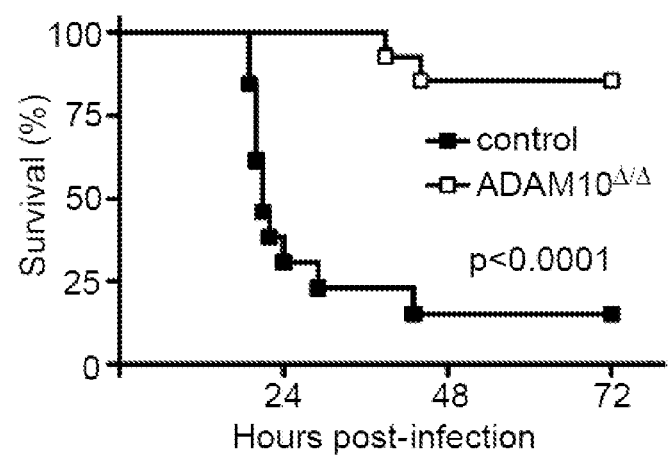
FIG. 11. ADAM10 contributes to lethal *S. aureus* pneumonia. Survival curves for mice harboring conditional deletion of Adam10 in the respiratory epithelium (ADAM10$^{\Delta/\Delta}$) relative to non-deleted littermate controls following infection with *S. aureus* strain Newman. n=14 mice, control and 15 mice, ADAM10$^{-/-}$.
Figures 15A, 15B, 15C:
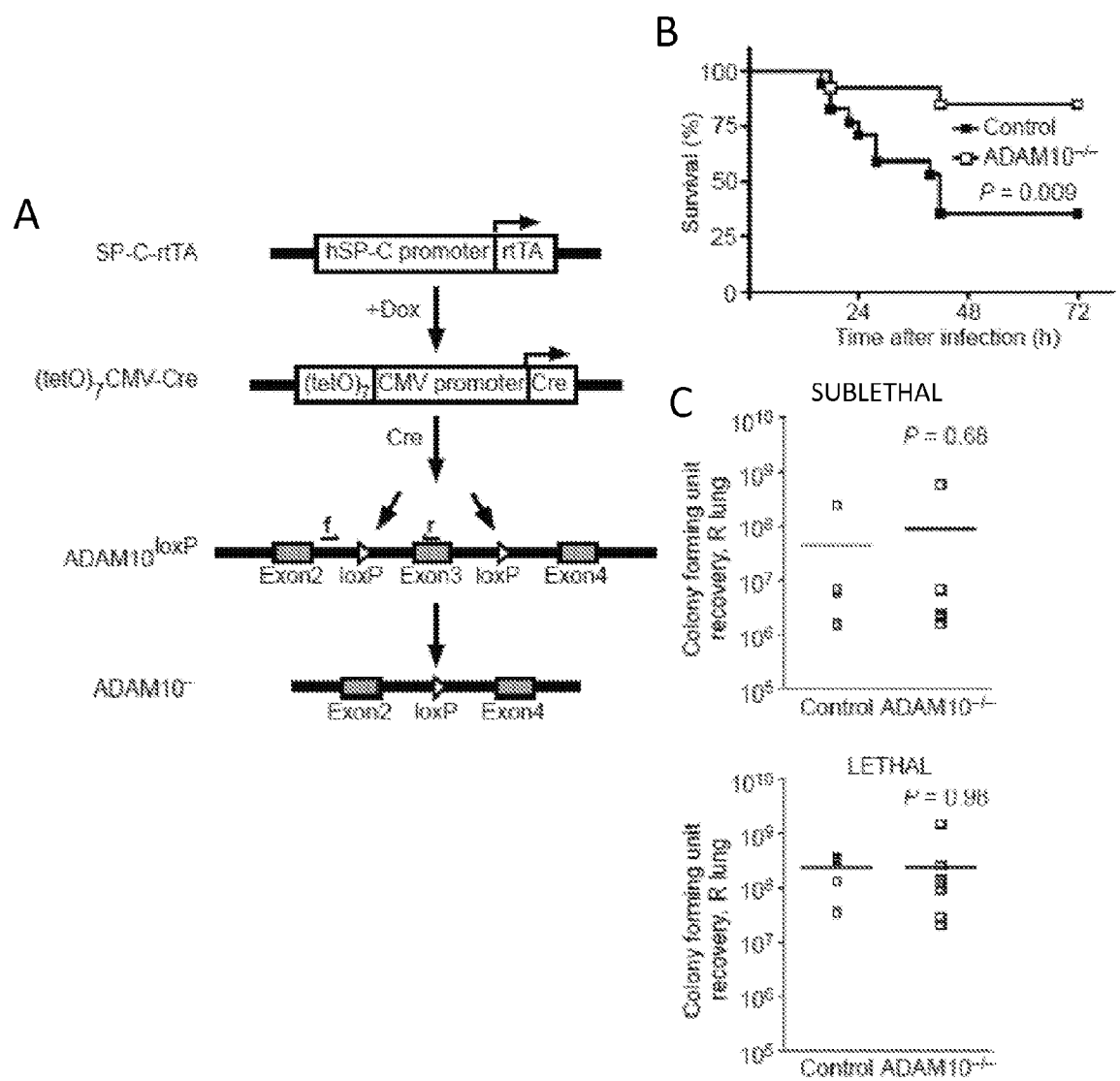
FIGS. 15A-15C. Generation of ADAM10$^{-/-}$ conditional knockout mice and response to infection. (A) Schematic demonstrating the breeding strategy to derive mice harboring deletion of ADAM10 in the intrapulmonary epithelium (ADAM10$^{-/-}$) under the control of the surfactant protein C promoter. Labels "f" and "r" indicate forward and reverse primers utilized to document Cre-dependent excision of exon 3 via PCR. (B) Survival curves in ADAM10$^{-/-}$ and control mice following infection with *S. aureus* strain USA300/LAC. n=17 mice, control and 13 mice, ADAM10$^{-/-}$. Recovery of *S. aureus* from the lungs of infected control and ADAM10$^{-/-}$ mice following sublethal infection (C, upper panel, n=6 control and n=7 ADAM10$^{-/-}$) and lethal infection (lower panel, n=5 control and n=10 ADAM10$^{-/-}$).

ADAM10 knockout mice exhibit early embryonic lethality (Hartmann et al., 2002). To examine the requirement for ADAM10 in staphylococcal pneumonia, surfactant protein C (SP-C) promoter-driven expression of Cre-recombinase was used to generate mice harboring Adam10 deletion in respiratory epithelium (FIG. 15A) (Perl et al., 2002; Tian et al., 2008). This system achieves recombination in SP-C-expressing progenitor type II pneumocytes, yielding ADAM10-deficient type I pneumocytes that constitute the alveolar epithelium; genomic analysis and protein expression confirmed recombination (FIGS. 15B, 15C). Knockout mice (ADAM10$^{-/-}$) were resistant to lethal pneumonia caused by methicillin-sensitive (FIG. 11) and methicillin-resistant (FIG. 15B) strains. Histopathologic examination of ADAM10$^{-/-}$ lungs following sublethal infection revealed limited inflammatory cell influx and preservation of alveolar structure. Lethal infection in controls caused widespread consolidation and cellular infiltration, while ADAM10$^{-/-}$ mice exhibited more localized disease. ADAM10 knockout did not alter lung bacterial load (FIG. 15C), in contrast to the reduction observed in Hla-deficient S. aureus infection or upon toxin neutralization (Bubeck Wardenburg and Schneewind, 2008; Ragle and Bubeck Wardenburg, 2009). Toxin-mediated injury therefore augments bacterial recovery independent of epithelial ADAM10 expression, whereas ADAM10 expression is essential for progressive, lethal disease.

Zinc-dependent catalysis by ADAM10 results in ectodomain cleavage of proteins that modulate immunity in addition to E-cadherin that facilitates inter-epithelial cell adhesion (Reiss and Saftig, 2009; Seals and Courtneidge, 2003). As epithelial barrier integrity is disrupted in pneumonia, ADAM10 enzymatic activity may contribute to toxin-mediated injury. To assess whether Hla alters ADAM10 metalloprotease activity, a fluorogenic peptide cleavage assay was performed on A549 alveolar epithelial cells treated with 10 micrograms ml$^{-1}$ active Hla (300 nM), a subcytolytic concentration (FIG. 16A). Intoxication induced metalloprotease activity in irrelevant siRNA-treated cells (FIG. 12A), a response not elicited by a non-oligomerizing Hla$_{H35L}$ mutant (Menzies and Kernodle, 1994). ADAM10 siRNA-treated cells only exhibited activity comparable to irrelevant siRNA-transfected cells at 30 minutes, likely owing to residual ADAM10 expression (FIG. 12A, FIG. 16B and Wilke and Bubeck Wardenburg (2010)); activity in ADAM10 siRNA-treated cells thereafter declined.

To evaluate the effects of increased ADAM10 activity on barrier function, electrical cell substrate impedance sensing (ECIS) was utilized, recording toxin-induced changes in A549 monolayer resistance. Intoxication caused rapid loss of resistance in irrelevant transfectants (FIG. 12B) whereas ADAM10 knockdown preserved barrier function similar to controls (PBS and Hla$_{H35L}$. The ADAM10 requirement in barrier disruption was evident even at 50 micrograms ml$^{-1}$ Hla wherein cytolytic injury occurs shortly post-intoxication and can be receptor-independent (FIG. 16A and Wilke and Bubeck Wardenburg (2010)).

Bacteria circumvent host barrier defenses through virulence factors that dismantle the structural framework of the epithelium (Kim et al., 2010). Proteolysis of the E-cadherin extracellular domain by ADAM10 severs the homotypic, adherens junction-based linkage between adjacent cells (Maretzky et al., 2005. To examine whether Hla-induced ADAM10 activation caused E-cadherin cleavage, lysates from A549 cells were analyzed by immunoprecipitation and immunoblotting. ADAM10-mediated cleavage releases the E-cadherin's N-terminal extracellular domain, leading to reduction in full-length (FL) protein and appearance of an intracellular C-terminal fragment (CTF) (Maretzky et al., 2005). Ionomycin induces ADAM10 activity Murphy, 2009), enhancing cleavage compared to DMSO or Hla$_{H35L}$ treatment, while Hla (20 micrograms/ml) triggered rapid cleavage. Concentrations of Hla as low as 1 micrograms/ml induced cleavage within 1 hour. Immunofluorescence microscopy confirmed loss of E-cadherin. Cells transfected with ADAM10 siRNA did not reveal toxin-induced CTF generation, maintaining E-cadherin expression.

Figure 12C:
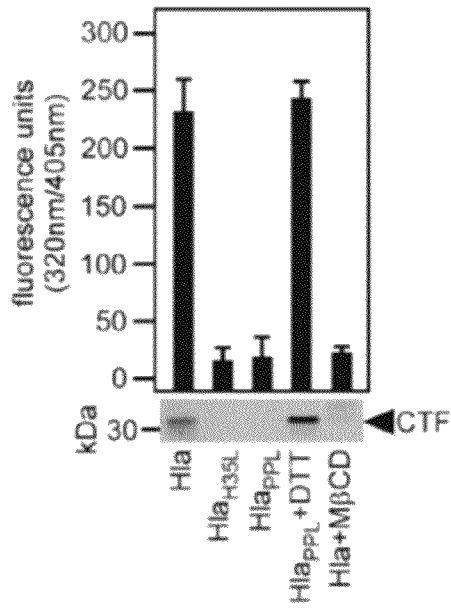
Figure 12D:
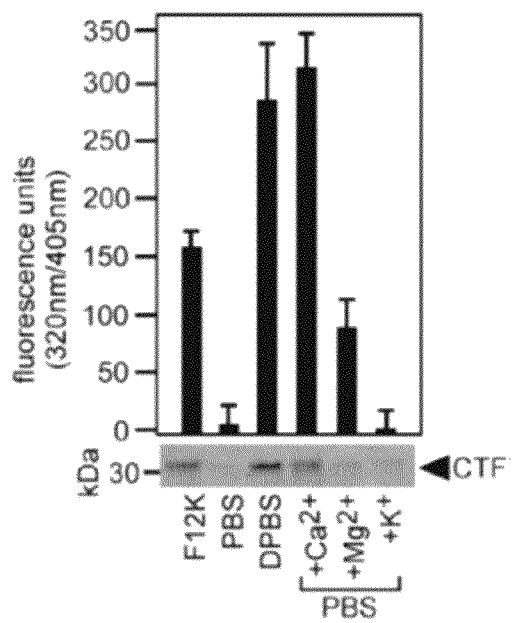

To define the structural form of Hla that activates ADAM10, toxin assembly intermediates were examined. These include monomeric Hla$_{H35L}$ that binds to ADAM10 but cannot form stable heptamers, and a pre-pore locked mutant (Hla$_{PPL}$) containing an engineered disulfide bond that allows heptamer formation but prevents toxin insertion into the membrane until dithiothreitol is present (Hla$_{PPL}$+DTT). Only Hla$_{PPL}$+DTT activated ADAM10 and led to E-cadherin cleavage (FIG. 12C), demonstrating a requirement for the pore. Methyl-β-cyclodextrin (MβCD)-mediated blockade of the pore abrogated metalloprotease activation and E-cadherin cleavage. These findings suggested that the pore may serve as an ion conduit, triggering downstream signaling. Indeed, calcium in the media as observed in F12K, Dulbecco's PBS (DPBS, containing Ca$^{2+}$, Mg$^{2+}$ and K$^+$) and PBS+Ca$^{2+}$ was required (FIG. 12D).

Figure 16C:
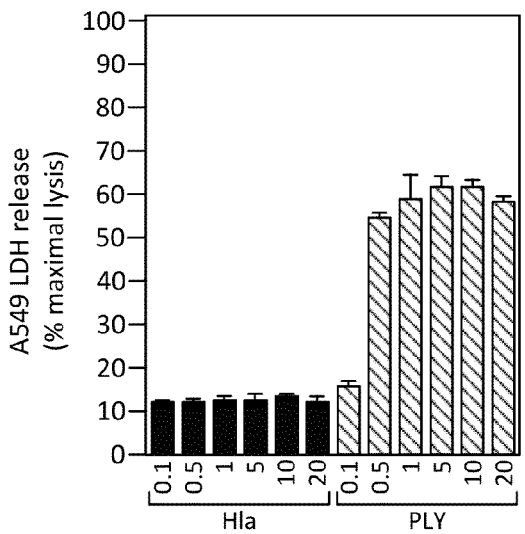
Figure 16C:
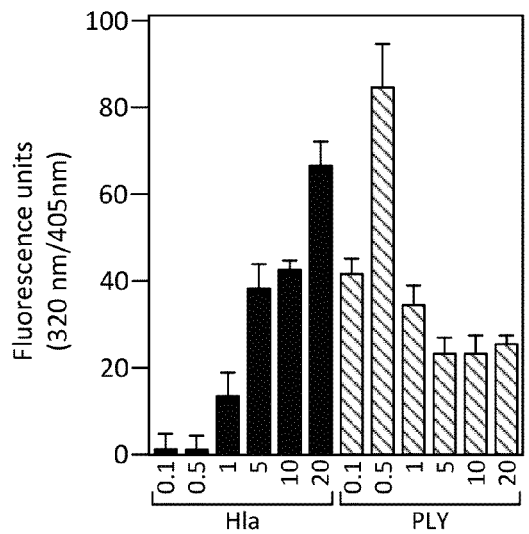

To further examine pore formation in ADAM10 activation, A549 cells were treated with S. pneumoniae pneumolysin (PLY), a cholesterol-dependent PFT implicated in pneumococcal pneumonia (Rubins et al., 1995). PLY is highly cytotoxic (FIG. 16C, upper), inducing cell-associated metalloprotease activity (lower), notably at lower toxin concentrations wherein E-cadherin cleavage was observed. These data suggest that ADAM10 may be utilized by multiple PFTs for pathologic E-cadherin cleavage. Cleavage was most prominent at highly cytotoxic PLY concentrations, likely reflecting metalloprotease-dependent E-cadherin cleavage during apoptosis triggered by PLY (Marriott and Dockrell, 2006; Steinhusen et al., 2001). The receptor function of ADAM10 may specifically target Hla action to the epithelium, potentiating the ability of the small pore to activate ADAM10 and cause E-cadherin cleavage at subcytolytic concentrations.

Acute lung injury is associated with loss of epithelial barrier function, leading to accumulation of cellular, proteinaceous edema (Matthay and Zemans, 2011). To examine the role of Hla in E-cadherin cleavage and barrier disruption in vivo, a mouse S. aureus pneumonia model was utilized. Hla-deficient strains demonstrate limited virulence in this model, and toxin neutralization protects against disease (Bubeck Wardenburg and Schneewind, 2008; Ragle and Bubeck Wardenburg, 2009). C57BL/6J mice were infected with wild-type (WT) S. aureus USA300/LAC or an isogenic Hla-deficient mutant (Hla-). Bronchoalveolar lavage (BAL) was performed to evaluate E-cadherin cleavage, measuring N-terminal fragment (NTF) release. Infection with non-toxigenic S. aureus led to minimal NTF detection in contrast to WT infection. Alveolar barrier disruption was observed as increased BAL cell counts following WT infection, a response that was blunted in Hla-infection (FIG. 13A). BAL protein analysis revealed exudation by 6 hours in WT-infected animals, rising through 24 hours (FIG. 13B). Minimal influx was seen in Hla-infected mice at 6 and 24 hours, with increased protein at 12 hours likely reflective of the host inflammatory state (Bubeck Wardenburg et al., 2007a; Bubeck Wardenburg et al., 2007b; Bubeck Wardenburg and Schneewind, 2008). Toxin-independent inflammation in this setting may result from other virulence factors, notably Protein A-mediated TNF receptor activation (Gomez et al., 2007), or the effects of CXCR3 chemokines on host immune cells (Martin et al., 2011).

Figure 17A:
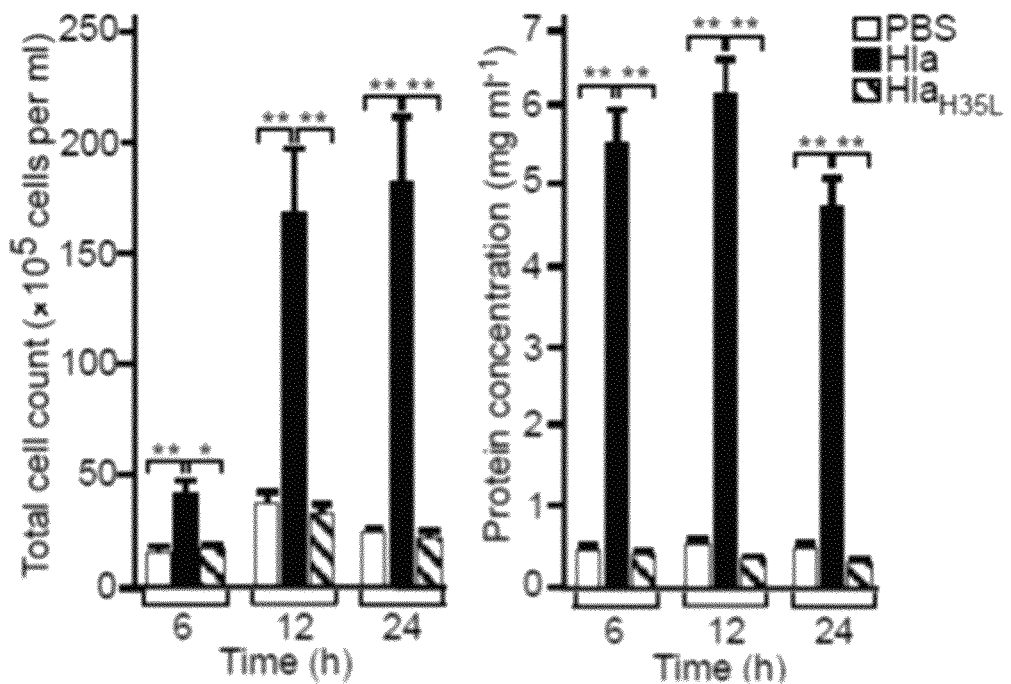
FIGS. 17A-17B. Purified, active Hla elicits lung injury in vivo. (A) BAL fluid analysis of cell count (left) and protein exudation (right) at 6, 12, and 24 hours following instillation of 0.4 micrograms Hla or Hla$_{H35L}$ or control PBS in C57BL/6J mice. n=8. (B) Clinical disease severity recordings in ADAM10$^{-/-}$ (white bars) and control littermate mice (black bars) following infection with an increased inoculum of Hla-*S. aureus*.
Figure 17B:
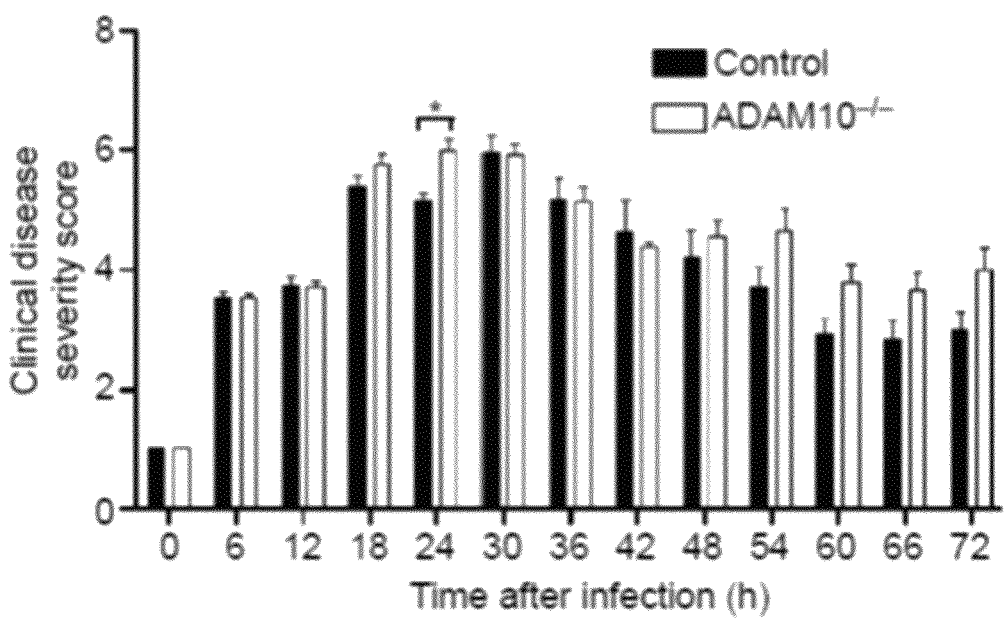

To examine Hla sufficiency in eliciting E-cadherin cleavage, 0.4 micrograms Hla or Hla$_{H35L}$ was delivered intranasally to mice. Only Hla treatment led to NTF accumulation with increasing cell counts and alveolar protein (FIG. 17A). Within 4 hours, when signs of injury were not apparent, E-cadherin cleavage was already evident. Hla induced minimal E-cadherin cleavage in ADAM10$^{-/-}$ mice. BAL cell recovery in ADAM10$^{-/-}$ mice was blunted, with markedly reduced protein accumulation (FIG. 13C). Infection of C57BL/6J mice with a ~2.5-fold greater inoculum of Hla-S. aureus did not result in increased E-cadherin cleavage, protein leakage (FIG. 26D, right), or death, in spite of a trend toward increased cell recovery (FIG. 26D, left). Delivery of high-inocula Hla-S. aureus to ADAM10$^{-/-}$ mice and controls resulted in similar disease severity (FIG. 17B).

These observations raised the possibility that metalloprotease inhibition may mitigate toxin action. Treatment of A549 cells with the ADAM10-specific inhibitor GI254023X (Ludwig et al., 2005) abrogated E-cadherin cleavage, correlating with preservation of monolayer resistance (FIG. 14A). A549 cells do not form a polarized epithelium, thus observations were confirmed in the 16HBE14o-polarized bronchial epithelial line (FIGS. 18A-18B). ADAM10 expression did not display polarity (Dijkstra et al. (2009)). Unexpectedly, GI254023X impaired toxin binding and oligomerization on A549 cells, perhaps owing to conformational changes that alter toxin association. GI254023X treatment of mice prevented E-cadherin cleavage, reduced alveolar exudates (FIG. 19A) and protected against lethal pneumonia (FIG. 14B). Preincubation of GI254023X with rabbit red cells, but not toxin, blunted hemolysis, confirming that this strategy targets the host (FIG. 19B). GI254023X prevented PLY-induced E-cadherin cleavage, thus may represent a broadly-applicable strategy against PFT-mediated injury.

Next, the requirement for ADAM10 in PLY-mediated disease was tested by intranasal delivery of PLY to mice, followed by characterization of NTF accumulation in the BAL recovery fluid. PLY treatment resulted in E-cadherin cleavage in the lungs of wild-type (WT) but not ADAM10–/– mice that harbor a deletion of ADAM10 in the respiratory epithelium. Mice received 40 micrograms purified recombinant pneumolysin via intranasal application followed by bronchoalveolar lavage (BAL) 4 hours later. BAL fluid was analyzed for the presence of the N-terminal cleavage fragment (NTF) of E-cadherin by immunoprecipitation and immunoblotting. NTF accumulation was observed in the BAL fluid from the WT mice but not the ADAM10–/– mice, indicating that PLY-mediated E-cadherin cleavage was suppressed in the absence of ADAM10. This data supports the use of an ADAM10 inhibitor to reduce or protect against PLY-mediated disease severity.

These studies enhance knowledge of PFT biology, defining the role of a proteinaceous receptor in S. aureus pathogenesis. The use of ADAM10 as the Hla receptor confers functionality to the toxin, coupling target binding with epithelial barrier disruption. This mechanism of action permits a clearer understanding of the toxin's tropism for barrier-forming cells, and barrier disruption emerges as a critical early pathologic disturbance that is directly linked to lethal disease outcome.

Example 3

Materials and Methods

Recombinant Hla and Hla$_{H35L}$, a mutant that demonstrates normal cell binding but is incapable of heptameric pore formation (Menzies and Kernodle, 1994), were prepared and purified as previously described (Wilke and Bubeck Wardenburg, 2010). Human pulmonary artery endothelial cells (HPAECs, Lonza) were cultured in EBM-2 BulletKit media (Lonza). S. aureus strains were described previously and propagated in tryptic soy broth (TSB) (Bubeck Wardenburg and Schneewind, 2008). Anti-human VE-cadherin antibody (Santa Cruz Biotechnology) and Alexa Fluor®-conjugated secondary antibodies (Invitrogen) were used according to the manufacturer's protocols for LI-COR Imaging System detection. The ADAM10 inhibitor GI254023X was synthesized by OKeanos Tech., Ltd (Beijing, China) according to a published synthetic path (Hoettecke et al., 2010). The inhibitor was resuspended in DMSO and applied to cells at 200↑ in complete media 16-18 hours prior to experimentation or administered to animals via intraperitoneal route following dilution in 0.1M carbonate buffer. Animals received 200 mg/kg/day in 2-4 divided doses beginning 3 days prior to delivery of purified Hla or infection, continuing throughout the course of observation.

siRNA treatment was conducted as previously reported using 100 nanomoles of irrelevant or ADAM10-specific siRNA (Applied BioSciences) (Dudek et al., 2010). Cells were grown 24 hours in complete media then replated for experimentation. Flow cytometric analysis and LDH assays were performed as described (Wilke and Bubeck Wardenburg, 2010). Metalloprotease assays were performed by plating $1.5 \times 10^4$ HPAECs in 96-well dishes 24 hours prior to experimentation. Cells were incubated with recombinant Hla or PBS in unsupplemented EBM-2 media for the time periods indicated, washed in 25 mM Tris, pH 8.0 buffer and incubated at 37° C. with 10 micromolar fluorogenic peptide substrate (Mca-PLAQAV-Dpa-RSSSR—NH$_2$, R&D Systems). Fluorescence intensity was measured on a BioTek SynergyHT reader.

For detection of VE-cadherin in HPAECs, cells were plated at a density of $2.5 \times 10^5$/6-well or $1 \times 10^5$/24-well. Cell monolayers were rinsed in PBS and incubated with recombinant Hla in unsupplemented EBM-2 for the indicated times. DMSO or ionomycin (5 µM) controls were added to monolayers 20 min prior to cell processing. For biochemical studies, cell lysates were immunoprecipitated with anti-VE-cadherin antibody and protein G sepharose (Pierce) at 4° C. overnight, then analyzed by immunoblotting according to published protocols (Wilke and Bubeck Wardenburg, 2010). For immunofluorescence microscopy, rinsed monolayers were methanol-fixed for 10 min, stained and visualized according to published protocols (Wilke and Bubeck Wardenburg, 2010).

The effect of Hla on endothelial barrier function was measured with an electrical cell substrate impedance sensing system (Applied BioPhysics). $1 \times 10^5$ HPAECs were seeded in 8W10E cultureware and incubated at 37° C. in a CO$_2$ incubator. Resistance of the monolayer was recorded until a stable resistance of approximately 600-1000 ohms was documented prior to the addition of purified toxin.

Lethal infection studies were performed in BALB/c mice (Charles River) as described, according to a protocol approved by the University of Chicago Institutional Animal Care and Use Committee (Kim et al., 2010b). To assess endothelial barrier disruption in vivo, 1 micrograms of endotoxin-free recombinant toxin was delivered by subcutaneous injection in 100 microliters, followed 3 hours later by the intravenous delivery of 100 microliters 2% Evans Blue dye. Mice were sacrificed 30 min later and dye extravasation quantified in excised skin by formamide extraction (65° C., 24 h) and spectrophotometric detection (620 nm).

Statistical analysis of mortality studies was performed by logrank test; all other statistical analysis was performed using the two-tailed Student's t-test.

Results

To investigate the role of Hla in staphylococcal sepsis, a mouse model of intravenous infection that causes rapidly progressive, lethal disease was used (Kim et al., 2010b). Groups of 6 week-old mice were infected with $1\times10^8$ colony forming units (CFU) *S. aureus* Newman or $2.5\times10^7$ CFU USA300/LAC, representing a methicillin-sensitive and a highly virulent epidemic methicillin-resistant clones, respectively. Infection with wild-type (closed boxes) strains of Newman (FIG. 20A, upper panel) and USA300/LAC (FIG. 20A, lower panel) led to acute lethality within 24-96 hours. Previously characterized isogenic mutants (Bubeck Wardenburg and Schneewind, 2010) of these strains ((Bubeck Wardenburg and Schneewind, 2010), Hla-, open boxes) were less virulent, indicative of a role for Hla in the pathogenesis of sepsis.

Figure 22A:
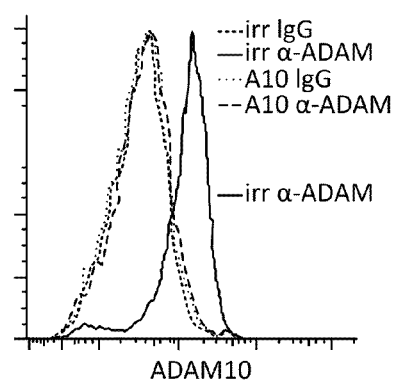
FIGS. 22A-22D. siRNA knockdown of ADAM10 in HPAECs prevents Hla-mediated death and VE-cadherin cleavage. (A-C) In all experiments, HPAECs were transfected with irrelevant (in) or ADAM10 (A10)-specific siRNA. (A), siRNA-mediated knockdown of ADAM10 demonstrated by flow cytometric analysis using either IgG (control) or α-ADAM for detection. (B), HPAECs were treated with varying concentrations of Hla for 4 hours and cell death measured by LDH release. (C), Barrier resistance measured by ECIS in cells treated with 75 nM Hla and in or A10, or with PBS as a control. (D), ECIS recordings of barrier resistance measured in GI254023X-treated cells (20 µM) following Hla exposure (75 nM) or in cells treated with PBS and DMSO controls.
Figure 22B:
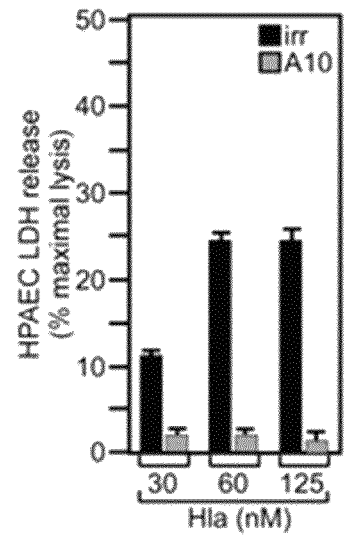

HPAECs were treated with irrelevant or ADAM10-specific siRNA, followed by confirmation of knockdown by flow cytometry (FIG. 22A), then exposed to purified active Hla. ADAM10 knockdown cells were highly resistant to intoxication (FIG. 22B) compared to irrelevant siRNA-treated cells, extending the earlier observations on the requirement of ADAM10 expression for Hla-mediated injury to endothelial cells.

To examine whether an interaction of Hla with ADAM10 on endothelial cells affects the receptor's metalloprotease activity, HPAECs transfected with irrelevant or ADAM10-specific siRNA were treated with 150 nM purified, active Hla or $Hla_{H35L}$ (Bubeck Wardenburg and Schneewind, 2010). Toxin-treated cells were subjected to analysis of metalloprotease activity via fluorescent peptide cleavage assay. Hla induced a rapid increase in enzymatic activity in irrelevant siRNA-treated cells (FIG. 20B, black), whereas inducible metalloprotease activity was nearly absent on cells treated with $Hla_{H35L}$ or active toxin following ADAM10 knockdown (FIG. 20B, hatched).

Figure 22C:
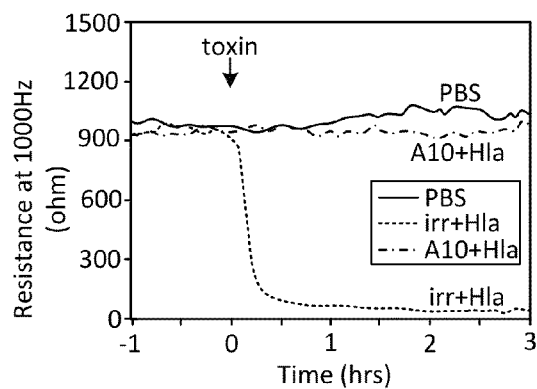

To examine the role of ADAM10 in toxin-mediated endothelial barrier disruption, electrical cell-substrate impedance sensing (ECIS) was used to measure transendothelial electrical resistance. HPAEC monolayers treated with 75 nM Hla demonstrated a rapid and progressive loss of resistance (FIG. 20C), detectable upon treatment with concentrations to 30 nM. Neither PBS nor $Hla_{H35L}$ altered monolayer resistance. Toxin-induced loss of endothelial barrier function was prevented by ADAM10 knockdown (FIG. 22C).

The above data, in light of existing observations, suggested that ADAM10 indeed provides the mechanistic link between Hla and endothelial barrier disruption. ADAM10-mediated VE-cadherin cleavage leads to the release of an N-terminal extracellular fragment, while an ~35kD C-terminal intracellular fragment (CTF) remains tethered to the membrane (Schulz et al., 2008). To examine whether toxin treatment resulted in this specific cleavage event, HPAECs were treated with 225 nM purified Hla or $Hla_{H35L}$ for 1 hr. Lysates were prepared and subjected to VE-cadherin immunoprecipitation and immunoblot analysis. Toxin treatment induced loss of FL VE-cadherin, with concomitant detection of the CTF as early as 15 min following toxin exposure. Cleavage was confirmed by immunofluorescence microscopy, revealing loss of surface expression of VE-cadherin and the appearance of gaps between neighboring cells. VE-cadherin cleavage was dependent on ADAM10 expression, demonstrated by biochemical and microscopic analysis of siRNA-treated cells.

To assess the ability of Hla to mediate endothelial barrier disruption in vivo, a Miles assay was performed, examining for extravasation of Evans blue dye from the vasculature into the subcutaneous tissue where Hla or $Hla_{H35L}$ had been injected 3 hours prior. Intact endothelium retains dye within the vessel, whereas dye infiltrates the tissue where endothelial integrity is breached. Mice treated with Hla were observed to accumulate dye surrounding the site of toxin injection, which was marked with a central region of erythema (arrow) and induration. In contrast, dye extravasation, erythema, and induration were not seen in mice that received PBS or $Hla_{H35L}$. Dye accumulation was quantified by spectrophotometry ($OD_{620}$ nm) following extraction from excised skin, confirming the effects of the active toxin (PBS, 0.025±0.001, $Hla_{H35L}$, 0.049±0.017, Hla, 0.161±0.027; p=0.0004 PBS vs. Hla and 0.00005 $Hla_{H35L}$ vs. Hla).

Figure 22D:
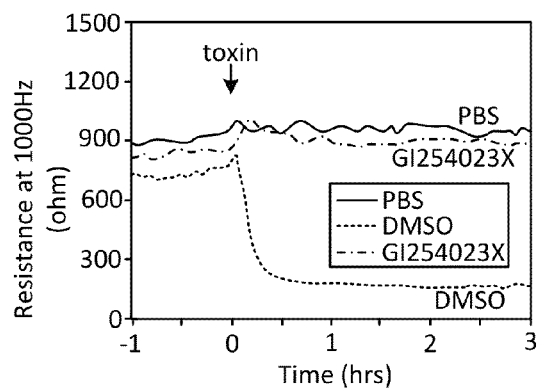

Pathogen-induced microvascular injury contributes to widespread vascular permeability and uncontrolled inflammation, compromising blood flow to vital organs and impairing organ function (Lemichez et al., 2010). It was reasoned that prevention of *S. aureus*-mediated endothelial injury may limit the deleterious effects of endovascular infection, and examined whether the use of a small molecule metalloprotease inhibitor of ADAM10 could prevent Hla-mediated endothelial barrier disruption. HPAECs were treated with 20 micromolar of the ADAM10 metalloprotease inhibitor GI254023X followed by the addition of active Hla (Ludwig et al., 2005). GI254023X prevented VE-cadherin cleavage as revealed by immunoblot analysis and immunofluorescence microscopy when compared to treatment with PBS or the DMSO vehicle and Hla. ECIS studies revealed complete protection of HPAECs from Hla-mediated barrier disruption in the presence of GI254023X (FIG. 22D).

To examine the ability of GI254023X to inhibit Hla-mediated endothelial barrier disruption in vivo, mice treated for a 3-day period with GI254023X via intraperitoneal injection were subjected to a Miles assay following subcutaneous injection of recombinant toxin. This treatment strategy was selected based on previous in vivo trials of metalloprotease inhibitors, in the absence of known pharmacologic studies of GI254023X (Pochetuhen et al., 2007). Treatment with the ADAM10 inhibitor enhanced vascular integrity, manifest by limited dye extravasation compared to DMSO-treated mice. This observation, together with a role for Hla in a sepsis model (FIG. 1), suggested that ADAM10 inhibition may afford protection against lethal infection. Mice were treated with either DMSO or GI254023X then infected with $5\times10^7$ CFU *S. aureus* Newman. While all experimental animals succumbed to the lethal challenge, GI254023X-treated mice were less ill in appearance and demonstrated prolongation of time-to-death (FIG. 21).

Example 4

Figure 23A:
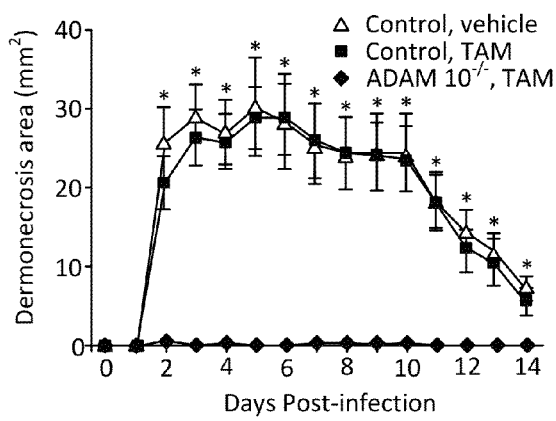
FIGS. 23A-23D. ADAM10 mediates a-hemolysin dependent epithelial injury. (A) Dermonecrosis area recorded from control mice that received topical treatment with vehicle alone (n=13) or TAM (n=8), or ADAM10$^{-/-}$ mice treated with TAM (n=13) followed by subcutaneous infection with 3×10$^7$ S. aureus USA300/LAC, where * denotes P<0.001. (B) Abscess area recorded from mice detailed in (A) where + denotes P<0.05. Area in (A) and (B) was calculated based on the formula A=[π/2]×length×width where error bars represent SEM. (C) Cell-associated metalloprotease activity measured in A431 keratinocytes following treatment with 10 micrograms/ml (300 nM) active Hla or the non-toxigenic mutant Hla$_{H35L}$ at the time points indicated. Activity was quantified by detection of the product derived from cleavage of the fluorogenic peptide substrate Mca-PLAQAV-Dpa-RSSSR—NH$_2$ (10 micromolar, R&D Systems, Minnesota) diluted in 25 mM Tris, pH 8.0. (G) Electrical cell substrate impedance sensing (ECIS, Applied Biophysics, New York) recordings of A431 monolayers treated with PBS, the Hla$_{H35L}$ mutant (10 micrograms/ml), or active Hla (10 micrograms/ml).
Figure 23B:
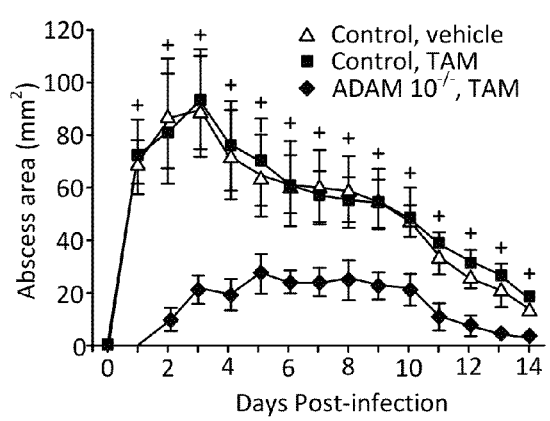

The zinc-dependent metalloprotease ADAM10 was recently identified as the cellular receptor for Hla (Wilke and Bubeck Wardenburg, 2010). ADAM10 regulates epithelial tissue function through its ability to cleave the ectodomain of E-cadherin, severing the protein-based adherens junction tether between adjacent cells Maretzky et al., 2005). ADAM10 is necessary for epithelial homeostasis, yet has also been implicated as a contributor to pathologic injury in malignancy and atopic dermatitis (Maretzky et al., 2008; Reiss and Saftig, 2009). ADAM10 knockout mice exhibit embryonic lethality (Hartmann et al., 2002). Therefore, to examine the contribution of ADAM10 to skin infection, an ADAM10 conditional knockout mice was generated in which the $3^{rd}$ exon of ADAM10 is flanked by loxP sites (Tian et al., 2008) and excised in the presence of a Cre recombinase expressed under control of the keratin 14 promoter (Vasiouklin et al., 1999). Daily topical application of tamoxifen (TAM) for 5 days leads to localized activation of the Cre recombinase, abrogating epidermal expression of ADAM10. In contrast to littermate control mice, ADAM10$^{-/-}$ mice did not develop dermonecrotic skin lesions following subcutaneous infection with $3 \times 10^7$ colony forming units of the highly virulent epidemic S. aureus strain USA300/LAC (FIG. 23A). Abscess size was also reduced in ADAM10$^{-/-}$ mice (FIG. 23B).

Figure 23C:
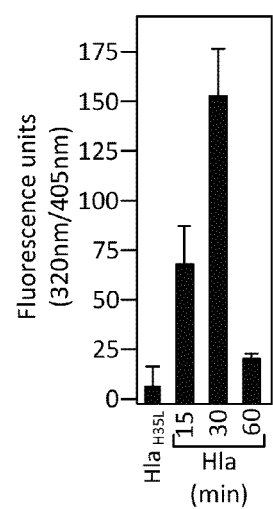
Figure 23D:
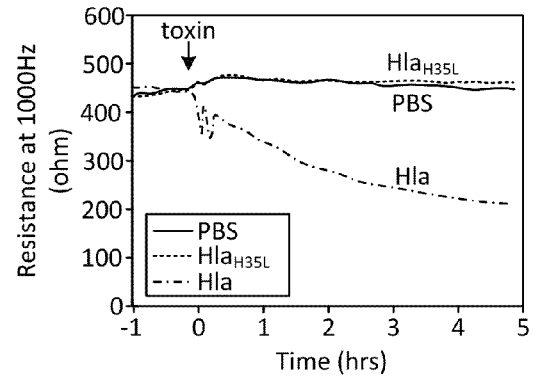

The ability of ADAM10 to cleave E-cadherin suggested that Hla may utilize its receptor to cause epithelial barrier injury, not merely to facilitate cell binding. Toxin treatment of A431 keratinocytes led to rapid upregulation of cell-associated metalloprotease activity as measured in an in vitro fluorogenic substrate cleavage assay (FIG. 23C). In contrast, a non-pore-forming mutant of Hla, Hla$_{H35L}$ (Menzies and Kernodle, 1994), was unable to elicit this response. Enhanced metalloprotease activity correlated with E-cadherin cleavage, detectable by immunoblot analysis of E-cadherin precipitates from lysates prepared from toxin-treated cells as the loss of full-length protein and accumulation of a characteristic C-terminal fragment produced by ADAM10-dependent cleavage. These molecular events occurred at subcytolytic concentrations of Hla (10 micrograms per ml), wherein a physiologic disturbance of epithelial barrier function was rapidly manifest as a loss of monolayer resistance using electrical cell-substrate impedance sensing (ECIS) on toxin-exposed A431 cells (FIG. 23D).

Figures 24A, 24B, 24C:
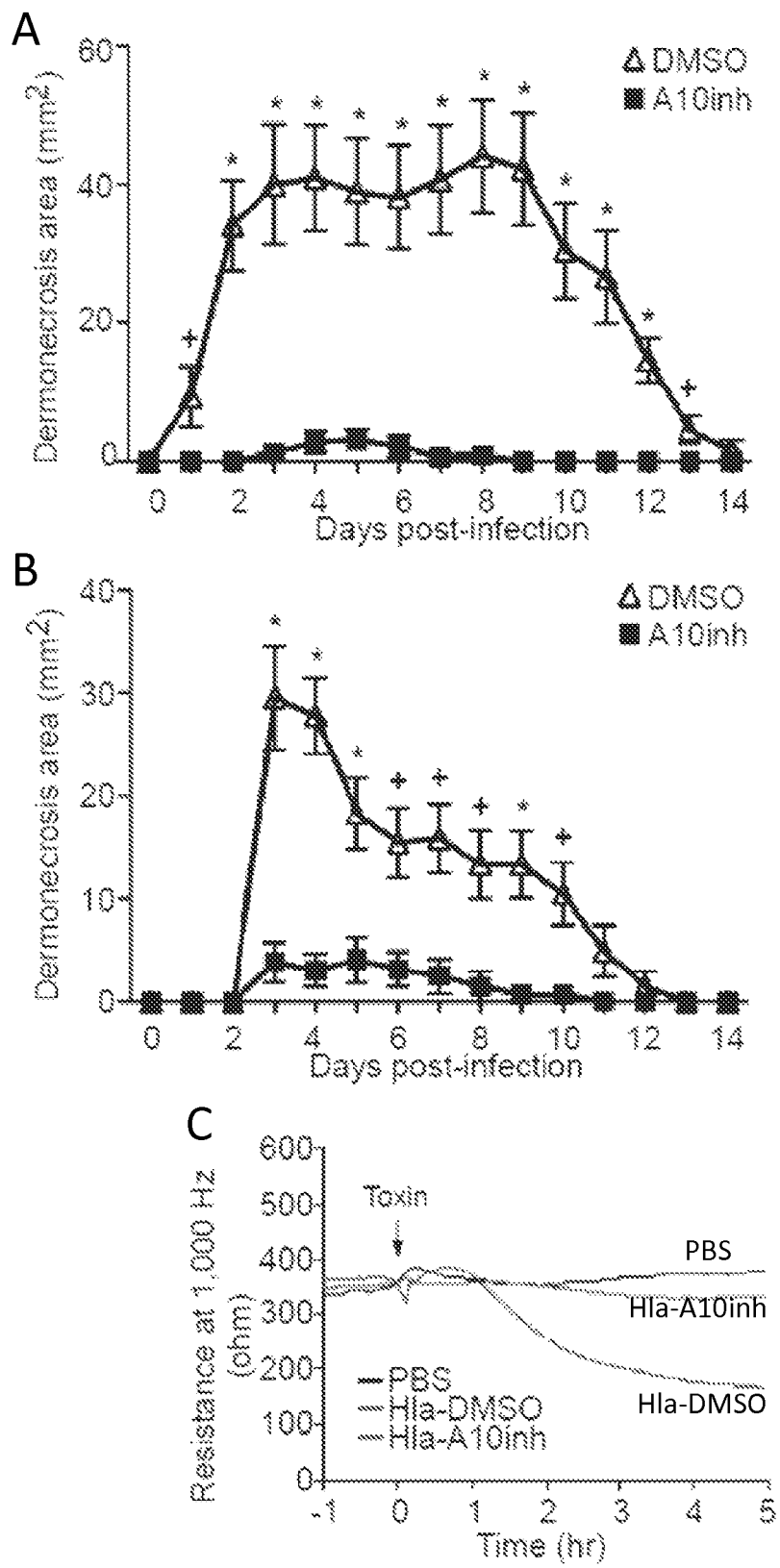
FIGS. 24A-24C. An ADAM10 inhibitor protects against Hla-induced injury. (A) Dermonecrosis area recorded from wild-type mice that received a five-day course of once-daily intraperitoneal injection with vehicle alone (DMSO) or the ADAM10 inhibitor GI254023X (200 mg per kg per day, Okeanos, China), followed by subcutaneous infection with 3×10$^7$ S. aureus USA300/LAC (n=10 mice per group). (B) Dermonecrosis area recorded from wild-type mice that received a five-day course of once-daily topical application with vehicle alone (DMSO) or the ADAM10 inhibitor GI254023X (100 mg per kg per day), followed by subcutaneous infection with 3×10$^7$ S. aureus USA300/LAC (n=10 mice per group), where + denotes P<0.05 and * denotes P<0.001 in (A) and (B). (C) Electrical cell substrate impedance sensing (ECIS) recordings of A431 monolayers treated with PBS, or Hla (10 micrograms/ml) following pre-treatment with control DMSO or GI254023X (20 micrograms/ml).

Together, these findings support the concept that the principal role of the toxin-receptor complex may be to disrupt the epithelial barrier, congruent with a number of studies that illustrate the importance of Hla in virulence at epithelial sites including the lung, vagina, peritoneum and eye (Brosnahan et al., 2009; Bubeck Wardenburg et al., 2007a; Bubeck Wardenburg et al., 2007b; Callegan et al., 1994; Menzies and Kernodle, 1996. Infection with S. aureus induced loss of epidermal E-cadherin staining at the infection site in control mice, while E-cadherin remained detectable by immunohistochemistry in infected ADAM10$^{-/-}$ mice. These data suggested that a small molecule inhibitor of ADAM10 metalloprotease activity may protect against dermonecrosis. Mice receiving systemic treatment with the ADAM10 inhibitor GI254023X (Ludwig et al., 2005) (200 mg per kg per day for five days) did not demonstrate dermonecrotic skin lesions following S. aureus infection compared to mice treated with the DMSO vehicle alone (FIG. 24A). Of particular importance for skin infection, topical application of GI254023X also completely prevented skin breakdown over the site of infection (FIG. 24B, 100 mg per kg per day for five days). Both routes of treatment led to a reduction in abscess size compared to treatment with DMSO. In vitro, GI254023X treatment resulted in preservation of full-length E-cadherin expression and epithelial barrier function upon A431 cell treatment with the toxin (FIG. 24C).

REFERENCES

The following references, to the extent that they provide exemplary procedural or other details supplementary to those set forth herein, are specifically incorporated herein by reference.

U.S. Pat. No. 6,172,064
U.S. Pat. No. 6,191,150
U.S. Pat. No. 6,329,400
U.S. Pat. No. 7,723,349
U.S. patent application Ser. No. 10/518,110
U.S. patent application Ser. No. 12/160,862
U.S. patent application Ser. No. 12/327,313
U.S. patent application Ser. No. 12/605,118
U.S. Patent Ser. 60/534,501
U.S. Patent Ser. 60/512,016
U.S. Patent Ser. 60/515,352
U.S. Patent Ser. 61/453,648
U.S. Patent Ser. 61/411,765
U.S. Patent Ser. 61/511,032
Bhakdi and Tranum-Jensen, *Microbiol. Rev.*, 55:733-751, 1991.
Brosnahan et al., *Immunol.*, 182:2364-2373, 2009.
Bubeck Wardenburg and Schneewind, *J. Exp. Med.*, 205:287-294, 2008.
Bubeck Wardenburg et al., *Infect. Immun.*, 75:1040-1044, 2007a.
Bubeck Wardenburg et al., *Nature Med.*, 13:1405-1407, 2007b.
Callegan et al., *Infect. Immun.*, 62:2478-2482, 1994.
Dijkstra et al., *Virchows Arch.*, 454:441-449, 2009.
Dudek et al., *Mol. Biol. Cell*, 21(22):4042-4056, 2010.
Emorl and Gaynes, *Clin. Microbiol. Rev.*, 6(4):428-42, 1993.
Gomez et al., *EMBO J.*, 26:701-709, 2007.
Gonzalez et al., *Cell Mol. Life Sci.*, 65:493-507, 2008.
Gumbiner, *Cell*, 84:345, 1996.
Harlow and Lane, In: *Antibodies: A Laboratory Manual*, Cold Spring Harbor Laboratory, 1988.
Hartmann et al., *Hum. Mol. Genet.*, 11:2615-2624, 2002.
Hoettecke et al., *Neurodegener. Dis.*, 7(4):232-238, 2010.
Hooper et al., *Biochem. J.*, 321:265-279, 1997.
Hooper, *FEBS Letters*, 354:1-6, 1994.
Hoy et al., *EMBO*, 11:798, 2010.
Iacovache et al., *Biochim Biophys Acta.*, 1778 (7-8): 1611-23, 2008.
Illek et al., *Cell Physiol. Biochem.*, 22:57-68, 2008.
Inoshima et al., *Nature Medicine*, 2011 (IN PRESS)
Jursch et al., *Infect. Immun.*, 62:2249, 1994.
Karginov et al., *Bioorg, Med, Chem.*, 15:5424, 2007.
Kennedy et al., *J. Infect. Dis.*, 202(7):1050-1058, 2010.
Kim et al., *Cell Host Microbe.*, 8(1):20-35, 2010a.
Kim et al., *Vaccine*, 28(38):6382-6392, 2010b.
Lemichez et al., *Nat. Rev. Microbiol.*, 8(2):93-104, 2010.
Lowy, *N. Engl. J. Med.*, 339:520, 1998.
Ludwig et al., *Comb. Chem. High Throughput Screen*, 8:161-171, 2005.
Maretzky et al., *Proc. Natl. Acad. Sci. USA*, 102:9182-9187, 2005.
Maretzky et al., *J. Invest. Dermatol.*, 128:1737-1746, 2008.
Marriott and Dockrell, *Int. J. Biochem. Cell Biol.*, 38:1848-1854, 2006.
Martin et al., *Infect. Immun.*, 79:1898-1904, 2011.
Matthay and Zemans, *Annu. Rev. Pathol.*, 6:147, 2010.
Matthay and Zemans, *Annu. Rev. Pathol.*, 28:147-163, 2011.
Menzies and Kernodle, *Infect. Immun.*, 62:1843-1847, 1994.
Menzies and Kernodle, *Infect. Immun*, 64:1839-1841, 1996.
Murphy, *Semin. Cell Dev. Biol.*, 20:138-145, 2009.
O'Callaghan et al., *Infect. Immun.*, 65:1571-1578, 1997.
Ong and Leung, *Immun. Allergy Clincis of NA*, 30:309-321, 2010.
Patel et al., *Infect. Immun.*, 55:3103-3110, 1987.
PCT Appln. WO 03/051825
PCT Appln. WO 03/106381
Perl et al., *Proc. Natl. Acad. Sci. USA*, 99:10482-10487, 2002a.
Perl et al., *Transgenic Res.*, 11:21-29, 2002b.
Pochetuhen et al., *Am. J. Pathol.*, 171(2):428-437, 2007.

Powers et al., *J. Infect. Diseases*, 2011 (IN PRESS)
Ragle and Bubeck Wardenburg, *Infect. Immun.*, 77:2712-2718, 2009.
Ragle et al., *Antimicrob. Agents Chemother.*, 54:298, 2010.
Reiss and Saftig, *Semin. Cell Dev. Biol.*, 20:126-137, 2009.
Rice et al., *Am. J. Physiol. Lung Cell Mol. Physiol.*, 283:L256-264, 2002.
Rubins et al., *J. Clin. Invest.*, 95:142-150, 1995.
Schulte et al., *Cell Death and Differentiation*, 14:1040-1049, 2007.
Schulz et al., *Circ. Res.*, 102(10):1192-1201, 2008.
Seals and Courtneidge, *Genes Dev.*, 17:7-30, 2003.
Shapiro and Weis, Cold Spring Harb. Perspect. *Biol.*, 1:a003053, 2009.
Song et al., *Science*, 274:1859-1866, 1996.
Steinhusen et al., *J. Biol. Chem.*, 276:4972-4980, 2001.
Tian et al., *Int. Immunol.*, 20:1181-1187, 2008.
Tomita and Kamio, Biosci. Biotechnol. *Biochem.*, 61:565-572, 1997.
Tweten, *Infection and Immunity*, 73 (10): 6199-6209, 2005.
Walker and Bayley, *J. Biol. Chem.*, 270:23065, 1995.
Wilke and Bubeck Wardenburg, *Proc. Natl. Acad. Sci. USA*, 107(30):13473-13478, 2010.
Wu et al., *Proc. Natl. Acad. Sci. USA*, 95:14979, 1998.
Vasioukhin et al., *Proc. Natl. Acad. Sci. USA*, 96:8551-8556, 1999.

What is claimed is:

1. A method of inhibiting Staphylococcal infection comprising administering an effective amount of a metalloprotease inhibitor to a patient, wherein the patient has been determined to have or be at risk of developing a Staphylococcal infection, wherein the metalloprotease inhibitor is an inhibitor of A Disintegrin and Metalloprotease 10 (ADAM10), and inhibits ADAM10 activity by inhibiting an ADAM10 polypeptide.

2. The method of claim 1, wherein the ADAM10 inhibitor is an inhibitory nucleic acid, polypeptide, or peptide, or small molecule.

3. The method of claim 1, wherein the ADAM10 inhibitor is an ADAM10 specific antibody.

4. The method of claim 1, wherein the patient is at risk of developing a Staphylococcus infection.

5. The method of claim 4, wherein the patient is immune deficient, is immunocompromised, is hospitalized, is undergoing an invasive medical procedure, is infected with influenza virus or is on a respirator.

6. A method of ameliorating disruption of an epithelial membrane comprising contacting an epithelial membrane that has been exposed to a pore-forming toxin with an inhibitor of A Disintegrin and Metalloprotease 10 (ADAM10).

7. The method of claim 6, wherein the pore-forming toxin is Hla.

8. The method of claim 6, wherein the pore-forming toxin is PLY.

9. A method for preventing disruption of a subject's epithelial barrier comprising administering an effective amount of a metalloprotease inhibitor to the subject, wherein the subject has been determined to have or be at risk of developing a Staphylococcal infection, wherein the metalloprotease inhibitor is an inhibitor of A Disintegrin and Metalloprotease 10 (ADAM10) and inhibits ADAM10 activity by inhibiting an ADAM10 polypeptide.

10. The method of claim 9, wherein the ADAM10 inhibitor is an ADAM10 specific antibody.

11. The method of claim 10, wherein the ADAM10 specific antibody is a polyclonal antibody, a monoclonal antibody, or an ADAM10-binding antibody fragment.

12. The method of claim 9, further comprising selecting the patient after the patient is diagnosed with a Staphylococcal infection.

13. The method of claim 9, wherein the patient is at risk of developing a *Staphylococcus* infection.

14. The method of claim 13, wherein the patient is immune deficient, is immunocompromised, is hospitalized, is undergoing an invasive medical procedure, is infected with influenza virus or is on a respirator.

15. A method of inhibiting Staphylococcal infection comprising administering an effective amount of a metalloprotease inhibitor to a patient, wherein the patient has been determined to have or be at risk of developing a Staphylococcal infection, wherein the metalloprotease inhibitor is an inhibitor of A Disintegrin and Metalloprotease 10 (ADAM10) and is selected from INCB7839; 1NCB3619; XL784; XL081; GI254023X; GW280264X; Batimastat; AG3340; BMS-275291; incyclinide; TAPI-1; and TIMP2.

16. The method of claim 15, wherein the inhibitor inhibits ADAM10 activity by inhibiting an ADAM10 polypeptide.

* * * * *

UNITED STATES PATENT AND TRADEMARK OFFICE
CERTIFICATE OF CORRECTION

PATENT NO. : 9,150,865 B2  
APPLICATION NO. : 13/884502  
DATED : October 6, 2015  
INVENTOR(S) : Juliane Bubeck Wardenburg Page 1 of 1

It is certified that error appears in the above-identified patent and that said Letters Patent is hereby corrected as shown below:

On the title page item (57), line 3, ABSTRACT "ADAMIO" should read --ADAM10--.

In the claims,

Claim 15 column 53 at line 19 "1NCB3619" should read --INCB3619--.

Signed and Sealed this
Sixteenth Day of February, 2016

Michelle K. Lee
*Director of the United States Patent and Trademark Office*